(12) United States Patent
Cioanta et al.

(10) Patent No.: US 11,771,781 B2
(45) Date of Patent: Oct. 3, 2023

(54) REPROCESSING OF CONTAMINATED REUSABLE DEVICES WITH DIRECT CONTACT OF PRESSURE WAVES

(71) Applicant: SANUWAVE, INC., Eden Prairie, MN (US)

(72) Inventors: Iulian Cioanta, Milton, GA (US); John Jackson, Buford, GA (US)

(73) Assignee: SANUWAVE, INC., Suwanee, GA (US)

( * ) Notice: Subject to any disclaimer, the term of this patent is extended or adjusted under 35 U.S.C. 154(b) by 0 days.

(21) Appl. No.: 17/977,529

(22) Filed: Oct. 31, 2022

(65) Prior Publication Data

US 2023/0125111 A1    Apr. 27, 2023

Related U.S. Application Data

(63) Continuation of application No. 17/313,951, filed on May 6, 2021, now abandoned.

(60) Provisional application No. 63/020,987, filed on May 6, 2020.

(51) Int. Cl.
| | |
|---|---|
| A61L 2/025 | (2006.01) |
| A61B 1/12 | (2006.01) |
| A61M 16/00 | (2006.01) |
| B08B 7/02 | (2006.01) |
| B08B 9/027 | (2006.01) |

(52) U.S. Cl.
CPC ........... *A61L 2/025* (2013.01); *A61B 1/122* (2013.01); *A61M 16/0003* (2014.02); *B08B 7/026* (2013.01); *B08B 7/028* (2013.01); *B08B 9/027* (2013.01); *A61L 2202/17* (2013.01); *A61L 2202/24* (2013.01); *A61M 2209/10* (2013.01); *B08B 2209/005* (2013.01); *B08B 2209/027* (2013.01)

(58) Field of Classification Search
CPC .. A61L 2/025; A61L 2202/17; A61L 2202/24; A61M 2209/10; A61M 16/0003; B08B 7/026; B08B 7/028; B08B 9/027; B08B 2209/005; B08B 2209/027; A61B 1/122
See application file for complete search history.

(56) References Cited

U.S. PATENT DOCUMENTS

| | | | |
|---|---|---|---|
| 5,240,675 A | 8/1993 | Wilk et al. | |
| 5,800,365 A * | 9/1998 | Zhong ................. | G10K 15/043 601/4 |
| 5,830,127 A | 11/1998 | Decastro et al. | |

(Continued)

FOREIGN PATENT DOCUMENTS

CN    101254319    9/2008

OTHER PUBLICATIONS

International Search Report and Written Opinion issued in corresponding International Patent Application No. PCT/US2021/031187 dated Sep. 9, 2021, 8 pages.

*Primary Examiner* — Sharidan Carrillo
(74) *Attorney, Agent, or Firm* — POLSINELLI PC

(57) ABSTRACT

A reusable apparatus, such as a medical instrument or tool, is decontaminated by applying pressure waves with direct contact of the pressure wave applicator to the reusable apparatus in an open bath in a sufficient dosage to remove contamination but without adversely affecting the ability to reuse the apparatus.

19 Claims, 50 Drawing Sheets

(56) References Cited

U.S. PATENT DOCUMENTS

| | | | | |
|---|---|---|---|---|
| 6,030,463 | A * | 2/2000 | Rusczyk | B08B 3/12 134/1 |
| 6,298,264 | B1 * | 10/2001 | Zhong | A61B 17/22004 604/20 |
| 6,447,718 | B1 * | 9/2002 | Carter | A61L 2/18 422/295 |
| 6,719,449 | B1 * | 4/2004 | Laugharn, Jr. | B01F 35/2115 366/127 |
| 2005/0038361 | A1 * | 2/2005 | Zhong | A61B 17/225 601/4 |
| 2005/0220665 | A1 * | 10/2005 | Ding | A61B 1/123 422/128 |
| 2009/0088670 | A1 | 4/2009 | Warlick et al. | |
| 2011/0034832 | A1 | 2/2011 | Cioanta et al. | |
| 2015/0238208 | A1 | 8/2015 | Adams et al. | |
| 2015/0314021 | A1 | 11/2015 | Botos et al. | |
| 2017/0081000 | A1 * | 3/2017 | Cioanta | B08B 3/024 |
| 2017/0119494 | A1 | 5/2017 | Vazales et al. | |
| 2020/0368377 | A1 | 11/2020 | Warlick | |
| 2021/0308001 | A1 * | 10/2021 | Cioanta | G10K 15/043 |
| 2021/0346533 | A1 | 11/2021 | Cioanta et al. | |

* cited by examiner

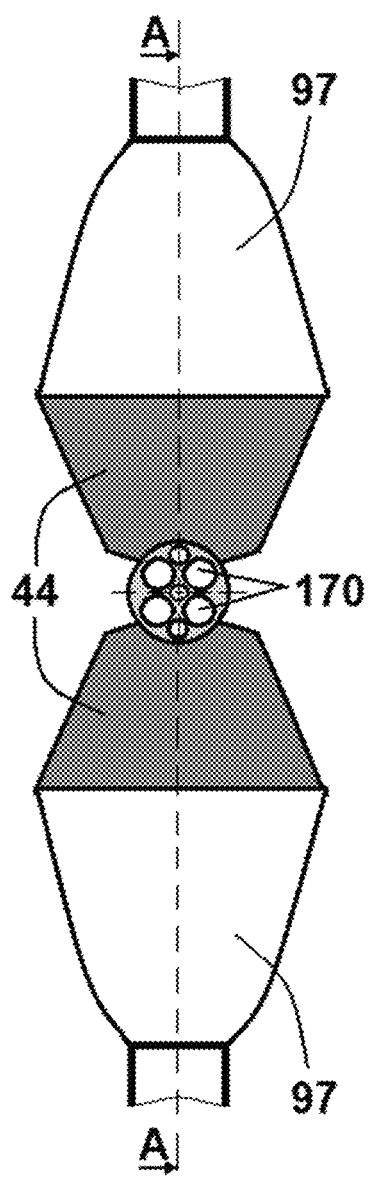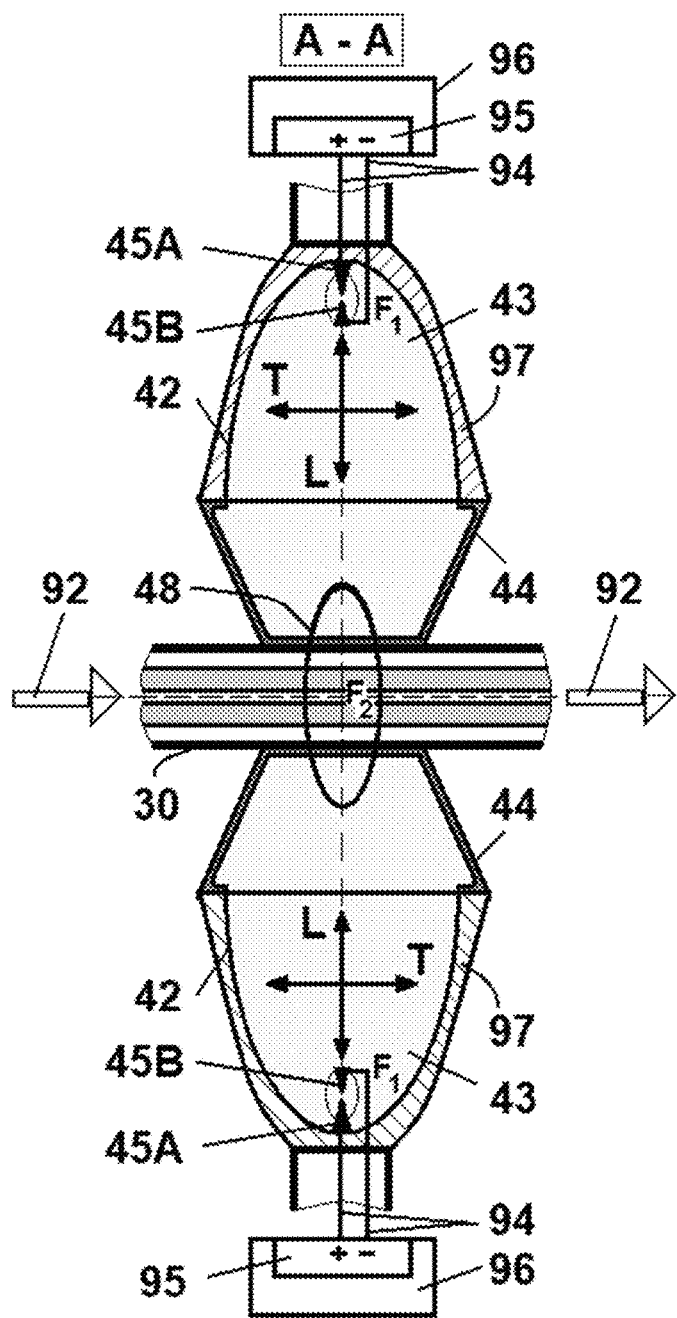
FIG. 19A
FIG. 19B

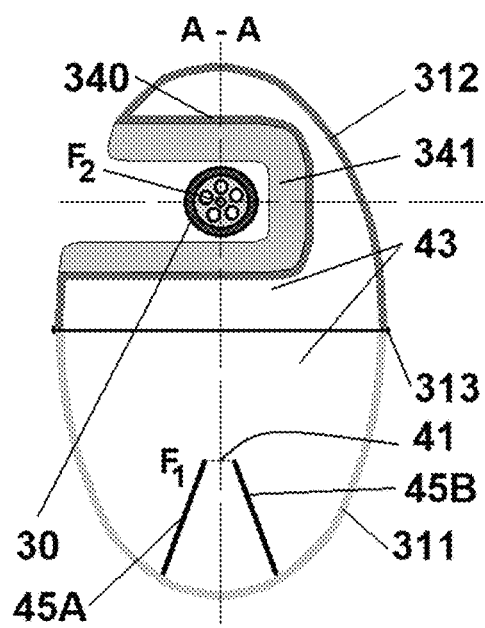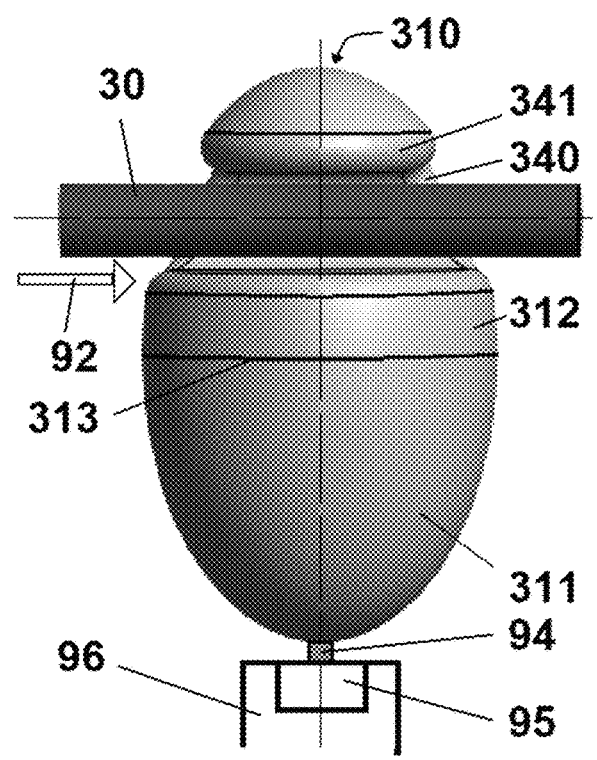
FIG. 34A
FIG. 34B
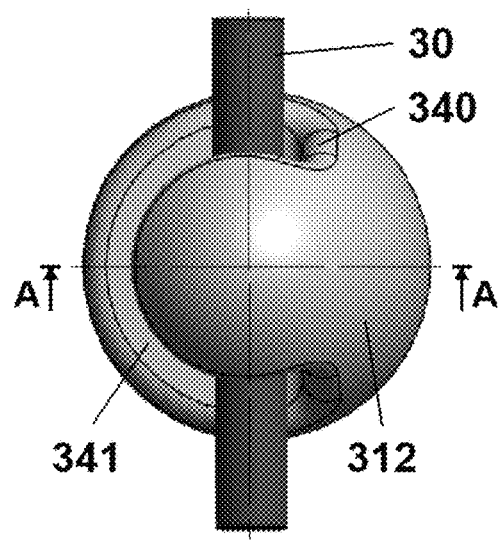
FIG. 34C

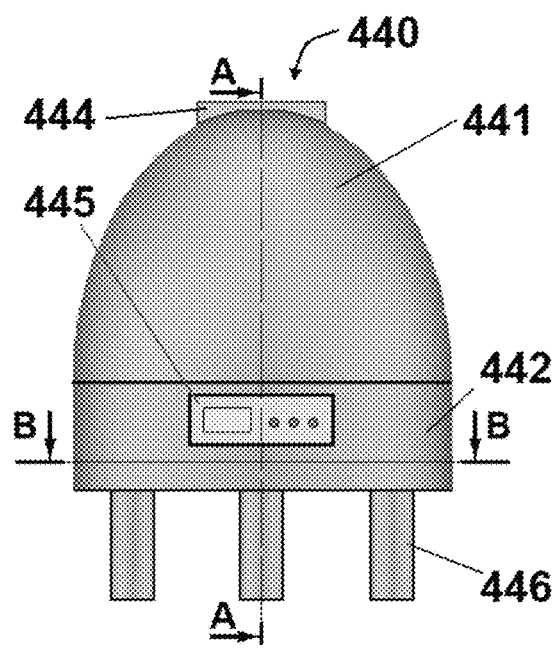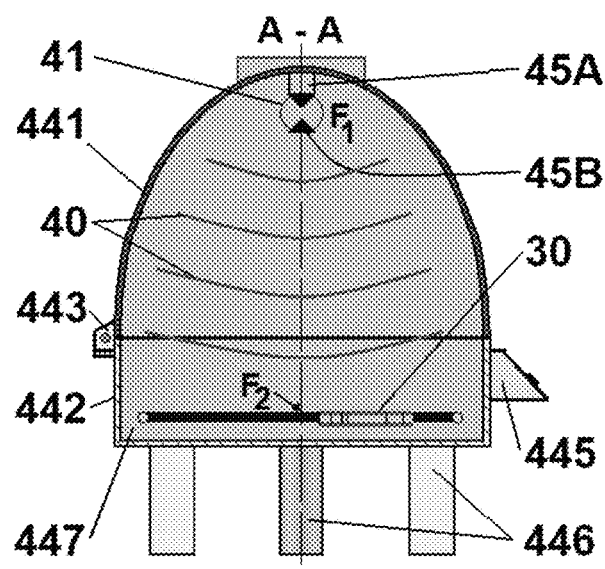
FIG. 44A
FIG. 44B
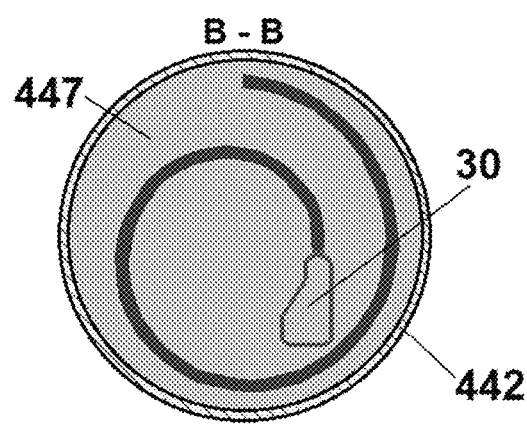
FIG. 44C

REPROCESSING OF CONTAMINATED REUSABLE DEVICES WITH DIRECT CONTACT OF PRESSURE WAVES

CROSS-REFERENCE TO RELATED APPLICATIONS

This application is a continuation of U.S. application Ser. No. 17/313,951, filed May 6, 2021, now abandoned, which claims the benefit of priority of U.S. Provisional Application No. 63/020,987 filed May 6, 2020, both of which are incorporated herein by reference in its entirety.

BACKGROUND OF THE INVENTION

An acute respiratory tract infection or disease is usually caused by an infectious agent, as bacteria, viruses. Lung acute responses can be produced also by irritant particles that are voluntary or accidentally ingested. Although the spectrum of symptoms of acute respiratory infection may vary, the onset of symptoms is typically rapid, ranging from hours to days after infection. Symptoms include fever, cough, sore throat, inflammation of the mucous membrane in the nose, shortness of breath, wheezing, or difficulty in breathing.

Bacteria can cause pneumonia or tuberculosis. The most common causes of bacterial lung infections in normal hosts include *Streptococcus pneumoniae, Haemophilus* species, *Staphylococcus aureus* and *Mycobacterium tuberculosis*.

The most known viral pathogens that affect lungs include influenza virus, parainfluenza virus, rhinovirus, respiratory syncytial virus (RSV) and severe acute respiratory syndrome coronavirus (SARS-CoV or COVID-19).

Fungus infections are also possible for the lungs. Aspergillosis is infection, usually of the lungs, caused by the fungus *Aspergillus*. A ball of fungus fibers, blood clots, and white blood cells may form in the lungs or sinuses. People may have no symptoms or may cough up blood or have a fever, chest pain, and difficulty breathing.

Acute respiratory infections are the leading cause of morbidity and mortality from infectious disease worldwide, particularly affecting the youngest and oldest people, as shown by the recent COVID-19 global pandemic or by mixed viral-bacterial infections. Although the knowledge of transmission modes is ever evolving, the current evidence indicates that the primary mode of transmission of most acute respiratory diseases is through droplets, direct contact (including hand contamination followed by self-inoculation) or infectious respiratory aerosols. In general, such infections can be contagious and spread rapidly.

Bronchitis is an acute inflammation of the bronchial lining. It is commonly related to cigarette smoking but is also triggered by environmental irritants such as chemical vapors, exhaust fumes or pesticides. In response to the inflammation, excess mucus is produced. This can block the small airways and reduce respiratory efficiency, for example, in chronic airways obstruction. Over-production of mucus leads to frequent coughing, which further irritates the tissues and causes even more mucus production.

One of the most common chronic afflictions of the lungs is the chronic obstructive pulmonary disease (COPD), which is a lung disease characterized by chronic obstruction of lung airflow that interferes with normal breathing. The more familiar terms 'chronic bronchitis' and 'emphysema' are no longer used, but are now included within the COPD diagnosis. Chronic bronchitis is inflammation of the lining of the bronchial tubes, which carry air to and from the air sacs (alveoli) of the lungs. It is characterized by daily cough and mucus (sputum) production. Emphysema is a condition in which the alveoli at the end of the smallest air passages (bronchioles) of the lungs are destroyed as a result of damaging exposure to cigarette smoke and other irritating gases and particulate matter.

Another pulmonary disease that can turn chronic is the idiopathic pulmonary fibrosis (IPF). This disease is a progressive interstitial lung disease, which is proposed to develop as a result of overexuberant remodeling following pulmonary epithelial damage, and which is characterized by chronic inflammation, alveolar epithelial hyperplasia, and deposition of extracellular matrix leading to development of a permanent "scar".

When any of the above-mentioned lung diseases reach a phase of sever oxygenation impairment (pulmonary insufficiency) ventilators or respirators devices/system are used. A ventilator or a respirator is a machine that helps a patient breathe by blowing oxygen into the lungs and removing carbon dioxide out of the lungs. The ventilator is attached to a breathing tube at one end that is placed in the person's mouth or in an opening through the neck into the windpipe (trachea), which is called a tracheostomy. If mucus collects, the lungs do not get enough oxygen. The mucus can also lead to pneumonia. To get rid of the mucus, a procedure called suctioning is needed. This is done by inserting a small thin tube into the person's mouth or neck opening to vacuum out the mucus. Such devices or systems have reusable parts that will require cleaning and high-level disinfection in between treatment of different patients. That is warranted by the contamination with individual bacteria and viruses, or sometimes by the formation of biofilms. The biofilms can comprise one or more microorganisms such for example as bacteria, fungi, protozoa, archaea, algae and/or microscopic parasites as viruses.

Uniform and standardized recommendations for reprocessing of anesthetic and ventilatory equipment are still lacking. The uncertainty in this field is emphasized by the various methods that are described in the literature, which include pasteurization, immersion baths, formaldehyde cabinets, automated washers/disinfectors and sterilization procedures like autoclaving, ethylene oxide and gaseous formaldehyde. Based on the classification of anesthetic and ventilatory equipment as semi-critical items, high level disinfection must be regarded as the appropriate decontamination procedure. The high-level disinfection procedures lack an integrated and all-inclusive reprocessing cycle, which consists of cleaning, disinfection, rinsing and drying. Also, there are automated washers/disinfectors—either based on hot water disinfection or chemo-thermic processing that are used for a standardized reprocessing of anesthetic and ventilatory equipment.

Besides ventilators and respirators, other medical systems that can be heavily contaminated during usage are endoscopes, arthroscopes, laparoscopes, bronchoscopes, nasopharygoscopes, duodenoscopes, cystoscopes, sigmoidoscopes, hemodialysis units, dental instruments, vaginal probes, rectal probes, pharyngeal probes, and cryosurgical instrumentation. The dental instruments, vaginal probes, rectal probes, pharyngeal probes, and cryosurgical instrumentation are usually sterilized in between usage and other systems as some of the hemodialysis units use disposable elements. The endoscopes, arthroscopes, laparoscopes, bronchoscopes, nasopharygoscopes, duodenoscopes, sigmoidoscopes and cystoscopes represent complex reusable instrumentation. Such instruments can be used anywhere from 300 to 1,200 times a year. It is estimated that in the U.S. alone 15 million flexible endoscope procedures are performed annually. Procedures are performed in a variety of settings, from a doctor's office to a hospital surgical suite. The methods employed to clean and disinfect these flexible endoscopes are also very diverse. A key concern, no matter where these procedures are done, is how clean these scopes are after reprocessing. With the prevalence of highly contagious diseases such as Hepatitis B and Acquired Immune Deficiency Syndrome (AIDS), effective cleaning, high-level disinfection or sterilization of such reusable medical devices it becomes mandatory to prevent infections. Due to their complexity, flexible endoscopes generally cannot be steam sterilized. Low temperature, highly specialized devices or methods must be employed to clean and disinfect these instruments.

There is a classification system first proposed by Dr. E. H. Spaulding that divides medical devices into categories based on the risk of infection involved with their use. This classification system is widely accepted and is used by the U.S. Food and Drug Administration (FDA), the Centers for Disease Control and Prevention (CDC), epidemiologists, microbiologists, and professional medical organizations to help determine the degree of disinfection or sterilization required for various medical devices. Three categories of medical devices and their associated level of disinfection are recognized:

Critical: A device that enters normally sterile tissue or the vascular system. Such devices should be sterilized, defined as the destruction of all microbial life. Examples include endoscopes used in sterile settings such as laparoscopic endoscopy and endoscopic accessories such as biopsy forceps and sphincterotomes.

Semi critical: A device that comes into contact with intact mucous membranes and does not ordinarily penetrate sterile tissue. These devices (e.g., gastrointestinal endoscopes) should receive at least high-level disinfection (HLD), defined as the destruction of all vegetative microorganisms, mycobacteria, small or nonlipid viruses, medium or lipid viruses, fungal spores, and some, but not all, bacterial spores.

Noncritical: Devices that do not ordinarily touch the patient or touch only intact skin, such as stethoscopes or patient carts. These items may be cleaned by low-level Disinfection Semi-critical disinfection involves disinfection of items that come in contact with mucous membranes and intact skin, but not with internal, natural sterile areas of the body. Cleaning of semi-critical items/equipment is an important step in the disinfection process to ensure the disinfecting of the items/equipment will be successful. The cleaning process must be thoroughly because organic material may protect microorganisms from the disinfection process and should take place between each device/equipment usage. In general, these systems will be disassembled (as appropriate) and thoroughly cleaned. Semi-critical items may be contaminated with dried or wet sputum and/or blood and should be cleaned using a detergent, rinsed, and dried prior to be used again. The high-level disinfection consists of immersing the device or equipment or system in a biocide solution for 5-minutes. Afterwards, the device or equipment or system should be removed from the solution and thoroughly rinsed using sterile water when practical, otherwise potable water is acceptable for semi-critical devices or equipment or systems not intended for use on immunocompromised patients or potentially immunocompromised patients. The device or equipment or system should be totally immersed for a minimum of 1-minute repeating this step for multiple consecutive times. Then all lumens must be manually flushed. Following the rinsing step, the device or equipment or system should be dried and stored in a suitable container for future use.

At this time, the FDA-cleared and marketed formulations of chemicals used during high-level disinfections include: ≥2.4% glutaraldehyde, 0.55% ortho-phthalaldehyde (OPA), 0.95% glutaraldehyde with 1.64% phenol/phenate, 7.35% hydrogen peroxide with 0.23% peracetic acid, 1.0% hydrogen peroxide with 0.08% peracetic acid, and 7.5% hydrogen peroxide. These products have excellent antimicrobial activity; however, some oxidizing chemicals (e.g., 7.5% hydrogen peroxide, and 1.0% hydrogen peroxide with 0.08% peracetic acid) reportedly have caused cosmetic and functional damage to endoscopes. Ethylene Oxide (EtO) sterilization of flexible endoscopes is infrequent because it requires a lengthy processing and aeration time (e.g., 12 hours), is costly, inefficient, cannot sterilize residual gross soil, affects endoscope durability, and is a potential hazard to staff and patients. The two products most commonly used for reprocessing endoscopes in the United States are glutaraldehyde and an automated, liquid chemical sterilization process that uses peracetic acid. The FDA-cleared labels for high-level disinfection with >2% glutaraldehyde at 25° C. range from 20-90 minutes. Clearly, other new or validated low-temperature reprocessing technologies and/or endoscope designs are needed.

There are also new high-level disinfectants and agent specific machines/reprocessors in the marketplace. If a reprocessor is used, the endoscope and endoscope components are placed in the reprocessor and all channel connectors should be attached according to the reprocessor manufacturers' instructions to ensure exposure of all internal surfaces with the high-level disinfectant solution. After high level disinfection, the endoscopes' channels are rinsed and flushed with sterile or filtered water to remove the disinfectant solution. The rinse water is discarded after each use/cycle. Then the endoscope's channels are flushed with 70% to 90% ethyl or isopropyl alcohol and dried using filtered forced air. The final drying steps greatly reduce the risk of remaining pathogens and the possibility of recontamination of the endoscope by waterborne microorganisms.

For hemodialysis units, the noncritical surfaces (e.g., dialysis bed or chair, countertops, external surfaces of dialysis machines, and equipment as scissors, hemostats, clamps, blood pressure cuffs, stethoscopes) should be disinfected with an EPA (Environmental Protection Agency) registered disinfectant unless the item is visibly contaminated with blood. When blood is present a tuberculocidal agent or a disinfectant with specific label claims for hepatitis virus and HIV or a 1:100 dilution of a hypochlorite solution is used. This procedure removes soil on a regular basis and maintains an environment that is consistent with good patient care. Hemodialysis systems usually are disinfected by chlorine-based disinfectants (e.g., sodium hypochlorite), aqueous formaldehyde, heat pasteurization, ozone, or peracetic acid. However, new methods are needed, which can eliminate the use of chemical disinfectants that have significant environmental impact or using long-cycles of high temperature (pasteurization) that reduces significant the longevity of dialysis components exposed to it.

SUMMARY OF THE INVENTION

In the last decades, there were new types of viruses that produced severe infections in humans (Severe Acute Respiratory Syndrome (SARS-CoV) in 2003, porcine flu in 2009, Middle East Respiratory Syndrome (MERS) in 2015, and lately the Corona Virus Disease (COVID-19) in 2019/2020) or seasonal re-occurrence of certain diseases as flu or influenza. There are also known super virulent viruses that produce on a large-scale hepatitis infection on global population, or the human immunodeficiency virus (HIV) that killed many people or requires extensive treatments to keep it in check. Other viral infections as Ebola, Dengue, West Nile, Zika and Chikungunya, to name a few, are started to pose significant threat to human population. Besides the infections produces by viruses, the bacterial or fungal infections can also pose significant strain on the medical system and the health of humans. The mouth, eyes, nasal cavity, throat, lungs, stomach, intestines are susceptible areas and organs to such infections, since there is a conduit or conduits linked to them that gives a direct pathways access for the external pathogens to penetrate inside the human or animal body. These infections can be easily transmitted through bodily fluids, and during exploratory or treatment procedures involving endoscopes or treatments using ventilators or hemodialysis systems, if the reprocessing of these medical devices/systems or subassembly or parts or accessories is done improperly or is not sufficient to kill all the germs.

The actual practices used to clean and disinfect reusable parts or subassembly or devices/systems are not uniformly defined and prone to mistakes, which can result in the use of contaminated medical systems. The contamination is in the form of planktonic bacteria, virus spores, fungi, and biofilms. Furthermore, the actual practices are relying heavily on chemicals and energy intensive methods that have important environmental consequences, and require substantial protection equipment for the health personnel responsible for cleaning and decontamination, which generates extra waste and drive the costs up. There are electronic pumps that can be used to irrigate the endoscopes that are used when rinsing the lumens of the endoscopes prior to manual or semi-manual high-level disinfection. Failure to rinse the endoscope completely may reduce the effectiveness of the disinfection cycle. Even more, the cleaning and decontamination processes are time consuming, tedious, and require numerous subsequent steps, which makes the personnel performing these processes susceptible to miss or skip some of the steps. This can contribute to improper cleaning and decontamination of these reusable parts or subassembly or devices/systems, which can ultimately generate infections with significant health consequences and even death.

For the manual cleaning and disinfection of endoscopes, ventilators' or hemodialysis units' tubing or specific components, usually appropriately sized cleaning brushes and specific biocide solutions are used to remove and flush the biological and pathogenic material from the lumens of the endoscopes or the tubing or specific components used for ventilators or hemodialysis units. The usage of an appropriately sized cleaning brushes without kinks and with soft bristles is needed to have contact on the side walls of the endoscopes' suction/biopsy channels or ventilators or hemodialysis' tubing so that debris can be cleared. Slow movements inserting the brush and friction while removing the brush will loosen debris that may be on both proximal and distal sides of the channels. If the brush is too small, there will be little contact with the debris or channel wall. If the brush is too large, can get lodged in the channel and the bristles may be deflected upward as the brush travels the channel merely swiping the sides of the channel. The condition of the brush must be assured to be safe. If the protective tip is missing, the coiling unbraided, some bristles absent, or the delivery tube (whether metal or plastic) kinked, the brush may tear a hole as it travels down the channel lumen. Because this occurs after the leakage test has been performed, the hole may go unnoticed and the subsequent patient be exposed to bio-burden and cleaning chemical retained in the scope. There is no maximal number of times each lumen should be brushed, however the minimal number should be identified as "until the brush comes out clean."

In the case of reprocessors or automatic systems used to clean and disinfect endoscopes or any kind of tubing used for respirators or hemodialysis units, these systems rely heavily on harsh chemicals that wash the exterior surfaces and are also forced circulated through the tubing and lumens, with the hope to remove all pathogens. If the connections of the endoscopes or reprocessed tubing to the feeding biocidal fluid lines of the reprocessors are done improperly or the cleaning and high-level disinfection process is interrupted or faulty due to wrong programming of the reprocessor, that can generate an improper processing, which is completely transparent (non-detected) to the operator. Even more, the diminished processing of difficult to reach areas or intricate geometries, can allow the survival of pathogens after the reprocessing inside the endoscopes or any kind of tubing used for respirators or hemodialysis units.

This is why new methodologies and technologies are needed for cleaning and high-level disinfection of endoscopes, arthroscopes, laparoscopes, bronchoscopes, nasopharygoscopes, duodenoscopes, cystoscopes, ventilators, respirators, hemodialysis units, which will be easy to apply, environmentally friendly, and non-specific to the type of pathogen. This can be accomplished by using the focused acoustic pressure shockwaves or special high-intensity pressure waves or low-frequency ultrasound based on specific characteristics that they possess, as follows:

a. They are applied from the exterior of the instrumentation, which can help with the cleaning and decontamination of all sorts of instrumentation with large dimensional variation.
 b. Do not have detrimental effects on the cleaned surfaces or materials, due to specific targeting of their action only on the biological and pathogenic material.
 c. Can get in difficult to reach areas of the instrumentation for an efficient cleaning and decontamination of the "hiding" pathogens.
 d. Do not generate any heat during processing, which is significant for keeping intact the quality of materials used in the construction of the instrumentation, and do not create any restrictions on their usage.
 e. Are non-specific to a type of pathogen, as usually the chemicals are, due to their pure mechanical/kinetic action on the contamination material.
 f. Do not generate pathogen mutations, since the detaching from the instrumentation surfaces (exterior and interior) and eventual breaching of pathogen integrity is relying only on mechanical forces.
 g. They are capable to clean and disinfect intricate accessories for the reusable devices or systems, as the respirator's masks, endoscopes or hemodialysis units or respirators' valves, etc.
 h. Do not require energy intensive and complicated processes, which makes them energy and time efficient.
 i. Can be used in combination with any fluid solution that can contain only purified water, or if needed with any type of biocides or enzymes.

j. Do not require an extensive number of steps for processing, which reduces possible mistakes by the personnel involved in the cleaning and disinfection process.

k. Can combine the cleaning and disinfection in one single phase.

l. Seamlessly can be integrated into existing cleaning and disinfection systems and processing, without any major modifications.

m. Can be integrated in manually or semi-automated or completely automated cleaning and disinfection systems/processes or equipment.

n. Are environmentally friendly.

In general, the focused acoustic pressure shockwaves or some special high-intensity pressure waves or low-frequency ultrasound produced by the proposed embodiments will have a compressive phase and a tensile phase during one cycle of the acoustic pressure shockwaves/pressure waves. In the compressive phase, positive compressive pressures are produced and in tensile phase significant negative pressures are generated that produce cavitation bubbles, which when reaching their full dimensions implode/collapse with high-speed jets in excess of 100 m/s. These two synergetic effects, work in tandem to produce forces that can dislodge bacteria, viruses, fungi, biological material from the external and internal surfaces of the reprocessed systems and also can destroy individual bacterium, virus, fungus, and other micro-organisms by affecting their structural integrity.

The high mechanical tension and pressures found at the front of the focused acoustic pressure shockwave or of the special high-intensity pressure waves distinguishes them from other kinds of sound waves, such as ultrasonic waves. The focused acoustic pressure shockwaves or special high-intensity pressure waves consist of a dominant compressive pressure pulse, which climbs steeply up to maximum one hundred Mega-Pascals (MPa; 1 MPa=10 bar) within a few nanoseconds and then falls back to zero within a few microseconds. The final portion of the pressure profile is characterized by negative pressures of minus five to fifteen Mega-Pascals (tensile region of the acoustic pressure shockwave/pressure waves), with potential to generate cavitation in any kind of fluids. The bubble diameter grows as the energy is delivered to the bubble. This energy is released from the bubble during its collapse (implosion) in the form of high-speed pressure micro jets and also produce rapid transient high temperatures. For focused acoustic pressure shockwaves or special high-intensity pressure waves to be effective in the cleaning and high-level disinfection processes, they must be focused or concentrated (semi-focused) or completely unfocused when sent towards the point at which their effect is needed. In the cleaning/disinfection region in general there are two basic effects, with the first being characterized as direct generation of mechanical forces (primary effect from the positive, compressive high-pressure rise), and the second being the indirect generation of mechanical forces (high velocity pressure micro jets) produced by cavitation (secondary effect from the negative, tensile pressure region).

A focused acoustic pressure shockwave or a special high-intensity pressure wave can travel larger distances easily (based on the amount of energy put in them at the point of origination), as long as the acoustic impedance of the medium remains the same. At the point where the acoustic impedance changes, energy is released and the acoustic pressure shockwave or pressure waves are reflected or transmitted with attenuation. Thus, the greater the change in acoustic impedance in between different substances, the greater the release of energy is generated. Based on this principle, when shockwaves/pressure waves created in a fluid reach a surface made of different material/solid material, where the acoustic impedance changes, they deposit their energy and generate specific forces that easily dislodge any organic material or pathogens from solid surfaces as the endoscope's lumens or any tubing internal or internal surfaces or from intricate surfaces found in valves, connectors or masks, to name a few. The same forces can also destroy the external membrane/envelope of bacteria and viruses, or disintegrate the structural integrity of fungi or micro-organisms.

If the endoscope or reusable tubing from different medical devices or parts of these systems/devices are placed before the focal volume of the shockwaves (where the maximum pressures gradients are found and consequently energy transmission/deposit), then the actual cleaning and high-level disinfection is done with unfocused waves. In the unfocussed region, the shape of the pressure signal is more sinusoidal in shape, with the maximum positive pressures and the maximum negative pressures having lower values when compared to the focused shockwaves, which translates in less energy carried by unfocused pressure waves in the targeted region when compared to the focused shockwaves. This is why the unfocused pressure waves are used where lower energies are needed for cleaning and high-level disinfection of very sensitive instruments, devices, systems or their specific reusable parts.

The focused acoustic pressure shockwaves or specific high-intensity pressure waves (planar, pseudo-planar, radial, or unfocused waves) are highly controlled to generate an energy output that will not produce any undesired damage to the instruments that are cleaned and disinfected. This is accomplished based on reflector geometry and material, energy setting (input energy level of the focused acoustic pressure shockwaves or pressure waves), the total number of focused acoustic pressure shockwaves or pressure waves (planar, pseudo-planar, radial, or unfocused waves) used for cleaning/disinfection, and their frequency per second. All these parameters dictate the total acoustic energy delivered in one cleaning and high-level disinfection session. Reflector geometry directly controls the delivery of the shockwaves (focused or unfocused) or pressure waves into the targeted region and shapes their spatial distribution in the cleaning and high-level disinfection area.

The energy settings (energy input into focused acoustic pressure shockwaves or special high-intensity pressure waves (planar, pseudo-planar, radial, or unfocused waves)) directly affect the pressure output into the cleaning and high-level disinfection region/zone and together with number of acoustic pressure shockwaves/pressure waves and their frequency per second, determine the total amount of energy used to reprocess the targeted devices/systems.

For cleaning and high-level disinfection of endoscopes, arthroscopes, laparoscopes, bronchoscopes, nasopharygoscopes, duodenoscopes, cystoscopes, ventilators, respirators, hemodialysis units, another approach is to use ultrasound waves that have low frequency, to not produce any heating effects. The ultrasound systems are placed either in direct contact or non-contact with the devices or components needing cleaning and high-level disinfection. Ultrasound has a tensile phase made of positive pressures and a tensile phase that encompasses the negative pressures. In comparison to the shockwaves or high intensity pressure waves, the repetition (frequency) of ultrasound phases is much higher. Thus, the ultrasound used in the embodiments presented in this invention have a frequency in between 10 to 900 kHz, and more preferable 30 to 300 kHz, which is much higher compared to 1 to 12 Hz (preferable 2 to 10 Hz) used for shockwaves/pressure waves. Also, for ultrasound the sequence of phases is continuous from positive pressure to negative pressures and then again to positive pressures in a sinusoidal continuous variation. This has an influence on the cavitation. Due to cyclical acoustic wave of the ultrasound, the cavitation bubbles growth is cyclical too and in general they do not reach the same size as the shockwave cavitation bubbles, which translates in less energy generated during their collapse. In order to reach the proper size necessary to collapse by themselves, for the ultrasound cavitation bubbles it takes many ultrasound cycles. Also, due to continuous oscillation in dimensions, the ultrasound cavitation bubbles grow slowly in dimension and accumulate heat, which produce a collapse as a hot spot. The combination of the micro jets and hot spots created by the collapsing ultrasound cavitation bubbles can contribute both to the dislodging of the contamination material from instruments surfaces and also to the pathogen killing. In the end, the ultrasound vibrations and the cavitation bubbles generated by it have benefic effects on cleaning and high-level disinfection of endoscopes, arthroscopes, laparoscopes, bronchoscopes, nasopharygoscopes, duodenoscopes, cystoscopes, ventilators, respirators, hemodialysis units, and other medical devices or components that requires reuse.

Thus, focused acoustic pressure shockwaves or special high-intensity pressure waves (planar, pseudo-planar, radial, or unfocused waves) or low-frequency ultrasound are destroying the integrity of the bacteria by affecting their membrane integrity. That is done via interference with bacterium mechano-transduction (transport of fluids across bacterium membrane) due to significant localized pressure variations produced when the pressure pulses are generated in the region where the pathogen exists, which create sudden variation in pressure from high positive pressures to significant negative pressures. In the simplest terms, the membrane pores of the bacterium remain opened due to sudden pressure changes and the bacteria swells until the integrity of the membrane is compromised. According to the published scientific literature, the bacterial membrane mechano-transduction occurs at pressures of 3 MPa or less, which is well in the realm of pressure generated by focused acoustic pressure shockwaves or special high-intensity pressure waves (planar, pseudo-planar, radial, or unfocused waves) or low-frequency ultrasound.

For viruses their shell integrity can be compromised due to the penetrating forces generated by the micro jets produced by the collapse of cavitational bubbles formed in the tensile phase by the negative pressures. Another factor that can act on viruses are the transient high temperatures produced during cavitational bubbles collapse, which can denature the virus and its DNA material.

Due to pure mechanical process, produced by focused acoustic pressure shockwaves and special pressure waves (planar, pseudo-planar, radial, or unfocused waves) or low-frequency ultrasound, which is involved in the destruction of individual bacteria or viruses, there is no biochemical process involved that can produce mutations. Thus, there is no developed resistance of bacteria or viruses to focused acoustic pressure shockwaves or special pressure waves (planar, pseudo-planar, radial, or unfocused waves) or low-frequency ultrasound, due to their mutation, natural selection, transformation, transduction or conjugation.

The focused acoustic pressure shockwaves and special pressure waves (planar, pseudo-planar, radial, or unfocused waves) or low-frequency ultrasound produce a kinetic effect on the exterior or interior of the endoscopes or tubing from respirators or hemodialysis units, due to the forces generated by the compressive positive pressures of their compressive phase and due to the forces associated with micro-jets produced during cavitation bubbles collapse from their tensile phase. That can have a benefic influence in dislodging different pathogens as viruses, bacteria, micro-organisms, biological material, and any type of biofilms from the reprocessed items. Furthermore, the same effects can be used to destroy the structural integrity of pathogens, which can disable them and eliminate their infectious capability.

In some embodiments of this invention, the dislodged individual pathogens or fragments of biofilms from the exterior or interior surfaces of the reprocessed devices/systems or subassemblies or parts or accessories can be flushed away via fluid circulation (purified water or mixture of purified water and biocides) after application of shockwaves or pressure waves or low-frequency ultrasound. This allows an even better chance to thoroughly clean and disinfected the reprocessed devices/systems or subassemblies or parts or accessories.

In other embodiments, the flushing process of the reprocessed devices/systems or subassemblies or parts or accessories can be also done concomitantly during the actual cleaning and high-level disinfection that employs focused acoustic pressure shockwaves and special pressure waves (planar, pseudo-planar, radial, or unfocused waves) or low-frequency ultrasound. However, even in these situations, the amount of biocide used is reduced when compared to existing techniques, which significantly contributes to less environmental impact during the discarding of such processing fluids and also reduces the amount of rinsing needed in the subsequent step of cleaning and high-level disinfection.

BRIEF DESCRIPTION OF THE DRAWINGS

FIG. 19A is a schematic representation of a manual or semi-automatic system for cleaning and high-level disinfection of endoscopes or reusable tubing from ventilators and dialysis machines and other medical devices using two confocal and opposite focused shockwave applicators in direct contact with the endoscope or tubing, according to one embodiment of the present invention.

FIG. 19B is a cross-sectional view of the system illustrated in FIG. 19A taken along line A-A, according to one embodiment of the present invention.

FIGS. 34A-34C are schematic representations of a system using focused shockwaves applicators having full-ellipsoidal reflectors with a lateral slot to move the endoscope or reusable tubing from ventilators and dialysis machines and other medical devices through the focal volume during cleaning and high-level disinfection, according to one embodiment of the present invention.

FIG. 44A is a schematic representation of an automatic shockwaves or pseudo-planar waves or radial waves reprocessor with one reflector for cleaning and high-level disinfection of endoscopes or tubing from ventilators and dialysis machines and other medical devices, according to one embodiment of the present invention.

FIG. 44B is a cross-sectional view along line A-A of FIG. 44A, according to one embodiment of the present invention.

FIG. 44C is a cross-sectional view along line B-B of FIG. 44A, according to one embodiment of the present invention.

DETAILED DESCRIPTION OF THE INVENTION

Embodiments of the invention will be described with reference to the accompanying figures, wherein like numbers represent like elements throughout. Further, it is to be understood that the phraseology and terminology used herein is for the purpose of description and should not be regarded as limiting. The use of "including", "comprising", or "having" and variations thereof herein is meant to encompass the items listed thereafter and equivalents thereof, as well as additional items. The terms "connected", and "coupled" are used broadly and encompass both direct and indirect mounting, connecting, and coupling. Further, "connected" and "coupled" are not restricted to physical or mechanical connections or couplings.

It is a further objective of the present inventions to provide a means of controlling the energy via the amount of energy generated by the focused acoustic pressure shockwave, or special pressure waves (planar, pseudo-planar, radial, or unfocused waves), or low-frequency ultrasound generators (using the energy settings), total number of the shockwaves or pressure waves, repetition frequency for the shockwaves or pressure waves or ultrasound, duration of the cleaning and high-level disinfection process, and through the special construction of the reflectors used in some of the applicators presented in the present inventions.

It is a further objective of the present inventions to provide focused shockwaves or special high-intensity pressure waves (planar, pseudo-planar, radial, or unfocused waves) or low-frequency ultrasound generating devices that are modular, do not need high maintenance and can, if needed, be applied/used in conjunction and synergy with other devices and cleaning and high-level disinfection systems.

The inventions summarized below and defined by the enumerated claims are better understood by referring to the following detailed description, which is preferably read in conjunction with the accompanying drawing/figure. The detailed description of a particular embodiment, is set out to enable one to practice the invention, it is not intended to limit the enumerated claims, but to serve as a particular example thereof.

The inventions described herein are not intended to be limited to specific embodiments that are provided by way of example, but extend to the full scope of such claims of a corresponding issued patent.

Also, the list of embodiments presented in this patent is not an exhaustive one and for those skilled in the art, new applications and optimization methods can be found within the scope of the invention.

Figure 1:
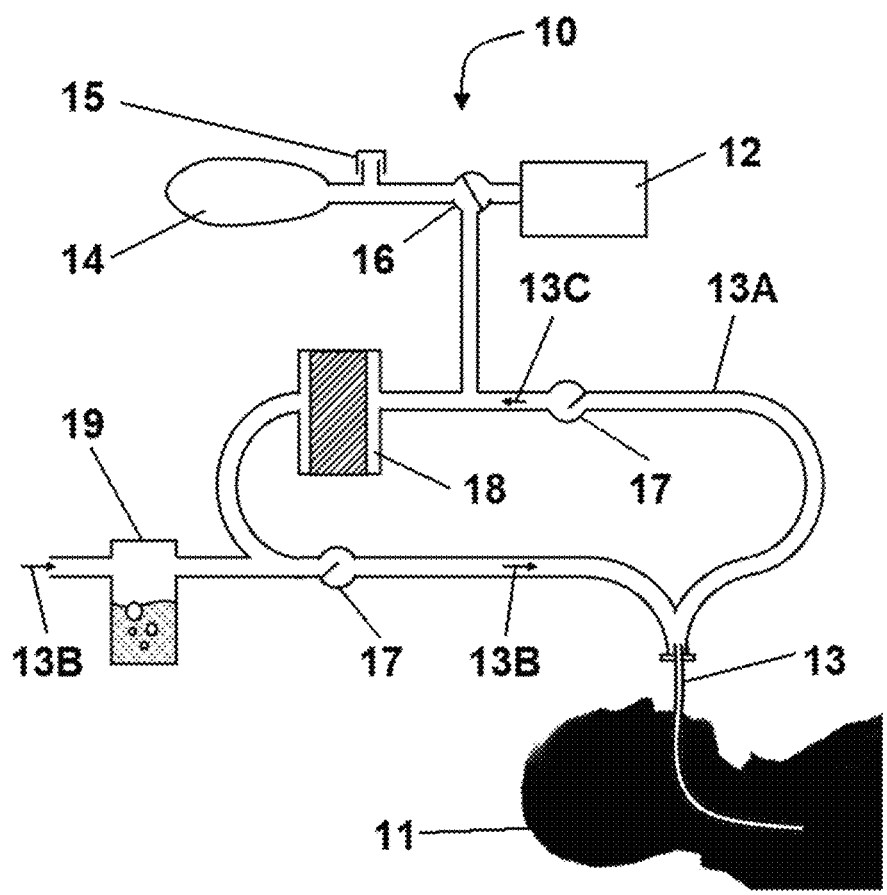
FIG. 1 is a schematic representation of ventilator system structure and functionality known in the prior art.
Figure 2:
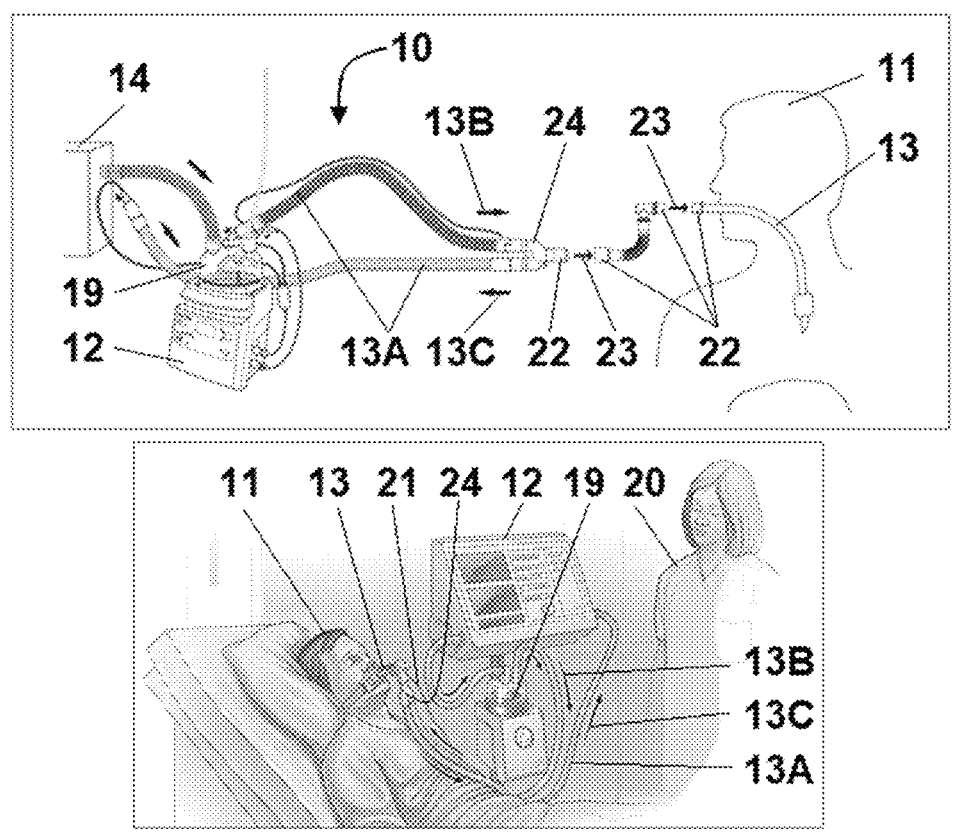
FIG. 2 is a schematic representation of ventilators' reusable tubing system known in the prior art.

As presented in FIGS. 1 and 2, a ventilator system 10 is a machine that helps a patient 11 breathe by blowing oxygen into the lungs and removing carbon dioxide out of the lungs. The ventilator console 12 is attached to a ventilator intubating breathing tubing 13 at one end that is placed in the patient's 11 mouth or in an opening through the neck into the windpipe (trachea), which is called a tracheostomy. The ventilator external tubing 13A is made of the inspiratory and expiratory breathing tubing. The breath in air direction 13B is the inspiratory direction and the breath out air direction 13C is the expiratory direction. The selection of airflow direction is done with a series of one-way valves 17. The adjustable pressure-limiting valve 15 (commonly abbreviated to APL valve, and also referred to as an expiratory valve, relief valve or spill valve) is a type of flow control valve used in anesthesia systems or ventilators, as part of a breathing system. It allows excess fresh gas flow and exhaled gases to leave the system while preventing ambient air from entering. The air or oxygen bag/reservoir 14 provides via the switch 16 the gas or gases mixture necessary for the inspiration phase of the patient 11. The expiration gas mixture contains carbon dioxide ($CO_2$) and to purify the air from that, a $CO_2$ absorber 18 is used on the breath out air direction 13C. Sometimes it is necessary to introduce anesthetic gas or medication via the anesthetic gas or medication vaporizer 19. As seen in FIG. 2, for patient feeding during the use of the ventilator system 10, the nasogastric tube 21 is introduced through the esophagus by the medical personnel 20, who also supervises the correct functioning and possible adjustments of the ventilator system 10. For easily connect and disconnect different parts of the ventilator intubating breathing tubing 13 and/or the ventilator external tubing 13A, the connectors 23 and the connector snapping parts 22 are used. The Y-connector piece 24 is used to separate or converge the inspiratory and expiratory breathing tubing.

In general, the ventilators' breathing circuits, including the ventilator intubating breathing tubing 13 and the ventilator external tubing 13A, should be changed every 7 days for a patient that uses the ventilator system 10 for long period of time. Between uses on different patients, the reusable contaminated components of the breathing system or patient circuit (e.g., tracheal tube/ventilator intubating breathing tubing 13 or face mask) inspiratory and expiratory ventilator external tubing 13A, Y-connector piece 24 (see FIG. 2), air or oxygen bag/reservoir 14, one-way valves 17, and humidifier 25 (see FIG. 2), must be subject to high-level disinfection. The ventilator's humidifier 25, the ventilator intubating breathing tubing 13 and ventilator external tubing 13A are connected to the patient's mouth and nose with a closed cycle. The exudates and bacteria or viruses from inside the body during exhalation can contaminate the ventilator's pipeline. The humidified and heated air in the ventilator external tubing 13A can form a moist, warm, and airtight environment, and can form condensed water under the interaction with the cold air outside the ventilator external tubing 13A, providing an environment for the pathogens to multiply and form aerosols with inhaled gases, enter the respiratory tract, and cause repeated lung infections.

Interesting to note that inadequate and prolonged use of ventilators can cause the ventilator-associated pneumonia (VAP), which is generated by microbial contamination in the lungs. Microbes may enter the lung during intubation or mechanical ventilation. Common species are *Pseudomonas, Staphylococcus aureus, Enterobacteriaceae, Streptococcus, Haemophilus, Acinetobacter*, and *Neisseria*. These pathogens generally remain in the lung, spreading into blood or pleural space in less than ten percent of cases. The source of causative pathogens are the bronchoscopes, tubing, endotracheal cuffs, and other respiratory accessories and instruments. Pathogens can also originate from the environment (air, water, fomites) or be transmitted between staff and patients. These emphasize even more the necessity to use cleaning and high-level decontamination for certain components of the ventilators, especially in the cases where highly contagious pathogens are involved.

Chemical and physical methods of disinfection are used to clean ventilator's different parts, as inspiratory and expiratory ventilator external tubing 13A, Y-connector piece 24 (see FIG. 2), air or oxygen bag/reservoir 14, one-way valves 17, and humidifier 25. Usually, the entire ventilator external tubing 13A is removable, including the adjustable pressure-limiting valve 15, which may also have a flow measurement device or a water trap, or both. The physical methods for high-level disinfection include hot-water disinfection (pasteurization) or steam (e.g., autoclaving at lower temperature). Pasteurization is a non-toxic, cost-effective alternative to high-level disinfection with chemical germicides. Equipment should be submerged for at least 30 minutes in water at a temperature of about 70° C. (less than the temperature that typically damages plastic). Pasteurization can be accomplished using a commercial washer or pasteurizer. Steam sterilization is an inexpensive and effective method for sterilization or high-level disinfection, but it can be unsuitable for processing plastics with low melting points, powders or anhydrous oils. After pasteurization, wet equipment is typically dried in a hot-air drying cabinet and then dry-stored in closed packages. The use of mechanical or chemical cleaning and high-level disinfection for ventilator tubes can improve the qualification rate of disinfection and reduce the number of pathogen colonies in the tube. Unfortunately, bacterial and/or viral spores may survive after these methods. Microbiological sampling can be used to verify that high-level disinfection has resulted in the destruction of vegetative bacteria or viral particles. However, such sampling is not routinely recommended. The decontamination and high-level disinfection of ventilators is a process that takes 2 hours, which is time-consuming and results in a lot of wear and tear and time out of service.

Figure 3:
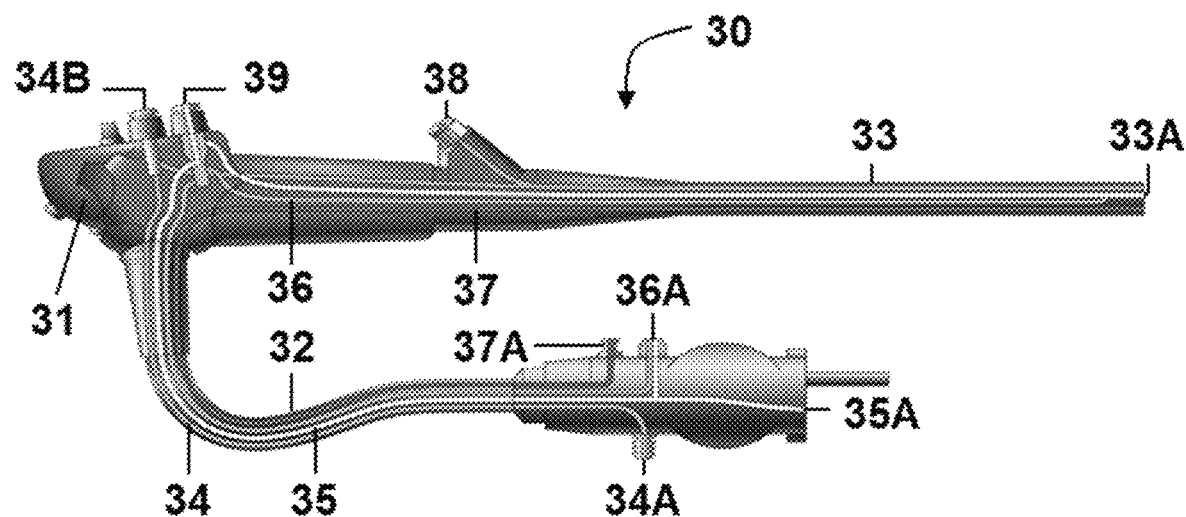
FIG. 3 is a schematic representation of endoscope structure and functionality known in the prior art.

Physicians also use medical tubing 30 (such as endoscopes and other medical device tubes), as presented in FIG. 3, to diagnose and treat numerous medical disorders. The flexible endoscope is constructed of several systems that operate simultaneously to produce a highly technical, yet effective diagnostic and therapeutic medical device. The basic design of most flexible endoscopes consists of a light guide connector (not specifically shown in FIG. 3), umbilical or universal cord 32, control body or endoscope handle 31, and insertion tube 33 with internal channels (suction channel 34, air channel 35, water channel 36, and water-jet channel 37). At the distal end of the insertion tube 33 is the nozzle 33A that is inside the patient. The suction channel 34 has at its proximal end a suction connector 34A and on the endoscope handle 31 a suction valve 34B. At the proximal end of the endoscopes 30, the air channel 35 has an air pipe connector 35A, the water channel 36 has a water bottle connector 36A, and the water-jet channel 37 has a water-jet connector 37A. On the endoscope handle 31 a biopsy valve 38 and an air/water valve 39 are present. The endoscope different systems include the air and water system, the suction and operating channel system, the mechanical system, the endoscopic retrograde cholangiopancreatography (ERCP) elevator system, the optical system, and the electrical system.

Even though endoscopes represent a valuable diagnostic and therapeutic tool in modern medicine and the incidence of infection associated with their use reportedly is low, lately more healthcare—associated outbreaks have been linked to contaminated endoscopes than to any other medical device. Infections suspected to have occurred after lapses in reprocessing of duodenoscopes were related to failure to use appropriate attachments to specialty channels or failure to clean all channels during reprocessing. Patient-to-patient transmission of carbapenem-resistant Enterobacteriaceae or other multidrug-resistant organisms by contaminated duodenoscopes, despite appropriate and optimal reprocessing, has been reported all of the world and resulted in patients' deaths. Some of these devices cannot be steam sterilized because they are heat-sensitive. Additionally, sterilization using ethylene oxide (EtO) can be too time-consuming for routine use in between patients. Other new technologies, such as hydrogen peroxide gas plasma and peracetic acid reprocessors, provide faster cycle times. However, evidence that sterilization of these items improves patient care by reducing the infection risk is lacking. Many newer models of these instruments can withstand steam sterilization, which for critical items is the preferred method.

Flexible endoscopes, because of the types of body cavities they enter, may acquire high levels of microbial contamination (bioburden) during each use. To prevent the spread of health-care-associated infections, all heat-sensitive endoscopes (e.g., gastrointestinal endoscopes, bronchoscopes, nasopharygoscopes) must be properly cleaned and, at a minimum, subjected to high-level disinfection after each use. High-level disinfection can be expected to destroy all microorganisms, although when high numbers of bacterial spores are present, a few spores might survive.

In general, during the manual reprocessing of the endoscopes (see FIG. 3), it is needed to meticulously clean the entire endoscope, including valves (suction valve 34B, biopsy valve 38, and air/water valve 39), channels (suction channel 34, air channel 35, water channel 36, and water-jet channel 37), connectors (suction connector 34A, air pipe connector 35A, water bottle connector 36A, and water-jet connector 37A) and all detachable parts using only specific cleaning and disinfection devices (such as brushes) designed for the endoscope model being cleaned. The flushing and brushing of all accessible channels are mandatory to remove all organic (e.g., blood or tissue) and other residues. To facilitate access to all surfaces, the valves (suction valve 34B, biopsy valve 38, and air/water valve 39) during cleaning must be repeatedly actuated. The cleaning of the external surfaces and components of the endoscope is done using a soft cloth, a sponge, or brushes. If enzymatic detergents are used, they need to be discarded after each use, since these products are not microbicidal and will not retard microbial growth. During high-level disinfection the channels of the endoscopes (suction channel 34, air channel 35, water channel 36, and water-jet channel 37), the access connectors (suction connector 34A, air pipe connector 35A, water bottle connector 36A, and water-jet connector 37A), and valves (suction valve 34B, biopsy valve 38, and air/water valve 39) are repeatedly flushed and cleaned with specialized biocides that are recommended by Food and Drug Administration (FDA), Centers for Disease Control and Prevention (CDC), or different manufacturers.

Automated endoscope reprocessors offer several advantages over manual reprocessing. They automate and standardize several important reprocessing steps, reduce the likelihood that an essential reprocessing step will be skipped, and reduce personnel exposure to high-level disinfectants or chemical sterilants. Establishment of correct connectors between the reprocessor and the endoscope is critical to ensure complete flow of disinfectants and rinse water. Also, selection of the proper cleaning and high-level disinfection cycle based on the type of endoscope is crucial for a proper reprocessing.

Due to the types of body's cavities that are serviced by flexible endoscopes 30, they acquire high levels of microbial contamination (bioburden) during each use. The same is happening with reusable contaminated medical tubing 30 (see FIG. 9) from ventilators or from dialysis machines that can get contaminated from breathing and from blood, respectively. Endoscopes 30 are frequently contaminated with blood, particularly when a biopsy is taken. Flexible endoscopes 30 are also exposed to other soils, which vary based upon the part of the body where the scope is use (i.e., fecal matter in a colonoscope).

Research has shown that bioburden left on instruments interferes with the sterilization process and can render it ineffective. Making sure an endoscope 30 is as clean as possible is thus paramount to preventing cross contamination of any patient undergoing a procedure. Ensuring cleanliness of endoscopes 30 should be part of any hospital's infection control program. Cleaning should be monitored since it is directly correlated to reducing hospital-acquired infections. Failure to completely dissemble, clean, and high-level disinfect endoscopes parts has led to infections in patients.

As with antibiotics, reduced susceptibility (or acquired "resistance") of bacteria to disinfectants can arise by either chromosomal gene mutation or acquisition of genetic material in the form of plasmids or transposons. When changes occur in bacterial susceptibility that renders an antibiotic ineffective against an infection previously treatable by that antibiotic, the bacteria are referred to as "resistant." The rotational use of disinfectants in some environments (e.g., pharmacy production units) has been recommended and practiced in an attempt to prevent development of resistant microbes.

Contaminated disinfectants and antiseptics have been occasional vehicles of health-care infections and pseudo-epidemics for more than 50 years. Published reports describing contaminated disinfectants and antiseptic solutions leading to health-care-associated infections have shown that members of the genus Pseudomonas (e.g., P. aeruginosa) are the most frequent isolates from contaminated disinfectants—recovered from 80% of contaminated products. Their ability to remain viable or grow in use-dilutions of disinfectants is unparalleled. This survival advantage for Pseudomonas results presumably from their nutritional versatility, their unique outer membrane that constitutes an effective barrier to the passage of germicides, and/or efflux systems. Although the concentrated solutions of the disinfectants have not been demonstrated to be contaminated at the point of manufacture, an undiluted phenolic can be contaminated by Pseudomonas spores during use. In the illness associated with contaminated disinfectants, the product was used to disinfect patient-care equipment, such as endoscopes, cystoscopes, or reusable contaminated tubing from ventilators and dialysis systems, to name a few. Germicides used as disinfectants that were reported to have been contaminated include chlorhexidine, quaternary ammonium compounds, phenolics, and pine oil.

Outbreaks involving removable endoscope parts such as suction valves and endoscopic accessories designed to be inserted through flexible endoscopes such as biopsy forceps emphasize the importance of cleaning to remove all foreign matter before high-level disinfection or sterilization.

To summarize, endoscope disinfection or sterilization with a liquid chemical sterilant involves five steps after leak testing:

1) Clean—mechanically clean internal and external surfaces, including brushing internal channels (suction channel 34, air channel 35, water channel 36, and water-jet channel 37) and flushing each internal channel with water and a detergent or enzymatic cleaner (leak testing is recommended for endoscopes before immersion).
2) Disinfect—immerse endoscope 30 in high-level disinfectant (or chemical sterilant) and perfuse (eliminates air pockets and ensures contact of the germicide with the internal channels) disinfectant into all accessible channels (suction channel 34, air channel 35, water channel 36, and water-jet channel 37), and expose for a time recommended for specific products.
3) Rinse—rinse the endoscope 30 and all channels (suction channel 34, air channel 35, water channel 36, and water-jet channel 37) with sterile water, filtered water (commonly used with automated endoscope reprocessors) or tap water (i.e., high-quality potable water that meets federal clean water standards at the point of use).
4) Dry—rinse the insertion tube 33 and inner channels (suction channel 34, air channel 35, water channel 36, and water-jet channel 37) with alcohol, and dry with forced air after disinfection and before storage.
5) Store—store the endoscope 30 in a way that prevents recontamination and promotes drying (e.g., hung vertically).

For cleaning and high-level disinfection of endoscopes, arthroscopes, laparoscopes, bronchoscopes, nasopharygoscopes, duodenoscopes, cystoscopes, ventilators, respirators, hemodialysis units, as an alternative effective method or in combination with other methods, is the use of extracorporeal focused acoustic pressure shockwaves and special pressure waves (planar, pseudo-planar, radial, or unfocused waves) or low-frequency ultrasound. A significant advantage of using shockwaves or pressure waves or low-frequency ultrasound, when compared with existing disinfectants/biocides, is that their effect is based only on mechanical action produced by the compressive and tensile phases that are generated during the time the shockwaves or pressure waves or ultrasound waves pass through the area/zone of interest.

Thus, the focused acoustic pressure shockwaves or pressure waves or low frequency ultrasound produced by the proposed embodiments will have a compressive phase (produces compressive pressures) and a tensile phase (negative pressures that produce cavitation bubbles, which collapse with high-speed jets) during one cycle of the focused acoustic pressure shockwaves or pressure waves or ultrasound waves. These two synergetic effects, work in tandem, by acting at macro (compressive phase) and micro level (cavitation jets of the tensile phase), which is enhancing the effects of the focused acoustic pressure shockwaves or pressure waves or low frequency ultrasound waves on biofilms or soiling or directly on different pathogens present in reusable contaminated equipment and their sub-assemblies or parts.

In lithotripsy, kidney stone fragmentation using focused shockwaves, cavitation is believed to be the primary cause of stone disintegration. Based on the same principle the biofilms can be obliterated and dislodged from external or internal surfaces of different medical devices or systems, as confirmed by experimental results. In general, the focused acoustic pressure shockwaves or pressure waves (planar, pseudo-planar, radial, or unfocused waves) or low-frequency ultrasound are highly controlled to generate an energy amount fitted for the purpose of a specific application. This is accomplished based on reflector geometry and its material (for shockwaves and pressure waves), energy setting (input energy level of the focused acoustic pressure shockwaves or pressure waves or ultrasound), number of focused acoustic pressure shockwaves or pressure waves (planar, pseudo-planar, radial, or unfocused waves) or the treatment duration for low-frequency ultrasound, and finally by their frequency per second that dictates the total acoustic energy delivered during the cleaning and high-level disinfection of endoscopes, arthroscopes, laparoscopes, bronchoscopes, nasopharygoscopes, duodenoscopes, cystoscopes, ventilators, respirators, hemodialysis units, or any reusable contaminated medical systems or their parts. Reflector geometry directly controls the delivery of the shockwaves (focused or unfocused) or pressure waves into the targeted region and shapes their spatial distribution in the same targeted region. The energy setting is the energy input to generate focused acoustic pressure shockwave 40 or pressure waves (acoustic planar pressure wave 374 or pseudo-planar pressure wave 40 or acoustic radial pressure wave 40) and low-frequency ultrasound waves 380 and 381, as described in FIGS. 4, 5, 6, 37, 38A and 38B. The energy setting is directly affecting the pressure output into the targeted region/zone and together with the number of shockwaves/pressure waves and their frequency per second, or the frequency setting and treatment duration for ultrasound, determine the total amount of energy deposited inside the targeted region.

The peak positive compressive pressures of the focused acoustic pressure shockwave 40 or pressure waves (acoustic planar pressure wave 374 or pseudo-planar pressure wave 40 or acoustic radial pressure wave 40) and low-frequency ultrasound waves 380 and 381 are concentrated to a specifically localized region, as can be seen from FIGS. 4, 5, 6, 37, 38A and 38B, causing a disruption, movement or stretching of different organic or non-organic materials in the targeted region at amplitudes depending on the structure of each material/substance. This mechanical vibration combined with the microjets produced by the collapse of the cavitational bubbles, can produce in a liquid acoustic streaming and micro-streaming that can contribute to the dislodging and integrity destruction of individual bacteria, viruses, micro-organisms or organized structures as biofilms from the tubing walls of the endoscopes, arthroscopes, laparoscopes, bronchoscopes, nasopharygoscopes, duodenoscopes, cystoscopes, ventilators, respirators, or hemodialysis units. Furthermore, localized/transient thermal effects created during collapse of the cavitation bubbles can also kill bacteria and viruses.

The focused acoustic pressure shockwave 40 or pressure waves (acoustic planar pressure wave 374 or pseudo-planar pressure wave 40 or acoustic radial pressure wave 40) and low-frequency ultrasound waves 380 and 381 can also generate free radicals in a fluid that have a potential destructive effect on bacteria, viruses or biofilms. Thus, focused acoustic pressure shockwave 40 or pressure waves (acoustic planar pressure wave 374 or pseudo-planar pressure wave 40 or acoustic radial pressure wave 40) and low-frequency ultrasound waves 380 and 381 can destroy bacteria, viruses, and various other micro-organisms, by affecting their membrane integrity. For viruses their external shell integrity can be compromised due to the penetrating forces generated by the micro-jets produced by the collapse of cavitational bubbles formed in the tensile phase by the negative pressures. This effect is also combined with the transient high temperatures produced during cavitational bubbles collapse, which can denature the virus and its DNA material. Most important, in these mechanisms of action of the focused acoustic pressure shockwave 40 or pressure waves (acoustic planar pressure wave 374 or pseudo-planar pressure wave 40 or acoustic radial pressure wave 40) and low-frequency ultrasound waves 380 and 381, there is no biochemical process involved that can produce mutations. Thus, there is no developed resistance of bacteria or viruses to the focused acoustic pressure shockwave 40 or pressure waves (acoustic planar pressure wave 374 or pseudo-planar pressure wave 40 or acoustic radial pressure wave 40) and low-frequency ultrasound waves 380 and 381, due to their mutation, natural selection, transformation, transduction or conjugation. This can constitute a significant advantage when compared to different chemicals and biocides, which in time triggers pathogen mutations and resistance.

Figure 4:
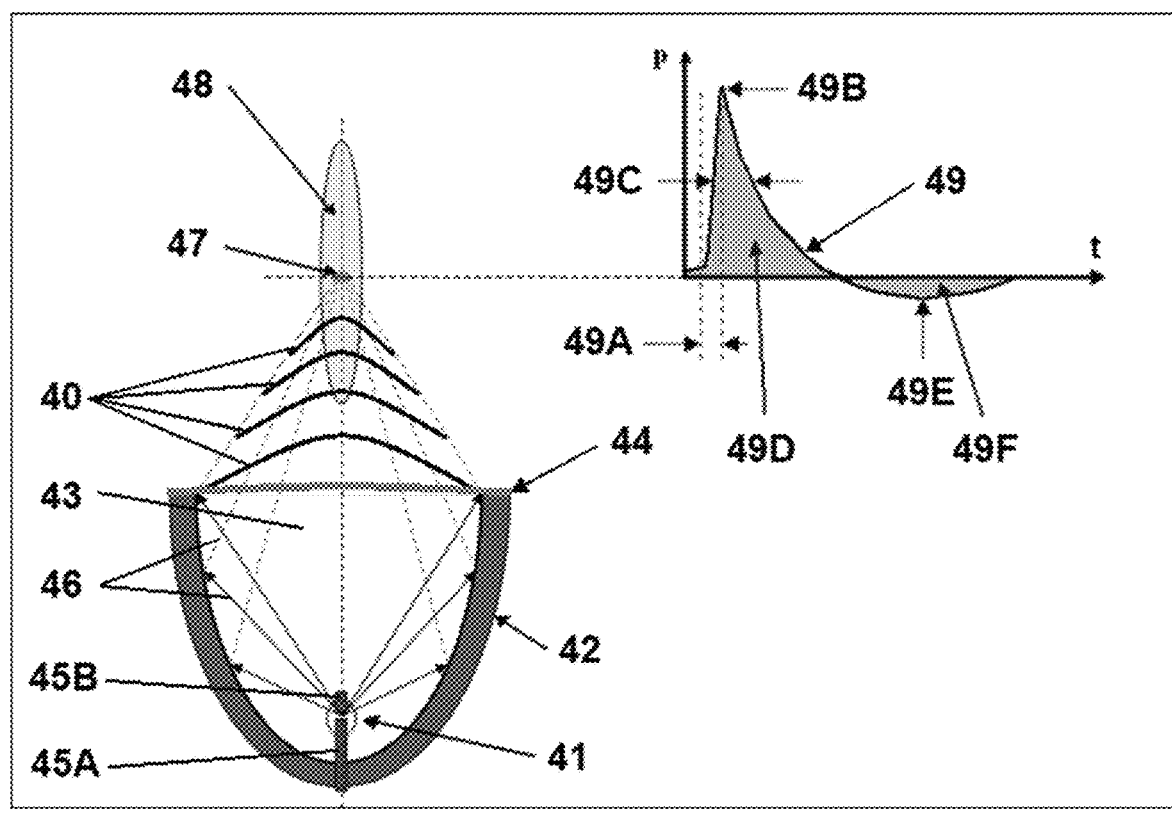
FIG. 4 is a schematic representation of features characteristic for focused pressure shockwaves known in the prior art.

The high mechanical tension and pressures found at the front of the focused acoustic pressure shockwave distinguishes them from other kinds of sound waves, such as ultrasonic waves or pressure waves. FIG. 4 presents the main and unique characteristics for the focused acoustic pressure shockwave 40, which are the same regardless of the principle used to generate them. In the specific case described in FIG. 4, the shockwaves are produced via the spark-gap electrohydraulic principle. To focus shockwaves, it is necessary to produce them in one point and then focus the shockwaves towards another point where their action is needed. The only geometry that has two focal points is the ellipse and in three-dimensional realm is the ellipsoid (see FIGS. 7, 30 and 31), which is the geometry used for the reflector 42 (in other embodiments the reflector 42 may have other geometries besides elliptical, such as parabolic and combination semi-spherical and conical). However, for the medical field the second focal point $F_2$ of the ellipsoidal geometry must coincide with the tissue being treated or the region where the shockwaves' action is needed, which means that only a semi-ellipsoidal reflector 42 and not full ellipsoid can be used, as clearly depicted in FIGS. 4, 8, 9, 12, 17, 19, 20B, 21B, 22, and 27). Thus, the focused acoustic pressure shockwave 40 are produced via discharging a high voltage in the fluid-filled reflector cavity 43 and in between the first electrode 45A and second electrode 45B of the spark-gap 41, which is placed in first focal point $F_1$ (FIGS. 7 and 8) of the semi-ellipsoidal reflector 42. The high voltage discharge produces an oscillating plasma bubble that creates kinetic energy in the fluid present in the fluid-filled reflector cavity 43. This high kinetic energy is in fact the shockwave that is then reflected by the semi-ellipsoidal reflector 42 towards the second focal point 47 ($F_2$ from FIGS. 7, 8, 9, and 12). The shockwave focusing 46 is done towards a focal volume 48 that is centered around the focal point 47 ($F_2$ of the ellipsoidal geometry). To keep the fluid inside the fluid-filled reflector cavity 43, a coupling membrane 44 is used that stays on top of the opening/aperture of the semi-ellipsoidal reflector 42. In the focal volume 48, produced by the focused acoustic pressure shockwave 40, there is a special pressure "P" profile function of time "t" that defines the shockwave pressure signal 49. Thus, there is a sharp increase in positive/compressive pressure to the maximum shockwave positive pressure 49B of the shockwave compressive phase 49D, which is defined by a rise time 49A in the range of tens of nano seconds to hundreds of nano seconds. After the positive pressure is reaching the maximum shockwave positive pressure 49B, then the pressure decreases exponentially towards zero, which completely defines the full shockwave compressive phase 49D of the shockwave pressure signal 49. The pulse width 49C is defined as the time interval beginning at the first time the positive pressure exceeds 50% of the maximum shockwave positive pressure 49B. The larger the pulse width 49C, the larger and more powerful is the shockwave compressive phase 49D and its influence on the endoscopes or reusable contaminated tubing from ventilators and dialysis machines or from any other medical devices, to produce biofilms and soil dislodging, and elimination of infectious pathogens. Once the pressures are in the negative values, they are in the shockwave tensile phase 49F. After reaching the maximum shockwave negative pressure 49E, the pressure is going back towards zero to completely outline the shockwave tensile phase 49F profile and also define the end of the focused shockwave pressure signal 49. During the shockwave tensile phase 49F that is characterized by negative pressures, cavitation bubbles can be generated in fluids. The cavitation bubbles are gas voids in fluids that grow as long as the energy is delivered to the bubble. This energy is released from the bubble during its collapse (implosion) in the form of high-speed pressure micro jets and localized/transient high temperature. The micro jets and elevated temperature are present within the shockwave tensile phase 49F and are transient in nature. The compressive pressures, the high-speed pressure micro jets, and localized/transient high temperature occur with each shockwave pulse and all of them are contributing to the cleaning and high-level disinfection process. The total time duration of a shockwave pressure signal 49 is in between five to eight microseconds, which defines a strong and rapid pressure variation, that produces significant, controlled, and efficient effects during the cleaning and high-level disinfection of the endoscopes or reusable contaminated tubing from ventilators and dialysis machines, to name a few.

Figure 5:
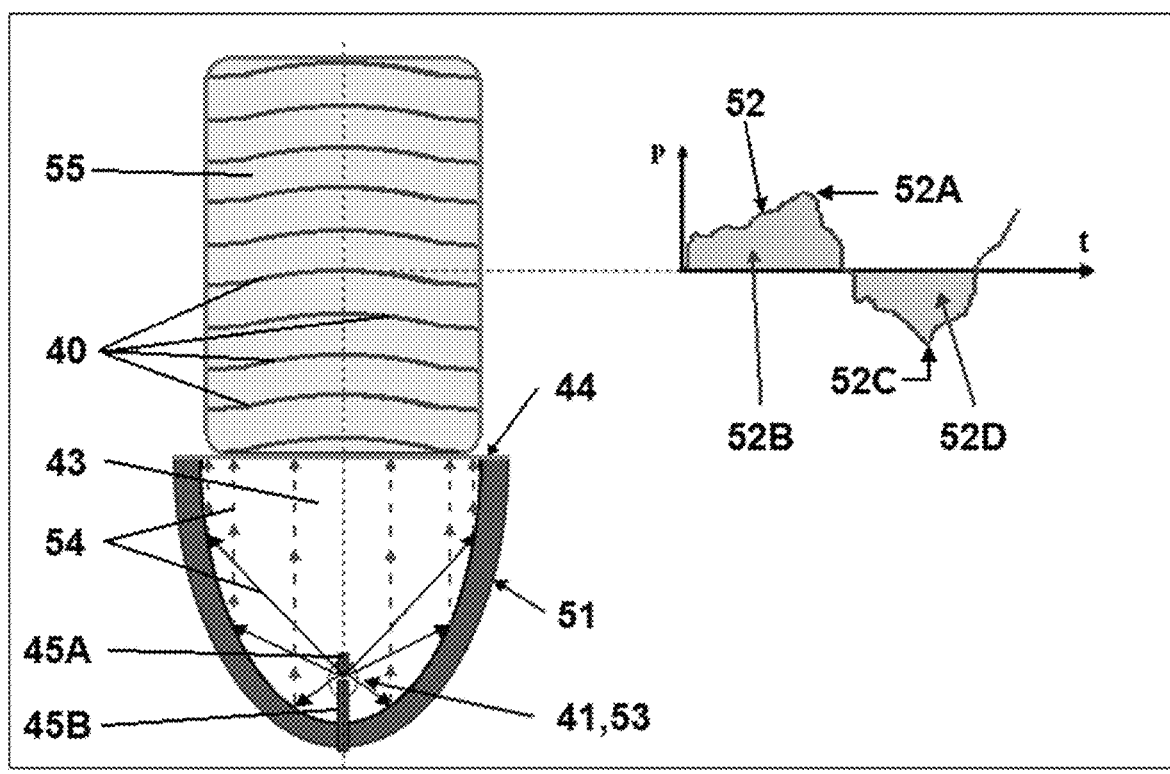
FIG. 5 is a schematic representation of features characteristic for planar pressure waves known in the prior art.
Figure 6:
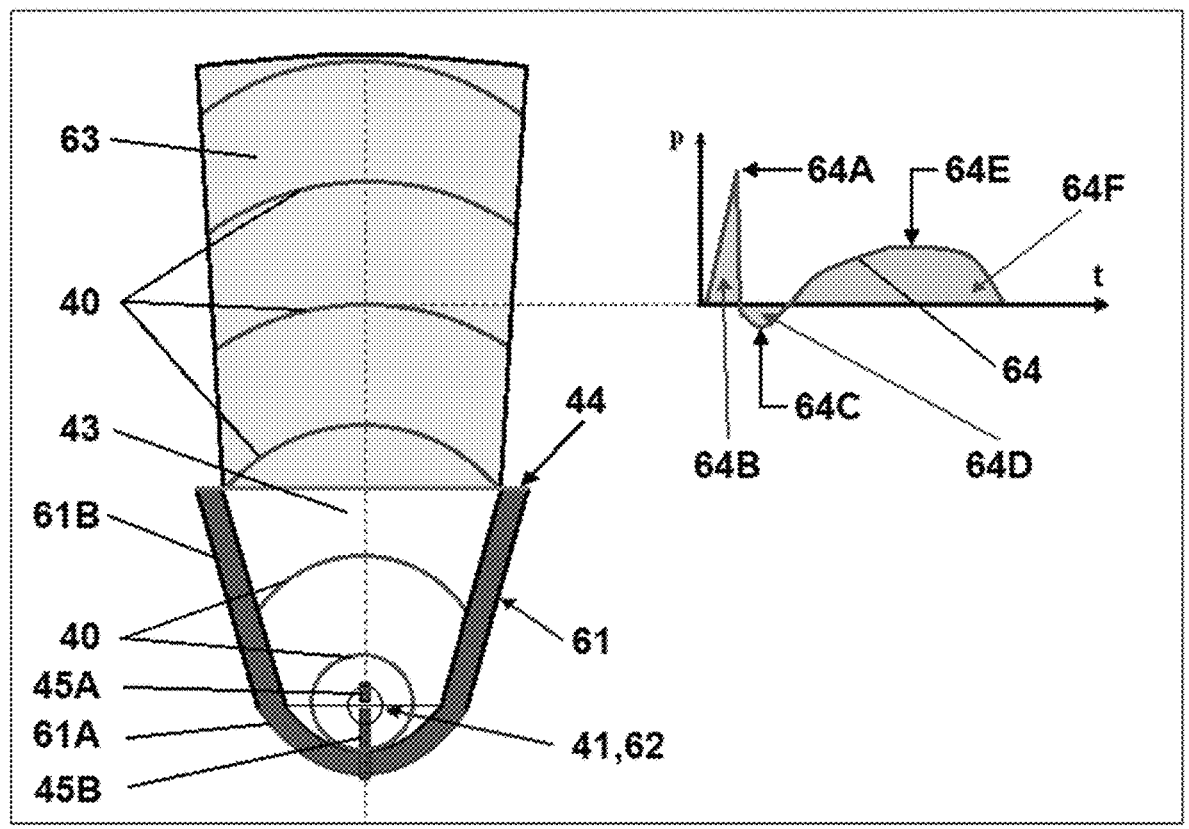
FIG. 6 is a schematic representation of features characteristic for radial pressure waves known in the prior art.
Figure 11:
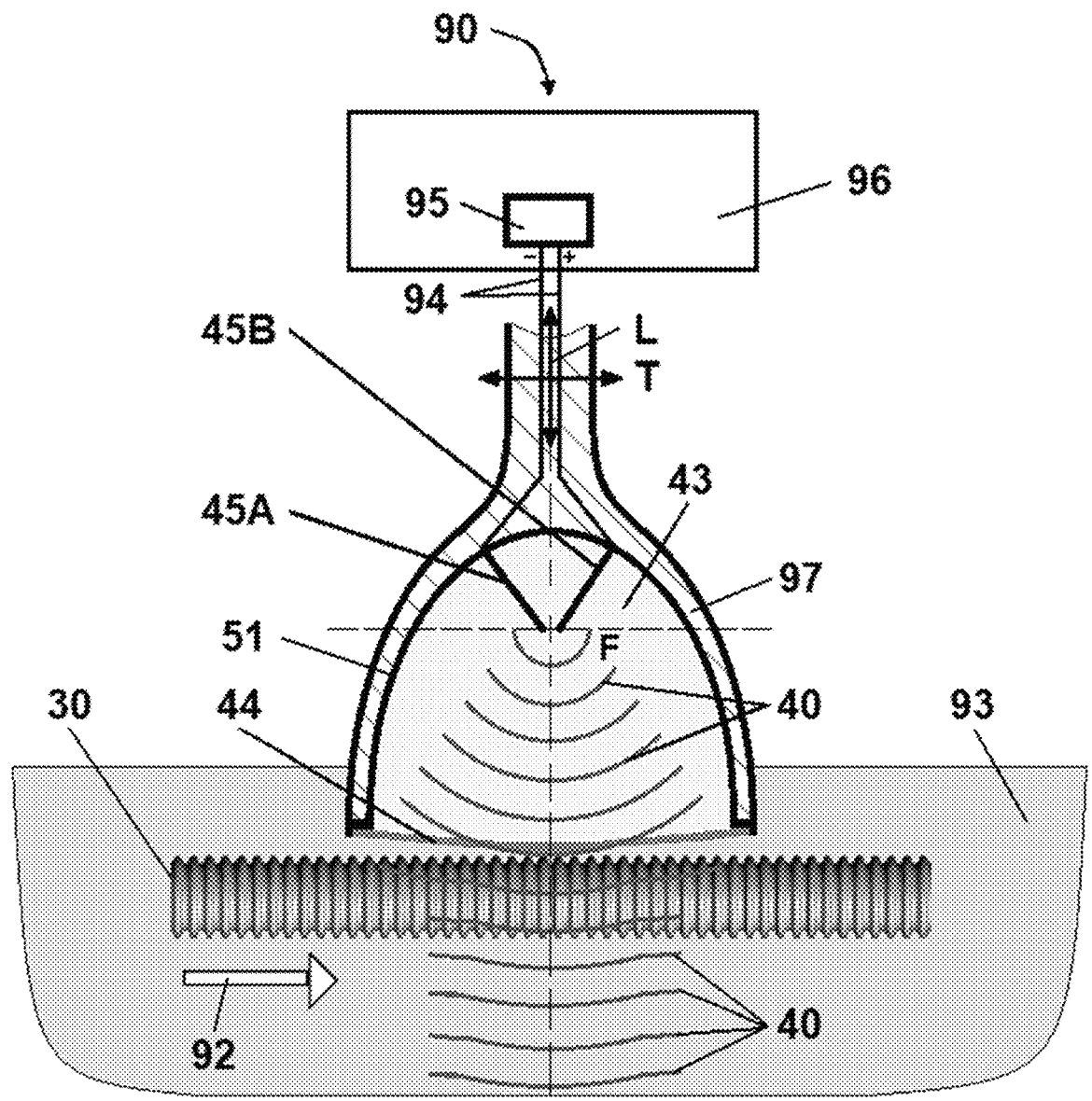
FIG. 11 is a schematic representation of an electrohydraulic pseudo-planar pressure waves system for cleaning and high-level disinfection of endoscopes or reusable tubing from ventilators and dialysis machines and other medical devices in one embodiment of the present invention.

Focused acoustic pressure shockwave 40 are more powerful in general and deposit more energy in the targeted tissue when compared to pressure waves, which are having a pressure signal flatter and more sinusoidal in shape for acoustic planar pressure wave 374 (FIG. 37) or pseudo-planar pressure wave 40 (slightly distorted planar waves), as presented in FIGS. 5 and 11, and distorted tooth-shape followed by a large positive pressures region for acoustic radial pressure wave 40, as seen in FIG. 6. Due to lower positive pressures and smaller values for negative pressures for the acoustic planar pressure wave 374 or pseudo-planar pressure wave 40 or acoustic radial pressure wave 40, such pressure waves will put less energy inside the targeted zone for cleaning and high-level disinfection, when compared to focused acoustic pressure shockwave 40. However, the acoustic planar pressure wave 374 or pseudo-planar pressure wave 40 or acoustic radial pressure wave 40 can cover a larger area of action, which can be advantageous in some situation where a shorter time for the cleaning and high-level disinfection is paramount.

The reflectors used to create pseudo-planar pressure wave 40 are parabolic reflectors 42 characterized by only one focal point known as parabolic focal point (F), which in this situation is inside parabolic reflector 51 as presented in FIGS. 5 and 11. The pressure waves are generated by the high voltage discharge in between the first electrode 45A and second electrode 45B of the spark-gap 41 placed in the parabolic focal point (F), as presented in FIGS. 5 and 11. The high voltage discharge produces an oscillating plasma bubble that creates kinetic energy in the fluid-filled reflector cavity 43, which actually generates the pressure waves. To keep the fluid inside the fluid-filled reflector cavity 43 a coupling membrane 44 is used that stays on top of the opening/aperture of the parabolic reflector 51. These pressure waves are moving radially from the parabolic focal point (F) in the form of acoustic radial pressure wave 40 (see FIG. 11) towards the parabolic reflectors 51, which produces the pressure waves reflection 54 parallel to its longitudinal axis (similar to a flash light) and thus creating outside the reflector 51, the pseudo-planar pressure waves 40 inside the pseudo-planar waves pressure field 55 that overlaps with the targeted zone for cleaning and high-level disinfection. In some cases, clean acoustic planar pressure waves 374 are created using planar piezoelectric crystals or piezo-fibers as presented in FIG. 37. For the acoustic planar pressure waves 374 there is no reflection involved (no reflectors needed). Since the acoustic planar pressure wave 374 or pseudo-planar pressure wave 40 are almost identical in their action and the pressure signal shape generated in the targeted action zone, they will be described together as a bundle. Thus, the acoustic planar pressure wave 374 (FIG. 37) or pseudo-planar pressure wave 40 (FIGS. 5 and 11) are characterized by almost equal maximum planar/pseudo-planar wave positive pressure 52A and maximum planar/pseudo-planar wave negative pressure 52C in absolute values, which makes the planar/pseudo-planar wave pressure signal 52 from the pseudo-planar waves pressure field 55 to have nearly a sinusoidal shape/variation for pressure "P" versus time "t". This also means that the planar/pseudo-planar wave compressive phase 52B and the planar/pseudo-planar wave tensile phase 52D have similar energy incorporated in them (given by the area in between the curve and time axis).

The wave form of the acoustic radial pressure waves 40 is presented in FIG. 6. In general, the acoustic radial pressure waves 40 have a duration (more than one thousand microseconds), which is more than 100 times longer when compared to focused acoustic pressure shockwave 40 (less than ten microseconds, or more precise in between five to eight microseconds). When using the electrohydraulic principle to generate the acoustic radial pressure waves 40, a high voltage discharge in between the first electrode 45A and second electrode 45B of the spark-gap 41 is produced in the sphere central point of the combination semi-spherical and conical reflector 61. The high voltage discharge produces an oscillating plasma bubble that creates kinetic energy in the fluid-filled reflector cavity 43. To keep the fluid inside the fluid-filled reflector cavity 43 a coupling membrane 44 is used that stays on top of the opening/aperture of the combination semi-spherical and conical reflector 61. To not impede with the propagation of the acoustic radial pressure waves 40 generated in the sphere central point, the combination semi-spherical and conical reflector 61 has a conical reflector portion 61B towards its mouth. The semi-spherical reflector portion 61A reflects the acoustic radial pressure waves 40 (propagating towards the bottom of the combination semi-spherical and conical reflector 61) back towards the sphere central point. That means that they are not contributing to the acoustic radial pressure waves 40 present in the radial waves pressure field 63 that overlaps with the targeted zone for cleaning and high-level disinfection of medical systems, as endoscopes 30, or parts, as reusable contaminated tubing 30 (see FIG. 9) from ventilators and dialysis machines or from any other medical devices, or valves, or connectors, etc. However, the reflected portion of the acoustic radial pressure waves 40 from the bottom of the combination semi-spherical and conical reflector 61 towards the sphere central point will collapse any residual bubbles left in the spark-gap 41 area from the plasma bubble generated by the high voltage discharge in the fluid-filled reflector cavity 43, which will allow the subsequent acoustic radial pressure waves 40 to be generated into a pretty consistent way. In the radial waves pressure field 63, the acoustic radial pressure waves 40 are characterized by a radial wave pressure signal 64 that has distorted tooth-shape followed by a large positive pressure region. Thus, there is a sharp increase in positive/compressive pressure to the maximum radial wave positive pressure 64A of the radial wave compressive phase 64B. After the positive pressure is reaching the maximum radial wave positive pressure 64A, then the pressure decreases almost instantaneous towards zero, which completely defines the full radial wave compressive phase 64B of the radial wave pressure signal 64. Once the pressures are in the negative values, they are in the radial wave tensile phase 64D. After reaching the maximum radial wave negative pressure 64C, the pressure is going back towards zero to completely outline the radial wave tensile phase 64D profile. However, the pressures continue to increase and become positive again and reach maximum remnant positive pressure 64E, which is smaller when compared to the maximum radial wave positive pressure 64A. After the positive pressure is reaching the maximum remnant positive pressure 64E, then the pressure decreases slowly towards zero, which completely defines the full remnant positive pressure phase 64F and the end of the radial wave pressure signal 64. The positive pressure phase 64F incorporates a significant portion of the radial wave pressure signal 64 and also collapses prematurely the cavitation bubbles generated in the radial wave tensile phase 64D, which means that the role played by cavitation is reduced when compared to the focused acoustic pressure shockwave 40 and pseudo-planar pressure wave 40. However, some cavitation is still produced and the double positive pressures (maximum radial wave positive pressure 64A and maximum remnant positive pressure 64E) are enhancing the removal of soiling, such as included contaminating particulates and particulate matter, planktonic bacteria, virus spores, fungi, and biofilms from the endoscopes or reusable contaminated tubing from respirators or hemodialysis units or any other medical devices or their parts that requires reprocessing for cleaning and high-level disinfection.

Figure 38A:
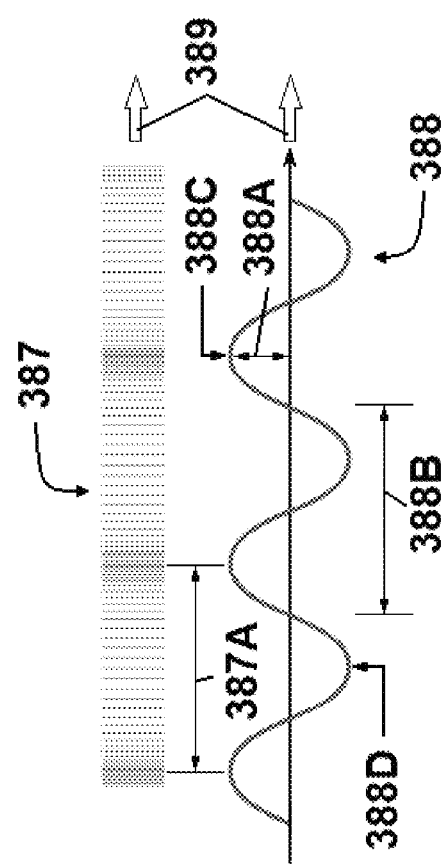
FIG. 38A is a schematic representation of features characteristic for ultrasound pressure waves known in the prior art.
Figure 38B:
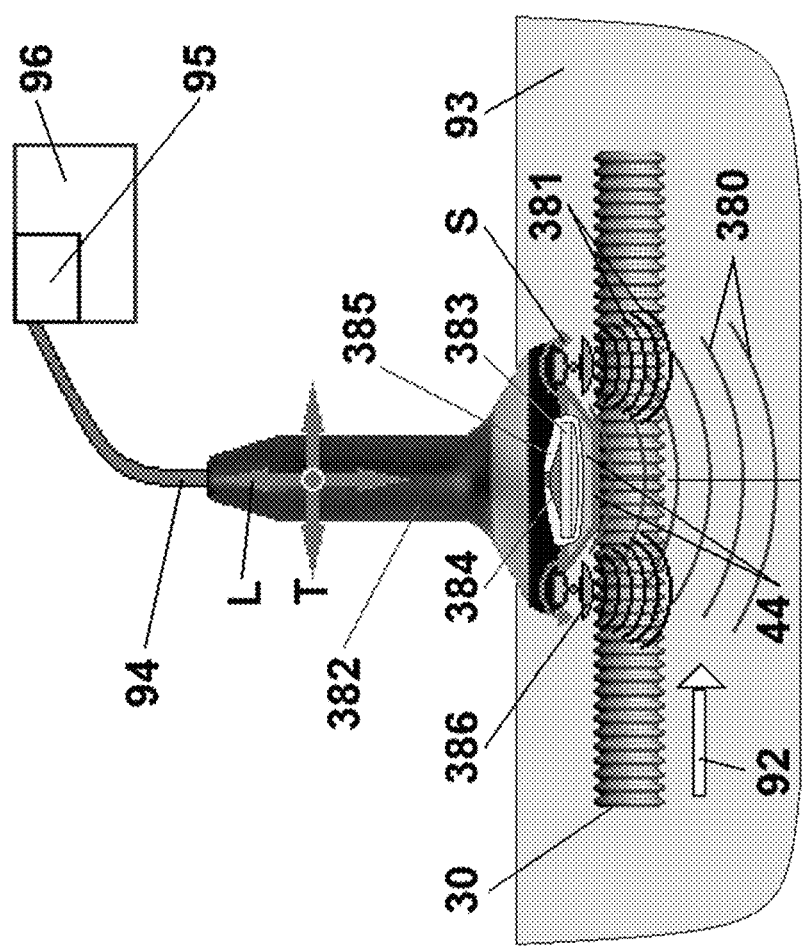
FIG. 38B is a schematic representation of an ultrasonic system producing multiple low frequency ultrasound waves for cleaning and high-level disinfection of endoscopes and reusable tubing from ventilators and dialysis machines and other medical devices, according to one embodiment of the present invention.

FIG. 38A presents the wave form of the main ultrasound waves 380 or secondary ultrasound waves 381 seen in FIG. 38B. In general, the ultrasound waves 380 or 381 have two components. The ultrasound longitudinal wave 387 is the one moving in the ultrasound direction of propagation 389. Adjacent layers of fluid are subjected to a cyclic compression and expansion with velocity dependent on propagation media (liquid, air or solid). Coexisting with the ultrasound longitudinal wave 387 is the ultrasound transversal wave 388, which is a low velocity and high damping wave with a sinusoidal variation in a direction perpendicular to the ultrasound direction of propagation 389. Usually, the ultrasound transversal wave 388 can produce friction in propagation media and consequently possible heat. However, the low-frequency ultrasound has a large ultrasound wavelength 387A that is characterizing the ultrasound cycle 388B and this is why the effects of the ultrasound transversal wave 388 are less pronounced, which means that negligible or no heat is produced. Other important parameters that define the ultrasound waves 380 or 381 are the ultrasound maximum positive pressure 388C and ultrasound maximum negative pressure 388D, which are equal in absolute value that is also known as ultrasound amplitude 388A. The positive pressures 388C produce compressive forces/stresses and the negative pressure 388D generate cavitation bubbles. Due to continuous sequence of phases for ultrasound waves, the pressures are changing from positive pressures to negative pressures and then again to positive pressures in a sinusoidal variation, which has a significant influence on the cavitation. Thus, the cyclical acoustic wave of the ultrasound, make the cavitation bubbles to grow and then collapse due to incoming new positive pressures in a cyclical way too. In general, the ultrasound cavitation bubbles need many ultrasound cycles to reach a dimension that allow them to collapse by themselves. Usually, the ultrasound cavitation bubbles do not reach the same size as the shockwave cavitation bubbles, which translates in less energy generated during their collapse. Also, due to continuous oscillation in dimensions, the ultrasound cavitation bubbles accumulate heat and when finally reach the appropriate dimension they collapse as a hot spot, which can contribute together with the micro-jets generated during collapse to the contamination material dislodging from instruments surfaces and also to the pathogens killing.

In conclusion, as seen from FIGS. 4, 5, 6, 37, and 38A, the focused acoustic pressure shockwaves 40 behave similarly to other sound waves (acoustic planar pressure wave 374 or pseudo-planar pressure wave 40 or acoustic radial pressure wave 40 or ultrasound waves 380 and 381), with the main difference that the focused acoustic pressure shockwaves 40 possess more energy. A focused acoustic pressure shockwave 40 can travel larger distances easily (based on the amount of energy put in them at the point of origination), as long as the acoustic impedance of the medium remains the same. The same acoustic impedance principle is valid for pressure waves (acoustic planar pressure wave 374 or pseudo-planar pressure wave 40 or acoustic radial pressure wave 40) and low-frequency ultrasound waves 380 and 381, with the caviar that their energy is smaller when compared with focused acoustic pressure shockwaves 40 with consequences on their relatively limited traveling distance/penetration inside the targeted region. At the point where the acoustic impedance changes, energy is released and the focused acoustic pressure shockwaves 40 or pressure waves (acoustic planar pressure waves 374 or pseudo-planar pressure waves 40 or acoustic radial pressure waves 40) and low-frequency ultrasound waves 380 and 381 are reflected or transmitted with attenuation. Thus, the difference in between shockwaves and pressure waves or ultrasound is the amount of energy they deposit inside the targeted zone and sometimes their penetration inside the same targeted zone. Shockwaves are more powerful in general and have more energy due to their higher compressive pressures produced in the compressive phase and larger negative pressure from the tensile phase, which can produce more powerful cavitation bubbles in a fluid (see FIGS. 4, 5, 6, and 38A). On their turn, the pressure waves and low-frequency ultrasound are having a pressure signal flatter, more sinusoidal in shape, and due to their lower positive pressures and smaller values for negative pressures that influences the size of cavitation bubbles, they will put less energy inside the targeted zone. Sometimes this lower energy can be beneficial for specific applications where the targeted device, or system, or sub-component, or part have a more delicate construction.

Figure 7:
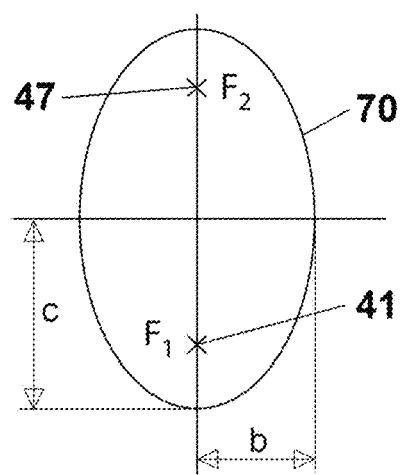
FIG. 7 is a schematic representation of typical ellipsoidal geometry that is used for focusing shockwaves known in the prior art.

FIG. 7 presents the typical ellipsoidal geometry that is used for focusing shockwaves. The ellipse 70 is the only geometry that has two focal points, which means that whatever is generated in the first focal point $F_1$ can be reflected and focused in the second focal point $F_2$. Based on this property, if a form of energy carrier is produced in $F_1$ via a high voltage discharge in a fluid using a spark-gap 41, it can be reflected and finally concentrated in the second focal point $F_2$, defined as the focal point 47. That is practically the way that focused acoustic pressure shockwaves 40 are generated and focused towards a targeted region that sits around the second focal point $F_2$. The elliptical geometry is characterized by the major elliptical semi axis "c", minor elliptical semi axis "b", and their ratio, which dictates the actual ellipse length and width, with significant implications on the reflective properties of a potential reflector with that specific geometry.

Figure 8:
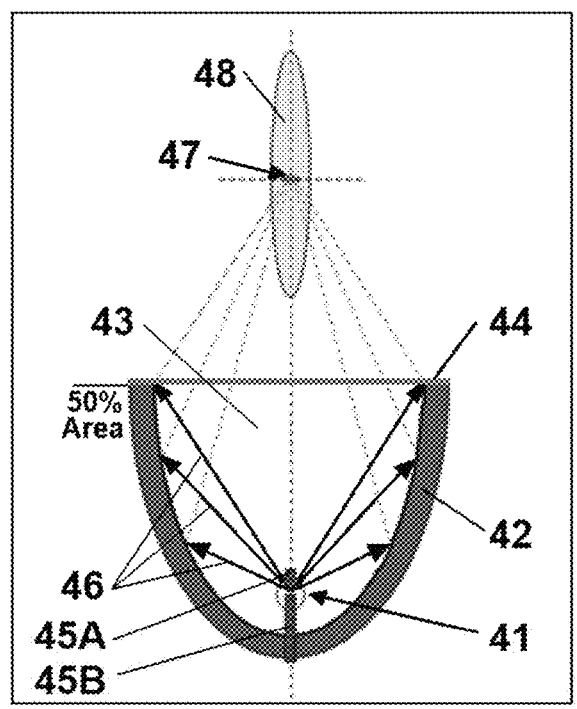
FIG. 8 is schematic representation of typical semi-ellipsoidal reflector used for focused shockwave applicators known in the prior art.

FIG. 8 is a geometric representation of the classic semi-ellipsoidal reflector 42, which is usually used to produce and reflect focused electrohydraulic shockwaves. Since the cleaning and high-level disinfection with focused acoustic pressure shockwaves 40 is produced in the focal volume 48 that encompasses the second focal point $F_2$ (defined as focal point 47), only a portion of the ellipsoidal geometry can be used for focusing. In most of the cases half of the ellipsoidal geometry can be used and those are the classic semi-ellipsoidal reflectors 42. When the endoscopes or reusable contaminated tubing from respirators or hemodialysis units or any other medical devices or their parts are placed before or after the focal volume 48, then the cleaning and high-level disinfection is produced by unfocused pressure waves. The semi-ellipsoidal reflector 42 can be shallow or deep, based on the ratio of the major elliptical semi axis "c" and minor elliptical semi axis "b". If the ration c/b is higher than 1.9 (c/b>1.9), then the semi-ellipsoidal reflector 42 is considered to be deep. With a ratio of 1.1≤c/b≤1.3 the semi-ellipsoidal reflector 42 is considered shallow and for 1.3<c/b≤1.9 is considered normal. The first focal point $F_1$ of the semi-ellipsoidal reflector 42 is where the shockwaves are generated via spark-gap 41 for the electrohydraulic principle that uses two electrodes (first electrode 45A and second electrode 45B) to produce a high voltage discharge in a fluid. The shockwave focusing 46 is done by the internal surface of the classic semi-ellipsoidal reflector 42 towards the focal point 47 (second focal point $F_2$) and the surrounded focal volume 48, as presented also in FIG. 4. To keep the fluid inside the fluid-filled reflector cavity 43 a coupling membrane 44 is used that stays on top of the opening/aperture of the semi-ellipsoidal reflector 42. These elements and construction presented in FIGS. 7 and 8 for the semi-ellipsoidal reflector 42 will be found in many of the embodiments presented in FIGS. 9, 12, 17A-17B, 19A-23, and 27.

Figure 12:
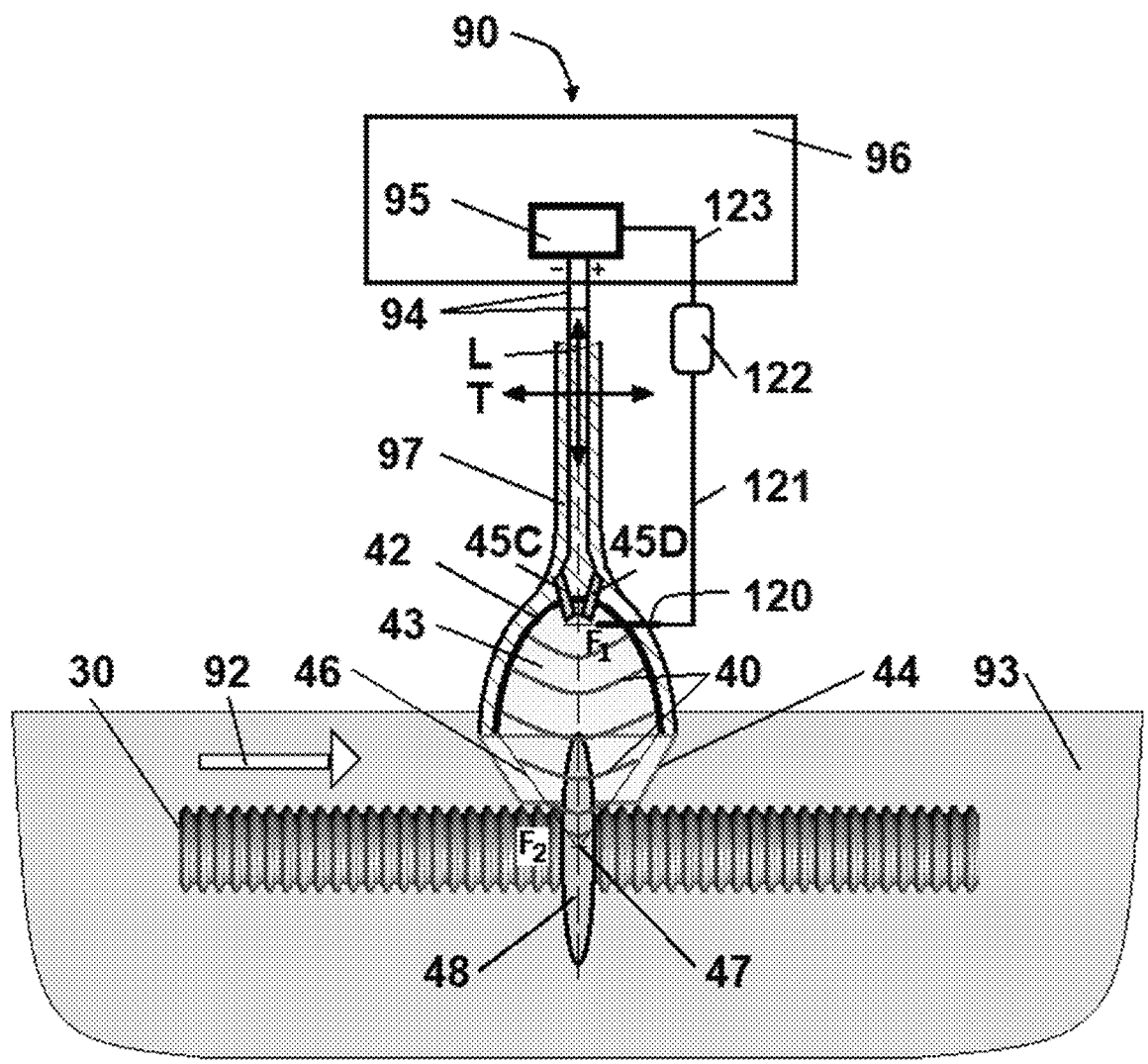
FIG. 12 is a schematic representation of a laser electrohydraulic focused shockwaves system for cleaning and high-level disinfection of endoscopes or reusable tubing from ventilators and dialysis machines and other medical devices in one embodiment of the present invention.
Figure 13:
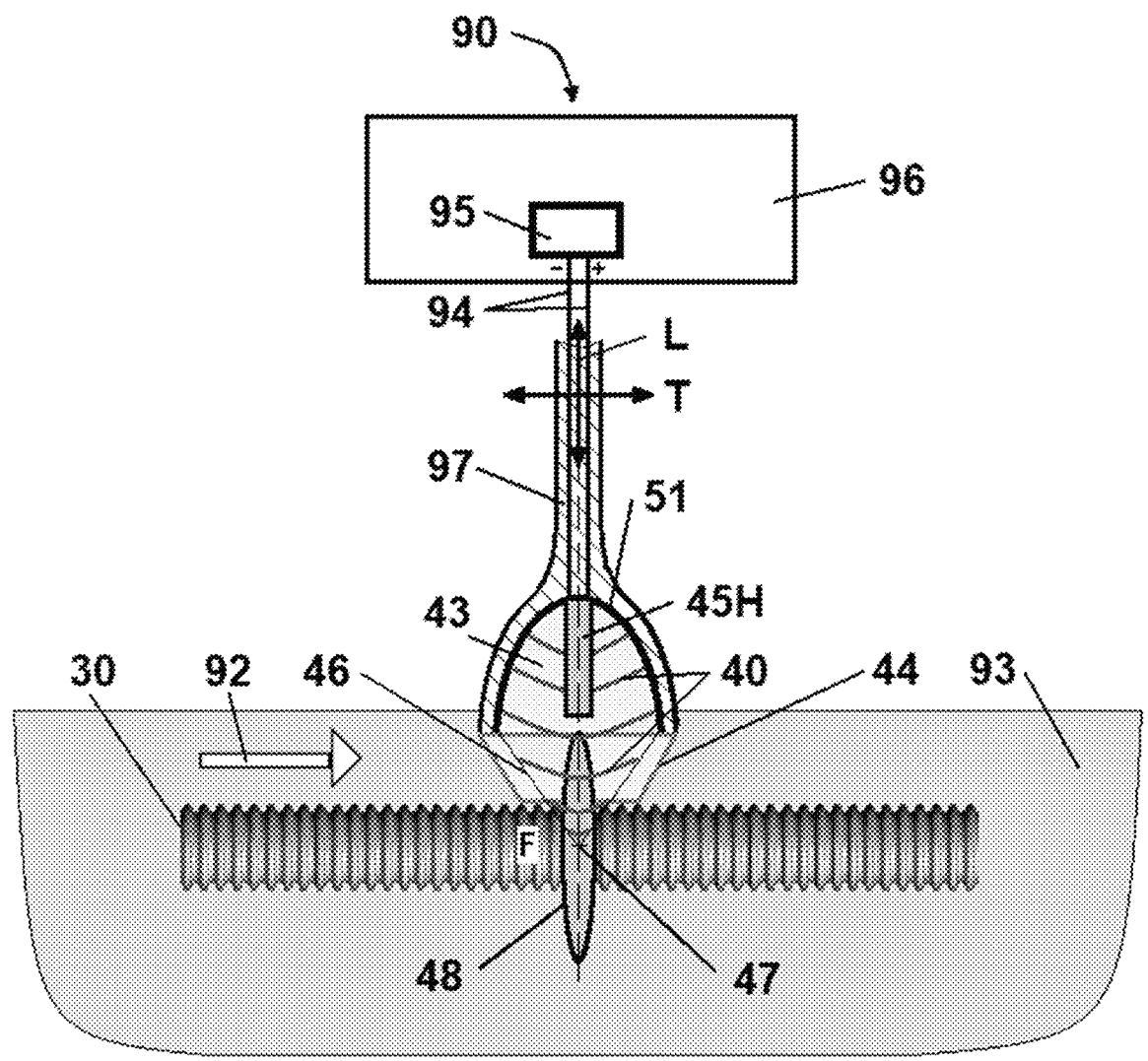
FIG. 13 is a schematic representation of a cylindrical coil-produced electromagnetic focused shockwaves system for cleaning and high-level disinfection of endoscopes or reusable tubing from ventilators and dialysis machines and other medical devices in one embodiment of the present invention.

It is an objective of the present inventions to provide different methods of generating focused shockwaves or special high-intensity pressure waves (planar, pseudo-planar, radial, or unfocused waves) or low-frequency ultrasound for cleaning and high-level disinfection of endoscopes or reusable contaminated tubing from ventilators and dialysis machines, or other reusable parts for medical systems, as follows:

- electrohydraulic generators using high voltage discharges (FIGS. 9-11, 17A-36, 39, and 41-46B)
- electrohydraulic generators using one or multiple laser sources (FIGS. 12, 23, and 40, and they can be also used with specific modifications for FIGS. 17A-36, and 41-46B)
- piezoelectric generators using piezo crystals/piezo ceramics (FIGS. 15, 37, and 38A-38B, and they can be also used with specific modifications for FIGS. 17A-36, and 41-46B)
- piezoelectric generators using piezo fibers (FIGS. 16, 37, 38A-38B, and they can be also used with specific modifications for FIGS. 17A-36, and 41-46)
- electromagnetic generators using a flat coil (FIG. 14 and they can be also used with specific modifications for FIGS. 17A-24, 27-36, and 41-46)
- electromagnetic generators using a cylindrical coil (FIG. 13 and they can be also used with specific modifications for FIGS. 17A-24, 27-36, and 41-46)

For some of the figures mentioned above, although one of the principle/method of waves generation is specifically presented in the figure, other methods may also apply, based on each embodiment construction. That it will be mentioned for each figure where such situation applies.

In general, the energy is delivered for all embodiments presented in this invention from a power supply in the form of high voltage setting for electrohydraulic and piezoelectric devices and electrical current setting for electromagnetic devices and ultrasonic devices. The power supply functionality and the parameters of the cleaning and high-level disinfection process performed by the decontamination system is controlled by a control console/unit, designed to have processors and microprocessors, displays, input/output elements, timers, memory units, remote control devices, independent power unit, etc. Each of these components may include hardware, software, or a combination of hardware and software configured to perform one or more functions associated with providing good functioning of the whole decontamination system that employs the use of the focused acoustic pressure shockwaves or pressure waves (acoustic planar pressure waves or pseudo-planar pressure waves or acoustic radial pressure waves) and low-frequency ultrasound waves.

Sometimes combination geometries ca be used for the reflectors mentioned in the present inventions. Two or more geometries can be used (portion of an ellipsoid, combined with a portion of a sphere and a portion of a paraboloid). That can have an effect on the way the shockwaves or pressure waves are reflected, how many focal volumes are created that can overlap or can be totally separated, and finally the actual focal volume shape and its position in space.

Figure 37:
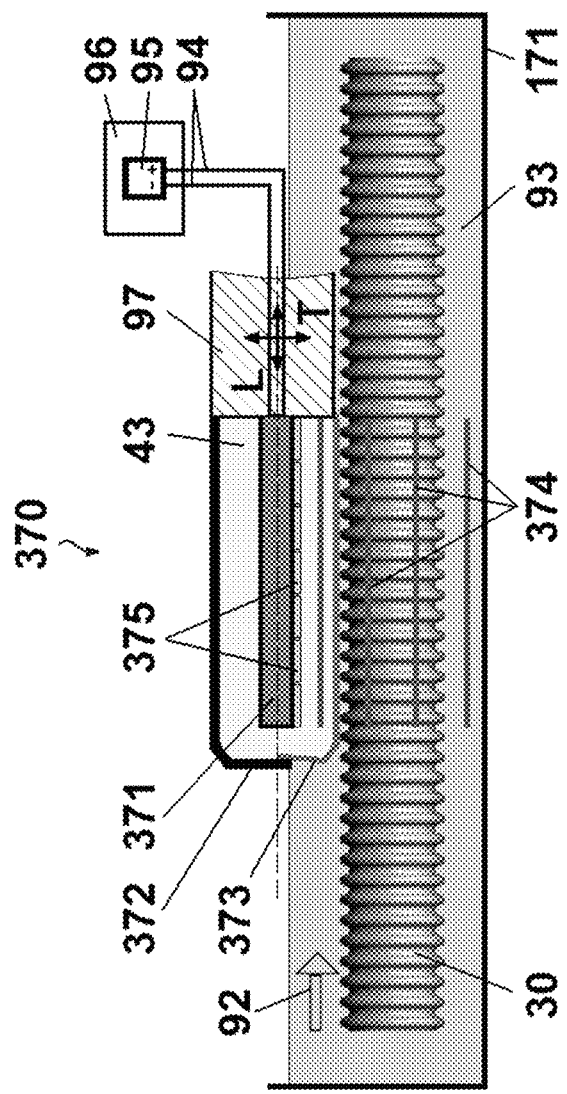
FIG. 37 is a schematic representation of a piezoelectric system producing planar waves for cleaning and high-level disinfection of endoscopes or reusable tubing from ventilators and dialysis machines or from any other medical devices, according to one embodiment of the present invention.

Non-rotational reflector geometries can be also used to reflect shockwaves or pressure waves. In this case, the reflector can have a pyramid geometry with triangle, square, hexagonal, or octagonal aperture. In other situations, no reflectors are used at all, where multiple spark-gap or laser electrohydraulic sources are used (see FIGS. 39 and 40) or simply flat piezo-crystals (FIGS. 37 and 38B) or flat piezo-fibers composites (FIG. 37). In these cases, a planar pressure wave or a radial pressure wave or an ultrasound wave is crated that moves in any direction or preferred directions.

The embodiments of the present inventions that are used to clean and disinfected endoscopes or reusable contaminated/tubes from respirators, hemodialysis units and any other medical devices, are further described in detail in the following paragraphs.

Figure 9:
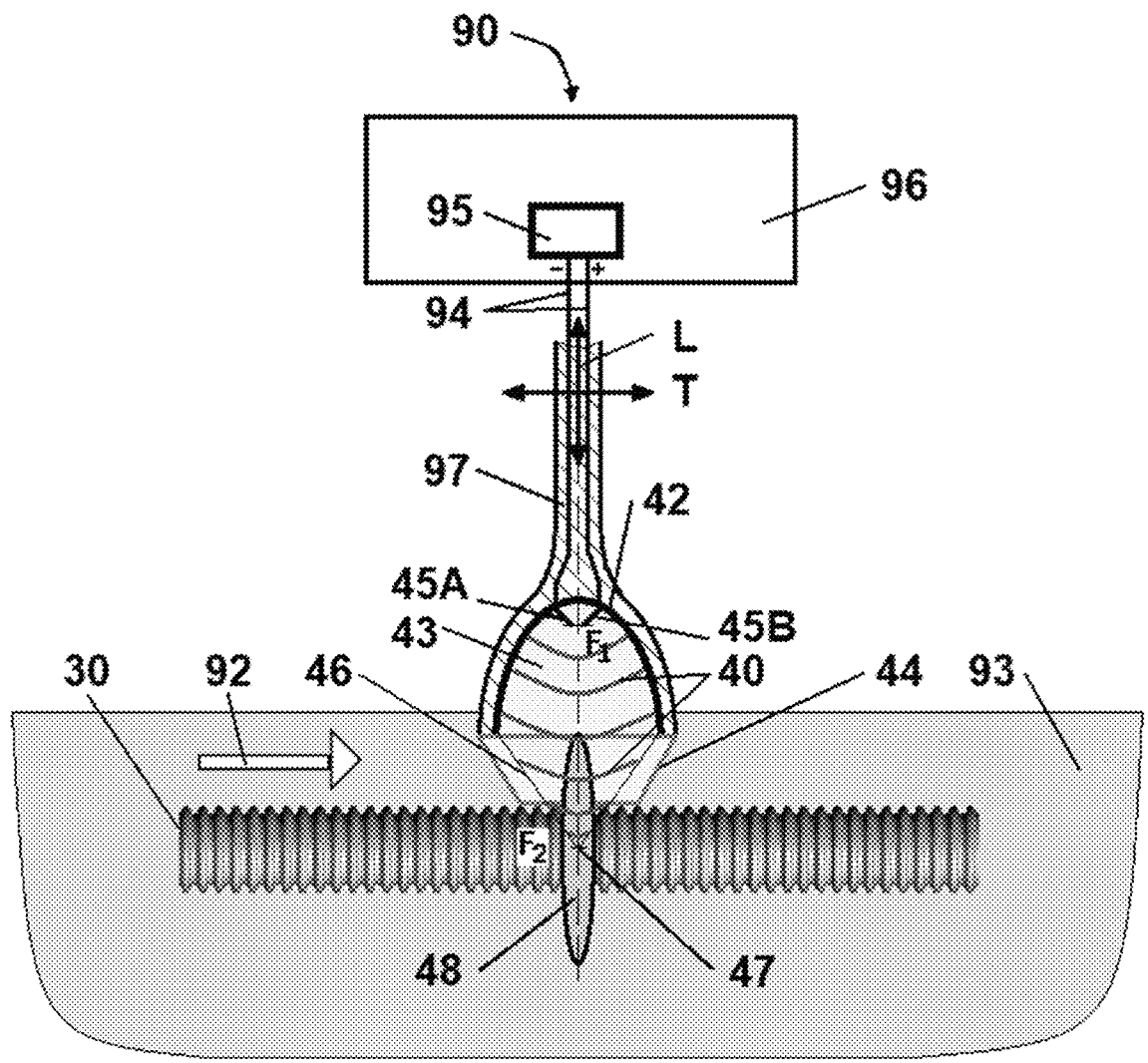
FIG. 9 is a schematic representation of an electrohydraulic focused shockwaves system for cleaning and high-level disinfection of endoscopes or reusable tubing from ventilators and dialysis machines and other medical devices in one embodiment of the present invention.

In FIG. 9 presents a decontamination system 90 using the focused acoustic pressure shockwaves 40 that are generated via high voltage discharge produced in between first electrode 45A and the second electrode 45B (electrohydraulic principle using spark gap high voltage discharges) in a fluid present inside the reflector cavity 43. The high voltage for the first electrode 45A and the second electrode 45B is provided by the power supply 95 (included in control console/unit 96) via high voltage cable 94. The two electrodes 45A and 45B are positioned in the first focal point $F_1$ (forming the spark-gap 41, as presented in FIG. 4) of the semi-ellipsoidal reflector 42. During high voltage discharge a plasma bubble is generated that expands and collapses transforming the heat into kinetic energy in the form of acoustic pressure shockwaves that reflect on the semi-ellipsoidal reflector 42, and through shockwave focusing 46 are producing the focused acoustic pressure shockwaves 40, which are directed through the applicator/coupling membrane 44 towards the focal point 47 ($F_2$ of the ellipsoidal geometry) and overall to the focal volume 48 that overlaps with the targeted cleaning and high-level disinfection region where the endoscope 30 or reusable contaminated tubing 30 is present. To be able to properly/completely overlap the focal volume 48 with the endoscope 30 or reusable contaminated tubing 30, the transversal (T) and longitudinal (L) motions of the applicator 97 are performed manually by the operator or by using semi-automatic or automatic means. Since the focused acoustic pressure shockwaves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B).

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicator 97 moves and sometimes both. In FIG. 9 the movement of an endoscope 30, or reusable contaminated tubing 30 from respirators or hemodialysis units or from any other medical devices, in front of the focused acoustic pressure shockwaves 40 can be done manually or automatic via a motorized system, which assures the complete exposure of the entire contaminated areas, regardless of the device/part length. This is why the endoscopes 30, or the reusable contaminated tubing 30 (tubes) from respirators, hemodialysis units, and any other medical devices are moving in the tubing/endoscope moving direction 92 and in front of the focused acoustic pressure shockwaves 40.

Figure 10:
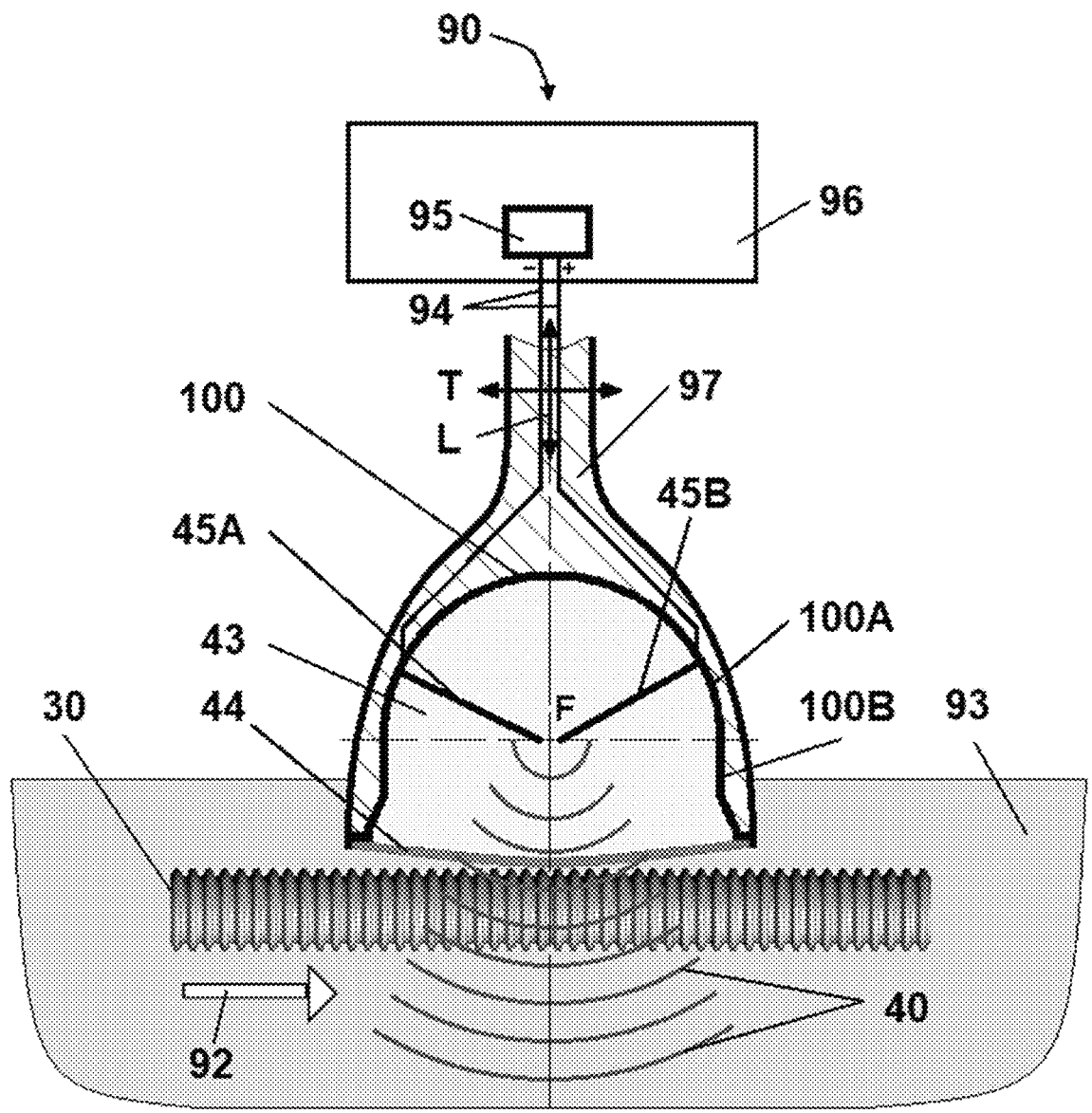
FIG. 10 is a schematic representation of an electrohydraulic radial pressure waves system for cleaning and high-level disinfection of endoscopes or reusable tubing from ventilators and dialysis machines and other medical devices in one embodiment of the present invention.

In the embodiment from FIG. 10 the decontamination system 90 is using a combination semi-spherical and cylindrical reflector 100 that sends acoustic radial pressure waves 40 towards the endoscope 30 or reusable contaminated tubing 30. The acoustic pressure wave applicator 97 is producing the acoustic radial pressure waves 40 in the center F of semi-spherical reflector portion 100A of the combination semi-spherical and cylindrical reflector 100 that has in its upper part the cylindrical reflector portion 100B above the plane of the central point F and slightly tapered at the aperture (reflector's opening). The applicator/coupling membrane 44 sits at the aperture/opening of the combination semi-spherical and cylindrical reflector 100 and thus creating a fluid-filled reflector cavity 43. The "direct" acoustic radial pressure waves 40 are generated via the high voltage discharge between first electrode 45A and second electrode 45B and they travel from the center F of semi-spherical reflector portion 100A through the aperture of the acoustic pressure wave applicator 97 and applicator/coupling membrane 44 directly to the endoscope 30 or reusable contaminated tubing 30 without any reflection. The high voltage for the first electrode 45A and the second electrode 45B is provided by the power supply 95 (included in control console/unit 96) via high voltage cable 94. Due to the special construction of the combination semi-spherical and cylindrical reflector 100, the spheric waves/radial waves that are reaching the reflecting surface of the combination semi-spherical and cylindrical reflector 100 are reflected back towards the spherical center F or the longitudinal axis of the reflector. This avoids unnecessary reflected radial waves to be directed towards the endoscope 30 or reusable contaminated tubing 30 that can interfere with the "direct" acoustic radial pressure waves 40. Since the "direct" acoustic radial pressure waves 40 are produced in a liquid medium, in order to not lose energy through reflections at the change of acoustic impedance from one medium to another and fully take advantage of the micro jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B). By their nature, the "direct" acoustic radial pressure waves 40 (exiting through the aperture of the combination semi-spherical and cylindrical reflector 100) are unfocused and thus they move through the radial waves pressure field 63 (seen in FIG. 6) and through the endoscope 30 or reusable contaminated tubing 30 without being able to be concentrated/focused in a certain focal region, as seen before for the focused acoustic pressure shockwaves 40 (schematically shown in FIGS. 4, 8, and 9). Another way to create acoustic radial pressure waves 40 is given by ballistic devices that use pneumatics to push at high speeds a small cylindrical piece (bullet) against a plate that vibrates (due to the impact of the bullet) and thus creating/generating acoustic radial pressure waves 40. The ballistic devices were not specifically depicted in any of the figures of this invention, but can be used to generate acoustic radial pressure waves 40. To be able to properly overlap the acoustic radial pressure waves 40 with the reusable contaminated tubing 30, the transversal (T) and longitudinal (L) motions of the applicator 97 are performed manually by the operator or by using semi-automatic or automatic means.

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicator 97 moves and sometimes both, using manually or motorized automatic means. In FIG. 10 the endoscope 30, or reusable contaminated tubing 30 from respirators or hemodialysis units or from any other medical devices is moving in the tubing/endoscope moving direction 92 and in front of the acoustic radial pressure waves 40.

In the embodiment shown in FIG. 11 the decontamination system 90 is using a parabolic reflector 51 that sends pseudo-planar pressure waves 40 outside the applicator/coupling membrane 44 and through the endoscope 30 or reusable contaminated tubing 30. The parabolic reflector 51 has only a central point/focus point F (parabolic focal point) where radial acoustic pressure waves 40 are generated (via the high voltage discharge between first electrode 45A and second electrode 45B in the liquid present inside the reflector cavity 43). The acoustic radial pressure waves 40 propagate and reflect on the parabolic reflector 51 at different time points, which creates secondary pressure wave fronts (not shown on FIG. 11 to keep clarity), especially at the edge/aperture of the parabolic reflector 51. The combination of direct acoustic radial pressure waves 40 with the secondary pressure wave fronts creates pseudo-planar pressure waves 40 outside the applicator/coupling membrane 44, forming the pseudo-planar waves pressure field 55 (as seen in FIG. 5). In this case presented in FIG. 11, the parabolic focal point F is present inside the parabolic reflector 51 of the applicator 97 and this is why pseudo-planar pressure waves 40 are produced outside the applicator/coupling membrane 44 and pass through the endoscope 30 or reusable contaminated tubing 30. This is different from the embodiments presented in FIGS. 13-16, where the parabolic focal point F is outside the parabolic reflector 51 of the applicator 97 and it is overlapping with the longitudinal axis of the endoscope 30 or reusable contaminated tubing 30. This is why the embodiments from FIGS. 13-16 produce focused acoustic pressure shockwaves 40 outside the applicator/coupling membrane 44 that are passing through the endoscope 30 or reusable contaminated tubing 30.

By their nature, the pseudo-planar pressure waves 40 (exiting through the aperture of the parabolic reflector 51 and the applicator/coupling membrane 44) are unfocused and thus they move away from their point of origin F (parabolic focal point) without being able to be concentrated in a certain focal region, as seen for the focused acoustic pressure shockwaves 40 (shown in FIGS. 9, 13-19, 23-24, 25A, 25B, 31, and 32). The action of the pseudo-planar pressure waves 40 outside the applicator/coupling membrane 44 is controlled by the input energy, delivered via the cable 94 from the power supply 95 that is controlled by the control console/unit 96. To be able to perform properly the cleaning and high-level disinfection process, the pseudo-planar waves pressure field 55 (see FIG. 5), produced outside the applicator/coupling membrane 44 by the pseudo-planar pressure waves 40, needs to overlap with the endoscope 30 or reusable contaminated tubing 30. To accomplish that the transversal (T) and longitudinal (L) motions of the applicator 97 are performed manually by the operator or by using semi-automatic or automatic means. Since the pseudo-planar pressure waves 40 are produced in a liquid medium, in order to not lose energy through reflections at the change of acoustic impedance from one medium to another and fully take advantage of the micro jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B).

To assure the complete cleaning and decontamination on the full length of medical devices such as endoscopes 30 or of the reusable contaminated tubing 30 from respirators, hemodialysis units and any other medical devices, either the contaminated device/part needs to move or alternatively the applicator 97 moves and sometimes both, using manually or motorized automatic means. In FIG. 11 the endoscope 30, or reusable contaminated tubing 30 from respirators or hemodialysis units or from any other medical devices is moving in the tubing/endoscope moving direction 92 and in front of the pseudo-planar pressure waves 40.

In FIG. 12 the decontamination system 90 is using the focused acoustic pressure shockwaves 40 that are generated via one or multiple laser sources (electrohydraulic principle using one or multiple lasers sources). In this specific case, the laser beams produced by first incased laser 45C and the second incased laser 45D in a fluid present inside the reflector cavity 43 generate the acoustic pressure shockwaves 40, which are then focused via semi-ellipsoidal reflector 42 towards the focal point 47 ($F_2$ of the ellipsoidal geometry) and overall, to the focal volume 48 that overlaps with endoscope 30 or of the reusable contaminated tubing 30 from respirators, hemodialysis units and any other medical devices. The high voltage for the first incased laser 45C and the second incased laser 45D is provided by the power source 95 (included in control/console unit 96) via high voltage cable 94. The two laser sources are positioned in such way to intersect their beams in the first focal point $F_1$ of the semi-ellipsoidal reflector 42 in order to produce a plasma bubble that expands and collapses transforming the heat into kinetic energy in the form of acoustic pressure shockwaves that reflect on the semi-ellipsoidal reflector 42, and through shockwave focusing 46 are producing the focused acoustic pressure shockwaves 40, which are directed towards the focal point 47 ($F_2$ of the ellipsoidal geometry) and overall to the focal volume 48 that overlaps with the targeted cleaning and high-level disinfection region where the endoscope 30 or reusable contaminated tubing 30 is present. FIG. 12 includes a means of monitoring the system performance by measuring the reaction temperature of the plasma bubble collapse using a method of optical fiber thermometry. An optical fiber tube assembly 120 extends into the $F_1$ region of the semi-ellipsoidal reflector 42. The optical fiber tube assembly 120 transmits (via optical fiber 121) specific spectral frequencies created from the sonoluminescence of the plasma bubble reaction in the fluid present inside the reflector cavity 43 to the spectral analyzer 122. The loop is closed via feedback cable 123 that connects the spectral analyzer 122 with the power supply 95. Basically, the spectral analysis provided by the spectral analyzer 122 is used to adjust accordingly the power generated by the power supply 95, to ensure a proper laser discharge for the incased lasers 45C and 45D. To be able to properly overlap the focal volume 48 with the endoscope 30 or reusable contaminated tubing 30, the transversal (T) and longitudinal (L) motions of the applicator 97 are performed manually by the operator or by using semi-automatic or automatic means. Since the focused acoustic pressure shockwaves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B).

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicator 97 moves and sometimes both, using manually or motorized automatic means. In FIG. 12 the endoscope 30, or reusable contaminated tubing 30 from respirators or hemodialysis units or from any other medical devices is moving in the tubing/endoscope moving direction 92 and in front of the focused acoustic pressure shockwaves 40.

In FIGS. 9 and 12, where the electrohydraulic principle is used to produce focused acoustic pressure shockwaves 40, if the semi-ellipsoidal reflector 42 is replaced with a parabolic reflector 51 (see FIG. 5) that has its parabolic focal point (F) in the same position as the first focal point ($F_1$) of the semi-ellipsoidal reflector 42, then the applicator 97 will produce pseudo-planar pressure waves 40, similar to those from the embodiment presented in FIG. 11.

In FIG. 13 the decontamination system 90 is using the focused acoustic pressure shockwaves 40 that are generated via electromagnetic cylindrical coil and tube assembly 45H (electromagnetic principle using a cylindrical coil). In this case, an electromagnetic cylindrical coil is excited by a short electrical pulse provided by the power supply 95 (included in control console/unit 96) via high voltage cable 94, and the plate is in the shape of a tube (thus creating an electromagnetic cylindrical coil and tube assembly 45H), which will results in a cylindrical pressure wave (not shown in FIG. 13) that can be focused by a parabolic reflector 51 (shockwave focusing 46) towards the parabolic focal point 47 (F) and overall, to the focal volume 48. When the electromagnetic cylindrical coil is excited by a short electrical pulse provided by the power supply 95 (included in control console/unit 96) via high voltage cable 94, the cylindrical coil experiences a repulsive force and this is used to generate a cylindrical acoustic pressure wave inside the fluid-filled reflector cavity 43 that is reflected on the parabolic reflector 51, thus creating focused acoustic pressure shockwaves 40.

Conversely, in another embodiment the parabolic reflector 51 can be replaced by a semi-ellipsoidal reflector 42 to create unfocused pressure waves that generate a pressure field outside the applicator/coupling membrane 44 of the semi-ellipsoidal reflector 42, pressure field that needs to overlap with the endoscope 30 or reusable contaminated tubing 30, to produce their cleaning and decontamination.

To be able to perform properly the cleaning and high-level disinfection process, the endoscope 30 or reusable contaminated tubing 30 needs to overlap with the focal volume 48 (for focused acoustic pressure shockwaves 40) or the pressure field produced outside the applicator/coupling membrane 44 by unfocused pressure waves, when the parabolic reflector 51 is replaced by a semi-ellipsoidal reflector 42. To accomplish that, the transversal (T) and longitudinal (L) motions of the applicator 97 are performed manually by the operator or by using semi-automatic or automatic means. For FIG. 13, since the focused acoustic pressure waves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B).

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicator 97 moves and sometimes both, using manually or motorized automatic means. In FIG. 13 the endoscope 30, or reusable contaminated tubing 30 from respirators or hemodialysis units or from any other medical devices is moving in the tubing/endoscope moving direction 92 and in front of the focused acoustic pressure shockwaves 40.

Figure 14:
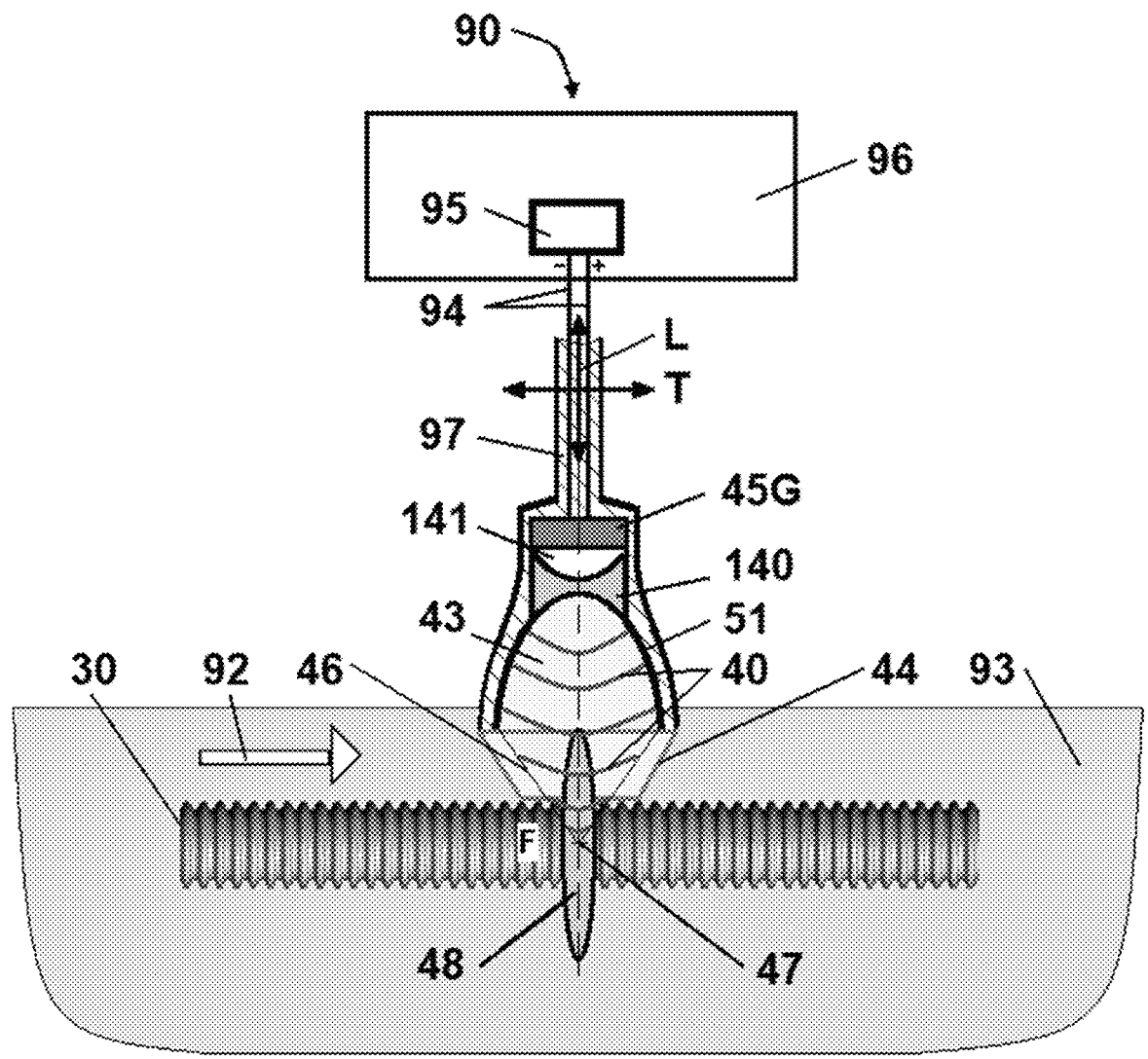
FIG. 14 is a schematic representation of a flat coil-produced electromagnetic focused shockwaves system for cleaning and high-level disinfection of endoscopes or reusable tubing from ventilators and dialysis machines and other medical devices in one embodiment of the present invention.

In FIG. 14 the decontamination system 90 is using the focused acoustic pressure shockwaves 40 that are generated via electromagnetic flat coil and plate assembly 45G and an acoustic lens 140 (electromagnetic principle using a flat coil and an acoustic lens). In this case, an electromagnetic flat coil is placed in close proximity to a metal plate that acts as an acoustic source and thus the electromagnetic flat coil and plate assembly 45G presented in FIG. 14 is created. When the electromagnetic flat coil is excited by a short electrical pulse provided by the power supply 95 (included in control console/unit 96) via high voltage cable 94, the plate experiences a repulsive force and this is used to generate an acoustic pressure wave. Due to the fact that the metal plate is flat, the resulting acoustic pressure wave is a planar acoustic pressure wave (not shown in FIG. 14) that is moving in the fluid-filled cavity 141 towards the acoustic lens 140, which is focusing the planar wave (shockwave focusing 46) and thus creating the focused acoustic pressure shockwaves 40. The focusing effect of the acoustic lens 140 is given by its shape, which as presented in FIG. 14 is a portion of a parabolic surface. This is why the acoustic lens 140 is used in tandem with a parabolic reflector 51 that can help with the focusing of the produced focused acoustic pressure shockwaves 40 towards the parabolic focal point 47 (F) and overall, to the focal volume 48.

Conversely, in another embodiment the acoustic lens 140 can be a portion of an ellipsoidal surface and in combination with a semi-ellipsoidal reflector 42 can create unfocused pressure waves that can generate a pressure field outside the applicator/coupling membrane 44 of the semi-ellipsoidal reflector 42, pressure field that needs to overlap with the endoscope 30 or reusable contaminated tubing 30, to produce their cleaning and decontamination.

To be able to perform properly the cleaning and high-level disinfection process, the endoscope 30 or reusable contaminated tubing 30 needs to overlap with the focal volume 48 (for focused acoustic pressure shockwaves 40) or the pressure field produced outside the applicator/coupling membrane 44 by unfocused pressure waves, when the parabolic reflector 51 is replaced by a semi-ellipsoidal reflector 42. To accomplish that the transversal (T) and longitudinal (L) motions of the applicator 97 are performed manually by the operator or by using semi-automatic or automatic means. For FIG. 14, since the focused acoustic pressure waves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B).

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicator 97 moves and sometimes both, using manually or motorized automatic means. In FIG. 14 the endoscope 30, or reusable contaminated tubing 30 from respirators or hemodialysis units or from any other medical devices is moving in the tubing/endoscope moving direction 92 and in front of the focused acoustic pressure shockwaves 40.

Figure 15:
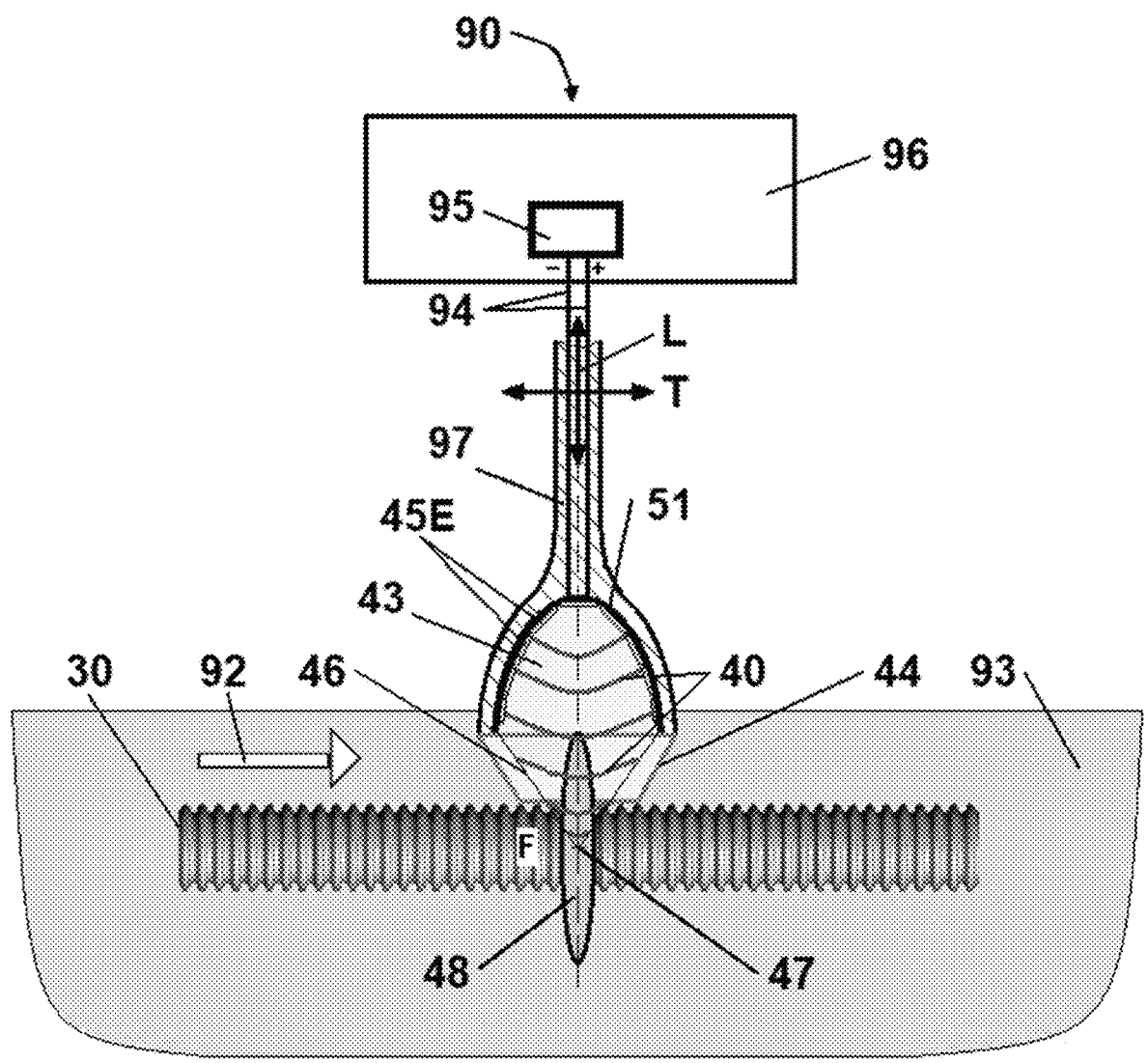
FIG. 15 is a schematic representation of a piezo crystals/piezo ceramics-produced piezoelectric focused shockwaves system for cleaning and high-level disinfection of endoscopes or reusable tubing from ventilators and dialysis machines and other medical devices in one embodiment of the present invention.

In FIG. 15 the decontamination system 90 is using the focused acoustic pressure shockwaves 40 that are generated via piezo crystals/piezo ceramics 45E (piezoelectric principle using piezo crystals/piezo ceramics). In this case, the internal generation of a mechanical strain resulting from an applied electrical field to the piezo crystals/piezo ceramics 45E, which are uniformly placed on a parabolic reflector 51, generate in a fluid present inside the reflector cavity 43 the focused acoustic pressure shockwaves 40. The parabolic reflector 51 produces the shockwave focusing 46 towards its focal point F (parabolic focal point 47) and overall, to the focal volume 48. To accomplish the shockwave focusing 46, all the surface of the parabolic reflector 51 is covered by the piezo crystals/piezo ceramics 45E. The electrical field for the piezo crystals/piezo ceramics 45E is provided by the power supply 95 (included in control console/unit 96) via high voltage cable 94.

Relatively similar effects can be accomplished when the piezo crystals/piezo ceramics 45E are used together with the semi-ellipsoidal reflector 42. In this case, since the pressure waves are originating from the surface of the semi-ellipsoidal reflector 42 and not from the focal point $F_1$ of the ellipsoidal geometry, the produced pressure waves fall more in the category of unfocused pressure waves and not shockwaves. The unfocused pressure waves can generate a pressure field outside the applicator/coupling membrane 44 of the semi-ellipsoidal reflector 42, pressure field that needs to overlap with the endoscope 30 or reusable contaminated tubing 30, to produce their cleaning and decontamination.

To be able to perform properly the cleaning and high-level disinfection process, the endoscope 30 or reusable contaminated tubing 30 needs to overlap with the focal volume 48 (for focused acoustic pressure shockwaves 40) or the pressure field produced outside the applicator/coupling membrane 44 by unfocused pressure waves, when the parabolic reflector 51 is replaced by a semi-ellipsoidal reflector 42. To accomplish that, the transversal (T) and longitudinal (L) motions of the applicator 97 are performed manually by the operator or by using semi-automatic or automatic means. For FIG. 15, since the focused acoustic pressure waves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B).

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicator 97 moves and sometimes both, using manually or motorized automatic means. In FIG. 15 the endoscope 30, or reusable contaminated tubing 30 from respirators or hemodialysis units or from any other medical devices is moving in the tubing/endoscope moving direction 92 and in front of the focused acoustic pressure shockwaves 40.

Due to the parallelepiped or cylindrical geometry of the piezo crystals/piezo ceramics 45E, they may not fit very well to the parabolic reflector 51 surface, which can create problems with focusing towards the parabolic focal point 47 (F), especially in situations where deep penetrations are needed, since these geometries will require a sharp vertex of the parabola with smaller radiuses that are difficult to cover with parallelepiped or cylindrical piezo crystals/piezo ceramics 45E. To overcome this issue, the piezo crystals/piezo ceramics 45E can be replaced by piezo fibers in the construction of a decontamination system 90, as presented in FIG. 16. The piezo fibers can be integrated in a composite material with their longitudinal axis perpendicular to a solid surface as the parabolic reflector 51, thus forming a piezo fiber layer 45F capable of producing focused acoustic pressure shockwaves 40. The advantage of the piezo fiber layer 45F when compared to the piezo crystals/piezo ceramics 45E is that the smaller dimension and cylindrical geometry (hair-like geometry) of the piezo fibers allows them to fit significantly better to the parabolic or ellipsoidal geometries. Furthermore, the electric contacting of the piezo fibers may be realized by a common electrically conductive layer according to the interconnection requirements. Hence, the complex interconnection of a multitude of piezo crystals/piezo ceramics 45E (as presented in FIG. 16) is no longer required. When an electrical field is provided by the power supply 95 (included in control console/unit 96) via high voltage cable 94 to the piezo fiber layer 45F, the piezo electric fibers will stretch in unison mainly in their lengthwise direction, which will create focused acoustic pressure shockwaves 40 from the surface of the parabolic reflector 51 that is producing shockwave focusing 46 towards the parabolic focal point 47 (F) and overall, to the focal volume 48.

Relatively similar effects can be accomplished when the piezo fiber layer 45F is used together with a semi-ellipsoidal reflector 42, but in this case since the pressure waves are originating from the surface of the semi-ellipsoidal reflector 42 and not from the focal point $F_1$ of the ellipsoidal geometry, and thus the produced pressure waves fall more in the category of unfocused waves and not shockwaves. The unfocused pressure waves can generate a pressure field outside the applicator/coupling membrane 44 of the semi-ellipsoidal reflector 42, pressure field that needs to overlap with the endoscope 30 or reusable contaminated tubing 30, to produce their cleaning and decontamination.

To be able to perform properly the cleaning and high-level disinfection process, the endoscope 30 or reusable contaminated tubing 30 needs to overlap with the focal volume 48 (for focused acoustic pressure shockwaves 40) or the pressure field produced outside the applicator/coupling membrane 44 by unfocused pressure waves, when the parabolic reflector 51 is replaced by a semi-ellipsoidal reflector 42. To accomplish that, the transversal (T) and longitudinal (L) motions of the applicator 97 are performed manually by the operator or by using semi-automatic or automatic means. For FIG. 16, since the focused acoustic pressure waves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B).

Figure 16:
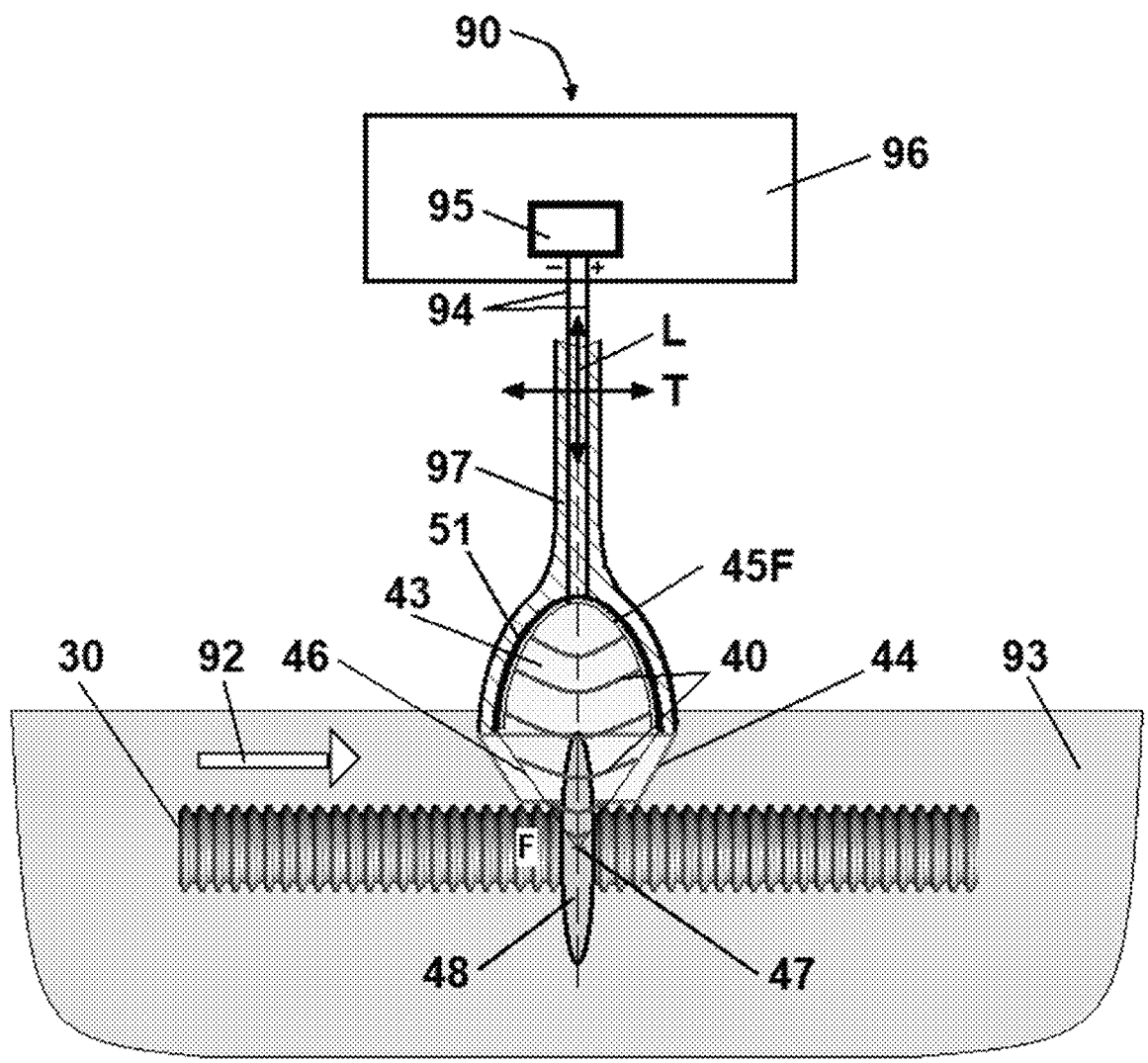
FIG. 16 is a schematic representation of a piezo fibers-produced piezoelectric focused shockwaves system for cleaning and high-level disinfection of endoscopes or reusable tubing from ventilators and dialysis machines and other medical devices in one embodiment of the present invention.

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicator 97 moves and sometimes both, using manually or motorized automatic means. In FIG. 16 the endoscope 30, or reusable contaminated tubing 30 from respirators or hemodialysis units or from any other medical devices is moving in the tubing/endoscope moving direction 92 and in front of the focused acoustic pressure shockwaves 40.

Figure 17A:
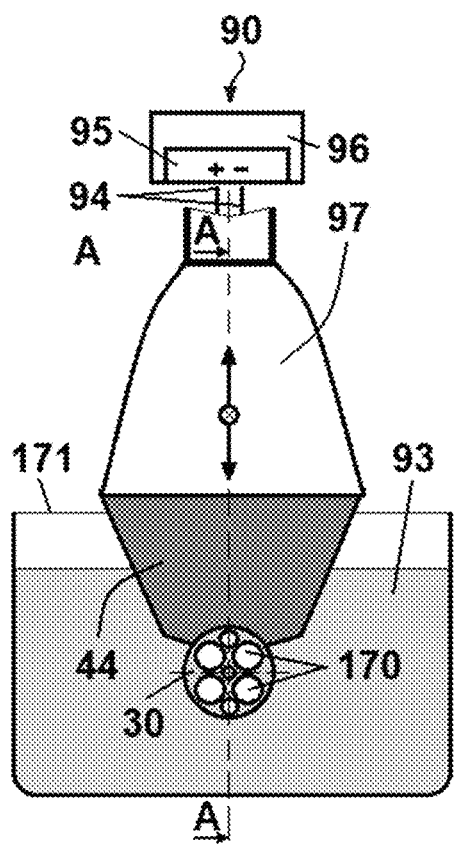
FIG. 17A is a schematic representation of a manual or semi-automatic system for cleaning and high-level disinfection of endoscopes or reusable tubing from ventilators and dialysis machines and other medical devices using one focused shockwave applicator in direct contact with endoscope or tubing, according to one embodiment of the present invention.
Figure 17B:
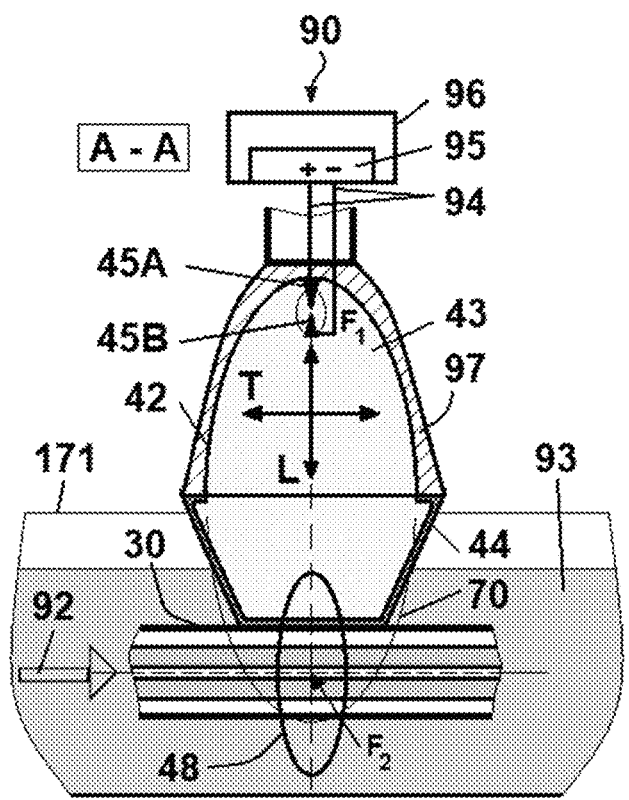
FIG. 17B is a cross-sectional schematic representation of the system illustrated in FIG. 17A taken along line A-A, according to one embodiment of the present invention.

The embodiment from FIGS. 17A and 17B shows how a manual or a semi-automatic system using one applicator 97 can be used to produce the cleaning and decontamination of endoscopes 30 or of the reusable contaminated tubing 30 using the focused acoustic pressure shockwaves 40. The decontamination system 90 is using the focused acoustic pressure shockwaves 40 that are generated via high voltage discharge produced in between first electrode 45A and the second electrode 45B (electrohydraulic principle using spark gap high voltage discharges) in a fluid present inside the reflector cavity 43. The high voltage for the first electrode 45A and the second electrode 45B is provided by the power supply 95 (included in control console/unit 96) via high voltage cable 94. The two electrodes 45A and 45B are positioned in the first focal point $F_1$ (forming the spark-gap 41, as presented in FIG. 4) of the semi-ellipsoidal reflector 42. During high voltage discharge a plasma bubble is generated that expands and collapses transforming the heat into kinetic energy in the form of acoustic pressure shockwaves that reflect on the semi-ellipsoidal reflector 42, producing the focused acoustic pressure shockwaves 40, which are directed through the applicator/coupling membrane 44 towards the focal point $F_2$ of the ellipsoidal geometry and overall to the focal volume 48 that overlaps with the targeted cleaning and high-level disinfection region where the endoscope 30 or reusable contaminated 30 is present. To be able to properly overlap the focal volume 48 with the endoscope 30 or reusable contaminated tubing 30, the transversal (T) and longitudinal (L) motions of the applicator 97 are performed manually by the operator or by using semi-automatic or automatic means. Since the focused acoustic pressure shockwaves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B). The liquid bath enclosure 171 of the liquid bath 93 has the proper dimensions to accommodate the applicator 97 and the endoscope 30 or reusable contaminated tubing 30 that must stay submerged at all time in the field of action of the applicator 97 and its focal volume 48 during the cleaning and the high-level disinfection process. Considering the significant length of an endoscope 30 or reusable contaminated tubing 30, to not increase considerable the dimensions of the bath enclosure 171, the endoscope 30 or reusable contaminated tubing 30, after passing in front of the focused acoustic pressure shockwaves 40 and through the focal volume 48, can exit the liquid bath 93. Similarly, the endoscope 30 or reusable contaminated tubing 30 should enter the liquid bath 93 just before passing in front of the focused acoustic pressure shockwaves 40 and through the focal volume 48. To accomplish that the endoscope 30, or reusable contaminated tubing 30 from respirators or hemodialysis units or from any other medical devices is moving in the tubing/endoscope moving direction 92 and in front of the focused acoustic pressure shockwaves 40. Alternatively, in other situations the applicator 97 can be moved (instead of the medical tubing 30 such as endoscopes and other reusable medical device tubes) and sometimes both the applicator 97 and the medical tubing 30 such as endoscopes and other reusable medical device tubes are moving in opposite directions, using manually or motorized automatic means.

Although it was mentioned before that the embodiment from FIGS. 17A and 17B can be used for the cleaning and decontamination of endoscopes 30 or of the reusable contaminated tubing 30, specifically in the figure the schematic representation is of an endoscope 30, which shows different endoscope channels 170 found in an endoscope 30. Note that the applicator/coupling membrane 44 is in close contact and deforms ("hugs") around the surface of the endoscope 30 or reusable contaminated tubing 30, which assures an efficient action of the focused acoustic pressure shockwaves 40 inside the lumen or lumens of the endoscope 30 or reusable contaminated tubing 30. In this embodiment and the majority of the embodiments presented in the present inventions, the decontamination system 90 is focused on the cleaning and decontamination of the internal lumen of a reusable contaminated medical tubing 30 or of the endoscope channels 170 and less on their external surface, which in general can be much easier cleaned and high-level disinfected with classic/legacy methods. However, if the cleaning and high-level disinfection is needed to be performed by shockwaves or pressure waves or ultrasound for both external surface and the internal lumen or lumens of an endoscope 30 or reusable contaminated tubing 30, then there is no contact in between the applicator/coupling membrane 44 and the external surface of the endoscope 30 or reusable contaminated tubing 30, as presented in the embodiment from FIG. 22.

In FIGS. 17A and 17B if the semi-ellipsoidal reflector 42 is replaced with a parabolic reflector 51 (see FIG. 5) that has its parabolic focal point (F) in the same position as the first focal point ($F_1$) of the semi-ellipsoidal reflector 42, then the applicator 97 will produce pseudo-planar pressure waves 40, similar to those from the embodiment presented in FIG. 11.

Although the embodiment presented in FIGS. 17A and 17B shows specifically an electrohydraulic system that uses the spark-gap 41, the applicators 97 can also produce focused acoustic pressure shockwaves 40 or pressure waves (pseudo-planar pressure waves 40 or acoustic radial pressure waves 40) and low-frequency ultrasound waves 380 and 381 using electrohydraulic generators with lasers, piezoelectric generators (with piezo crystals/piezo ceramics or piezo fibers) or electromagnetic generators (with flat coils or cylindrical coils).

Figure 18:
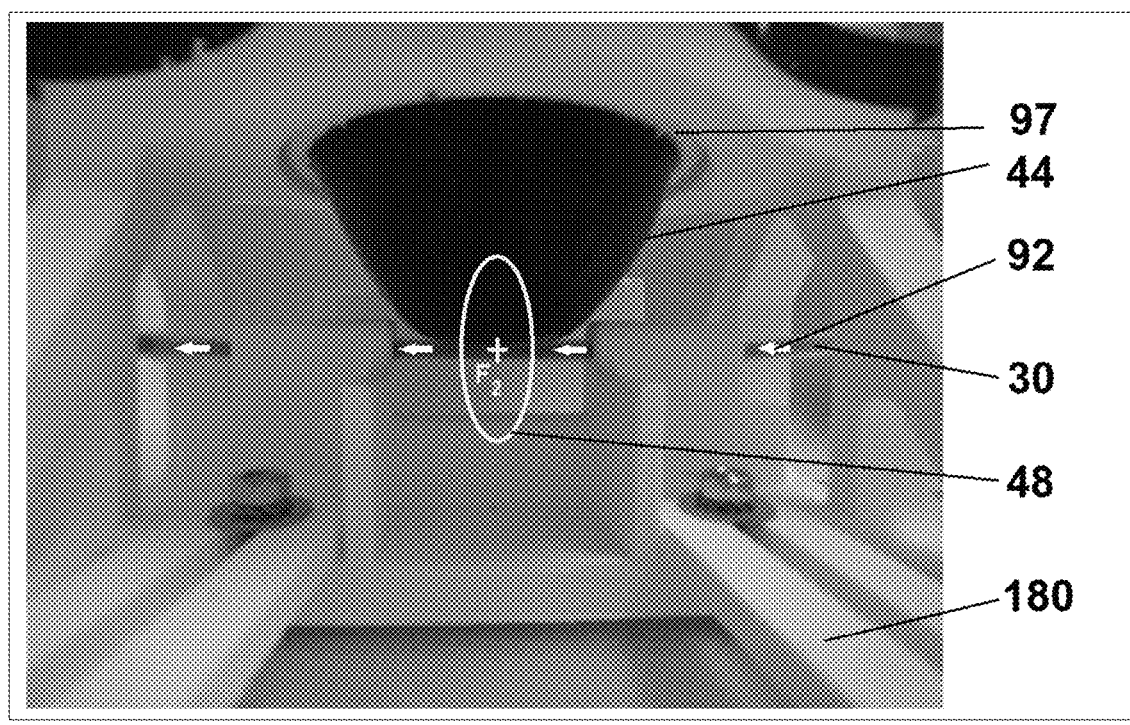
FIG. 18 illustrates a manual or semi-automatic fixture for cleaning and high-level disinfection of endoscopes or reusable tubing from ventilators and dialysis machines and other medical devices using one applicator in direct contact with endoscope or tubing, according to one embodiment of the present invention.

FIG. 18 shows an actual cleaning and high-level disinfection fixture 180 for endoscopes 30 or reusable contaminated tubing 30 from ventilators and dialysis machines or from any other medical devices. The cleaning and high-level disinfection fixture 180 is using one applicator 97 that has its applicator/coupling membrane 44 in direct contact with the endoscope 30 or reusable contaminated tubing 30. The endoscope 30 or reusable contaminated tubing 30 is moving in the tubing/endoscope moving direction 92 through manually actuation or by using semi-automatic/motorized systems. As seen from FIG. 18, the tubing/endoscope moving direction 92 allows the constant movement of the endoscope 30 or reusable contaminated tubing 30 through the focal volume 48 created by focused acoustic pressure shockwaves 40 that are produced by applicator 97. However, the same cleaning and high-level disinfection fixture 180 can also use unfocused pressure waves, acoustic planar pressure wave 374 or pseudo-planar pressure wave 40 or acoustic radial pressure wave 40 and low-frequency ultrasound waves 380 and 381, when the applicator 97 has different configurations, as presented in the embodiments from the inventions disclosed herein. Also, the embodiment presented in FIG. 18 can use applicators 97 that can produce focused acoustic pressure shockwaves 40 or pressure waves (acoustic planar pressure waves 374 or pseudo-planar pressure waves 40 or acoustic radial pressure waves 40) and low-frequency ultrasound waves 380 and 381 using electrohydraulic generators (with spark-gaps or lasers), piezoelectric generators (with piezo crystals/piezo ceramics or piezo fibers) or electromagnetic generators (with flat coils or cylindrical coils).

The number of applicators 97 that are used during cleaning and high-level disinfection of endoscopes 30 or reusable contaminated tubing 30 from ventilators and dialysis machines or from any other medical devices can vary from one applicator to two or more applicators, based on the necessary efficiency, soiling and processing time. FIGS. 19A and 19B show a manual or semi-automatic system for cleaning and disinfection endoscopes 30 or reusable contaminated tubing 30 from ventilators and dialysis machines or from any other medical devices, which has two confocal and opposite applicators 97 in direct contact with the endoscope 30 or reusable contaminated tubing 30 (via the applicator/coupling membranes 44). Due to the overlap of the two focal volumes 48 produced by the two applicators over the endoscopes 30 or reusable contaminated tubing 30, this embodiment is capable to produce more energy for the cleaning and the high-level disinfection process. The activation of the two applicators 97 can be done simultaneously or concomitantly, depending on the wanted outcomes of the respective process and type of endoscope 30 or reusable contaminated tubing 30. The focused acoustic pressure shockwaves 40 (not shown in FIGS. 19A and 19B) are generated via high voltage discharge produced in between first electrode 45A and the second electrode 45B (electrohydraulic principle using spark gap high voltage discharges) in a fluid present inside the reflector cavity 43. The high voltage for the first electrode 45A and the second electrode 45B is provided by the power supply 95 (included in control console/unit 96) via high voltage cable 94. The two electrodes 45A and 45B are positioned in the first focal point $F_1$ (forming the spark-gap 41, as presented in FIG. 4) of the semi-ellipsoidal reflector 42. During high voltage discharge a plasma bubble is generated that expands and collapses transforming the heat into kinetic energy in the form of acoustic pressure shockwaves that reflect on the semi-ellipsoidal reflectors 42, producing the focused acoustic pressure shockwaves 40, which are directed through the applicator/coupling membrane 44 towards the common focal point $F_2$ and overall to the focal volumes 48 that overlap with the targeted cleaning and high-level disinfection region where the endoscope 30 or reusable contaminated 30 is present. To be able to properly overlap the focal volumes 48 with the endoscope 30 or reusable contaminated tubing 30, the transversal (T) and longitudinal (L) motions of the applicators 97 are performed manually by the operator or by using semi-automatic or automatic means. Since the focused acoustic pressure shockwaves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 are placed into liquid bath 93 (not specifically shown in FIGS. 19A and 19B for clarity) and their lumen/lumens filled with a decontamination fluid 205 (see FIGS. 20B and 21B).

FIGS. 19A and 19B show the two applicators 97 positioned at 180 degrees apart (opposite), but they can be also at 90 degrees apart. In case that more than two applicators 97 are used, they can be positioned at any angular position around the endoscope 30 or reusable contaminated tubing 30. If three applicators 97 are used, they can be positioned at 120 degrees equally apart, or if four applicators 97 are used, they can be positioned at 90 degrees equally apart and so on. In other situations, the applicators 97 do not necessarily need to be positioned equally apart. For example, if four applicators 97 are used, the top two of them can be positioned at 40 degrees apart and the bottom two at 60 degrees apart, which means that the angle in between a top applicator and a bottom applicator will be 130 degrees. In the ultimate solution, the multiple applicators 97 can be moved automatically using a motorized fixture in any position desired by the operator or by an automatic system, based on the analysis of the endoscope 30 or reusable contaminated tubing 30 surface and configuration that is monitored by an automated visual system. This approach can be also applied for valves or other intricate parts or devices that require decontamination, and the applicators 97 need to cover all the "nooks and crannies" of such special parts or components or medical devices.

In FIGS. 19A and 19B if the two semi-ellipsoidal reflectors 42 are replaced with two parabolic reflectors 51 (see FIG. 5) that have their parabolic focal point (F) in the same position as the first focal point ($F_1$) of the two semi-ellipsoidal reflectors 42, then the applicators 97 will produce pseudo-planar pressure waves 40, similar to those from the embodiment presented in FIG. 11. Conversely, one of the applicators 97 can have the semi-ellipsoidal reflector 42 and the second one can have the parabolic reflector 51, which will produce in the cleaning and decontamination area/volume a combination of focused acoustic pressure shockwaves 40 and pseudo-planar pressure waves 40.

Although it was mentioned before that the embodiment from FIGS. 19A and 19B can be used for the cleaning and decontamination of endoscopes 30 or of the reusable contaminated tubing 30, specifically in the figures the schematic representation is of an endoscope 30, which shows different endoscope channels 170 found in an endoscope 30.

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicators 97 move and sometimes both, using manually or motorized automatic means. In FIGS. 19A and 19B, the endoscope 30, or reusable contaminated tubing 30 from respirators or hemodialysis units or from any other medical devices is moving in the tubing/endoscope moving direction 92 through the common focal volume 48.

Although the embodiment presented in FIGS. 19A and 19B shows specifically an electrohydraulic system that uses the spark-gaps 41, the applicators 97 can also produce focused acoustic pressure shockwaves 40 or pressure waves (pseudo-planar pressure waves 40 or acoustic radial pressure waves 40) and low-frequency ultrasound waves 380 and 381 using electrohydraulic generators with lasers, piezoelectric generators (with piezo crystals/piezo ceramics or piezo fibers) or electromagnetic generators (with flat coils or cylindrical coils).

Figure 20A:
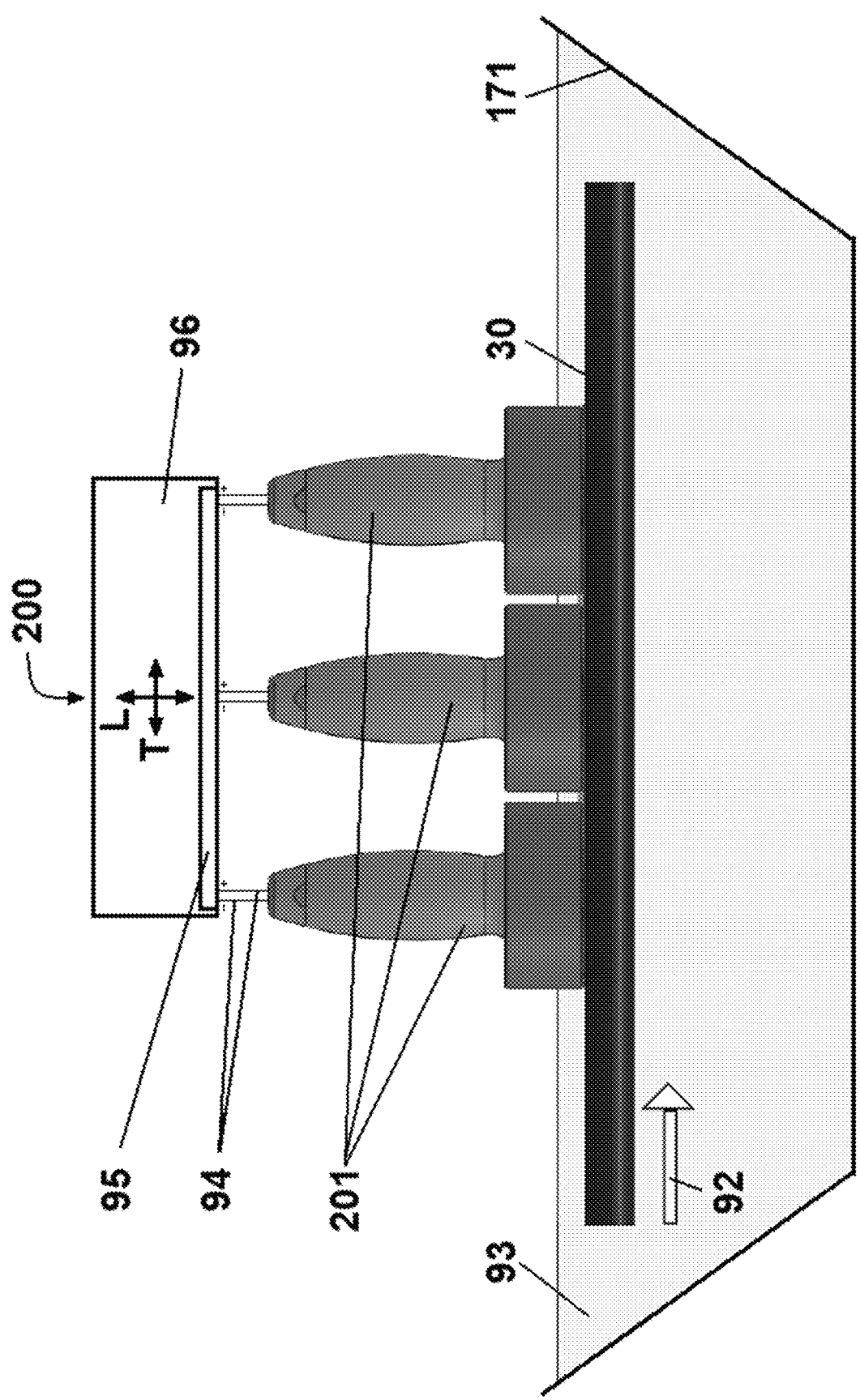
FIG. 20A is a schematic representation of a manual or semi-automatic system for cleaning and high-level disinfection of endoscopes using three focused shockwave applicators in direct contact with the endoscope, according to one embodiment of the present invention.
Figure 20B:
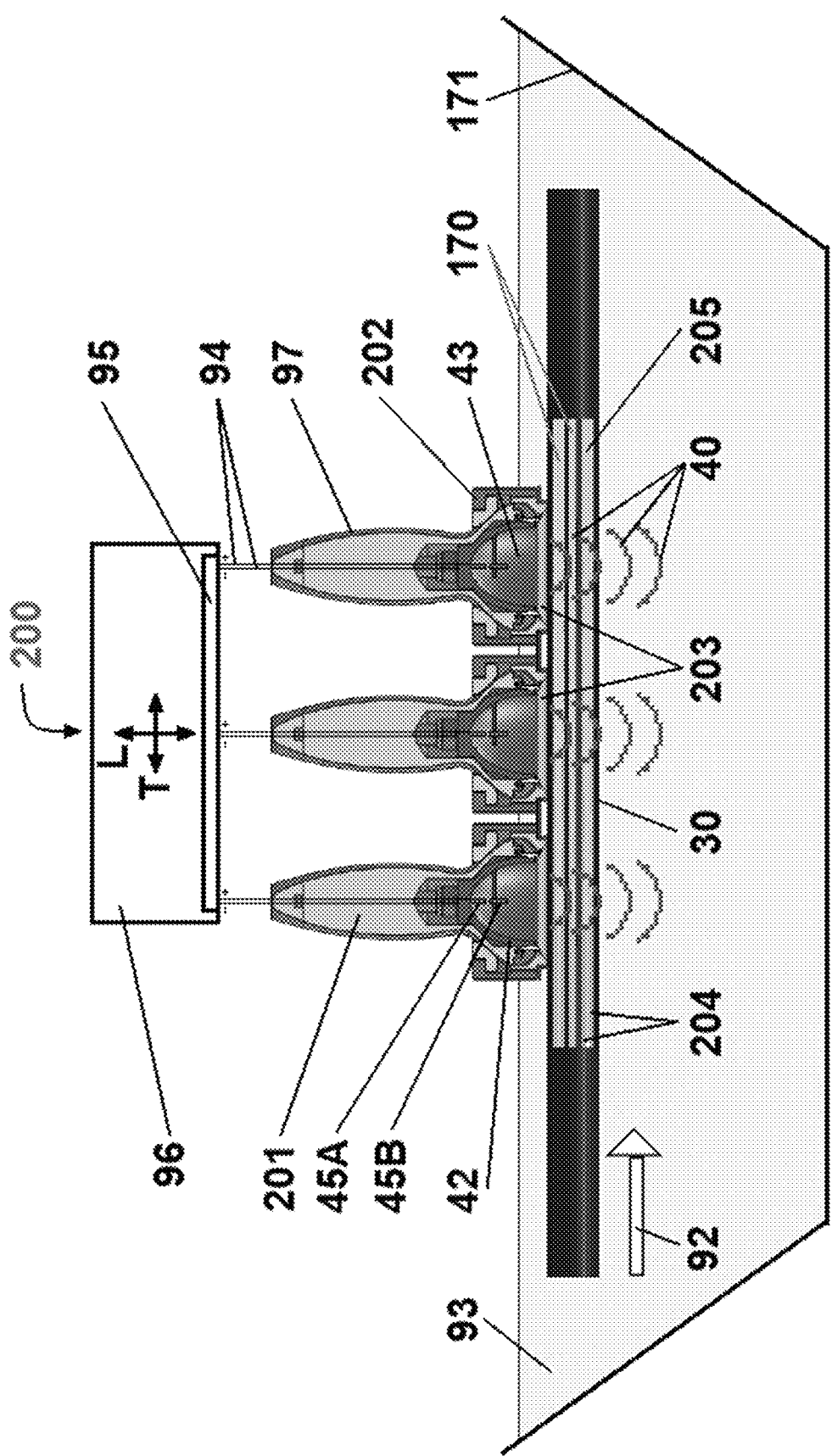
FIG. 20B is a cross-sectional view of FIG. 20A for a manual or semi-automatic system for cleaning and high-level disinfection of endoscopes using three focused shockwave applicators in direct contact with endoscope, according to one embodiment of the present invention.

FIGS. 20A and 20B present the embodiment of multi-applicator decontamination system 200 that uses applicators 201 for cleaning and decontamination on the full length of medical devices such as endoscopes 30. The increased number of applicators 201 is done to produce higher efficiency of cleaning and decontamination, since the medical tubing (endoscope) 30 passes in front of three consecutive applicators 201, which expedites the whole process. The three applicators 201 are installed into the applicators' fixture 202, which allows the simultaneous movement and positioning of the applicators 201 using the transversal (T) and longitudinal (L) motions. By using highly unidirectional downward focused acoustic pressure shockwaves 40, the dislodging and elimination of the contamination layer/biofilm 204 from the inside of the endoscope channels 170 is produced. To have maximum effects for cleaning and decontamination with focused acoustic pressure shockwaves 40 of the endoscope channels 170, a decontamination fluid 205 is present or continuously circulated inside and through the endoscope channels 170. The applicators 201 use a special applicator/coupling inverted conical membrane 203 that is in close contact and deforms ("hugs") around the surface of the medical tubing (endoscope) 30, which assures an efficient action of the focused acoustic pressure shockwaves 40 inside the lumen or lumens of the endoscope 30 (endoscope channels 170). In this embodiment and the majority of the embodiments presented in the present inventions, the multi-applicator decontamination system 200 is focused on the cleaning and decontamination of the internal lumen of the endoscope channels 170 and less on the endoscope 30 external surface, which in general can be much easier cleaned and high-level disinfected with classic/legacy known methods.

The multi-applicator decontamination system 200 is using the focused acoustic pressure shockwaves 40 that are generated via high voltage discharge produced in between first electrode 45A and the second electrode 45B (electrohydraulic principle using spark gap high voltage discharges) in a fluid present inside each reflector cavity 43. For each applicator 201, the high voltage for the first electrode 45A and the second electrode 45B is provided by the power supply 95 (included in control console/unit 96) via high voltage cable 94. The two electrodes 45A and 45B are positioned in the first focal point F (forming the spark-gap 41, as presented in FIG. 4) of the semi-ellipsoidal reflectors 42. During high voltage discharge a plasma bubble is generated that expands and collapses transforming the heat into kinetic energy in the form of acoustic pressure shockwaves that reflect on the semi-ellipsoidal reflector 42, producing the focused acoustic pressure shockwaves 40, which are directed through the applicator/coupling inverted conical membrane 203 towards the focal point $F_2$ of the ellipsoidal geometry and overall to the focal volumes 48 that overlap with the targeted cleaning and high-level disinfection region where the endoscope 30 is present. To be able to properly overlap the focal volumes 48 with the endoscope 30, the transversal (T) and longitudinal (L) motions of the applicators 201 and applicators' fixture 202 are performed manually by the operator or by using semi-automatic or automatic means. Since the focused acoustic pressure shockwaves 40 are produced in a liquid medium, in order to not lose energy through reflections at the change of acoustic impedance from one medium to another and fully take advantage of the micro-jets produced by the collapse of cavitation bubbles, the medical tubing (endoscope) 30 is placed into liquid bath 93 and endoscope channels 170 are filled with a decontamination fluid 205. The liquid bath enclosure 171 of the liquid bath 93 has the proper dimensions to accommodate the applicators 201 and the medical tubing (endoscope) 30 that must stay submerged at all time in the field of action of the applicators 201 and their focal volumes 48 (not shown in FIGS. 20A and 20B) during the cleaning and the high-level disinfection process. Considering the significant length of an endoscope 30, to not increase considerable the dimensions of the bath enclosure 171, the medical tubing (endoscope) 30 after passing in front of the focused acoustic pressure shockwaves 40 and through the focal volumes 48, can exit the liquid bath 93. Similarly, the medical tubing (endoscope) 30 should enter the liquid bath 93 just before passing in front of the focused acoustic pressure shockwaves 40 and through the focal volumes 48. To accomplish that the medical tubing (endoscope) 30 is moving in the tubing/endoscope moving direction 92 and in front of the focused acoustic pressure shockwaves 40.

Although the embodiment presented in FIGS. 20A and 20B shows specifically an electrohydraulic system that uses the spark-gaps 41, the applicators 201 can produce besides focused acoustic pressure shockwaves 40 also pressure waves (pseudo-planar pressure wave 40 or acoustic radial pressure wave 40) and low-frequency ultrasound waves 380 and 381 using electrohydraulic generators with lasers, piezo-electric generators (with piezo crystals/piezo ceramics or piezo fibers) or electromagnetic generators (with flat coils or cylindrical coils).

Figure 21A:
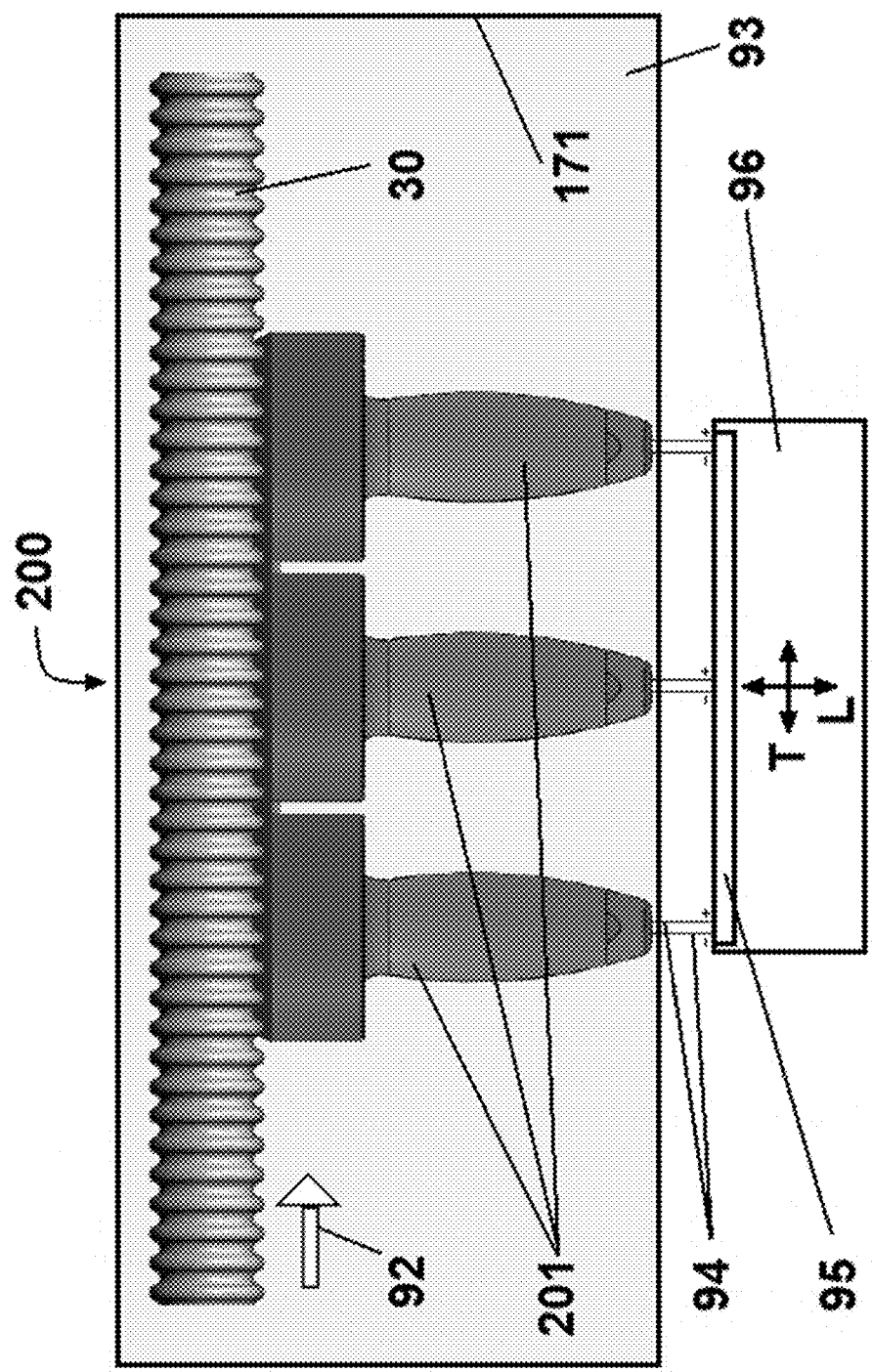
FIG. 21A is a schematic representation of a manual or semi-automatic system for cleaning and high-level disinfection of reusable tubing from ventilators and dialysis machines and other medical devices using three focused shockwave applicators in direct contact with the tubing, according to one embodiment of the present invention.
Figure 21B:
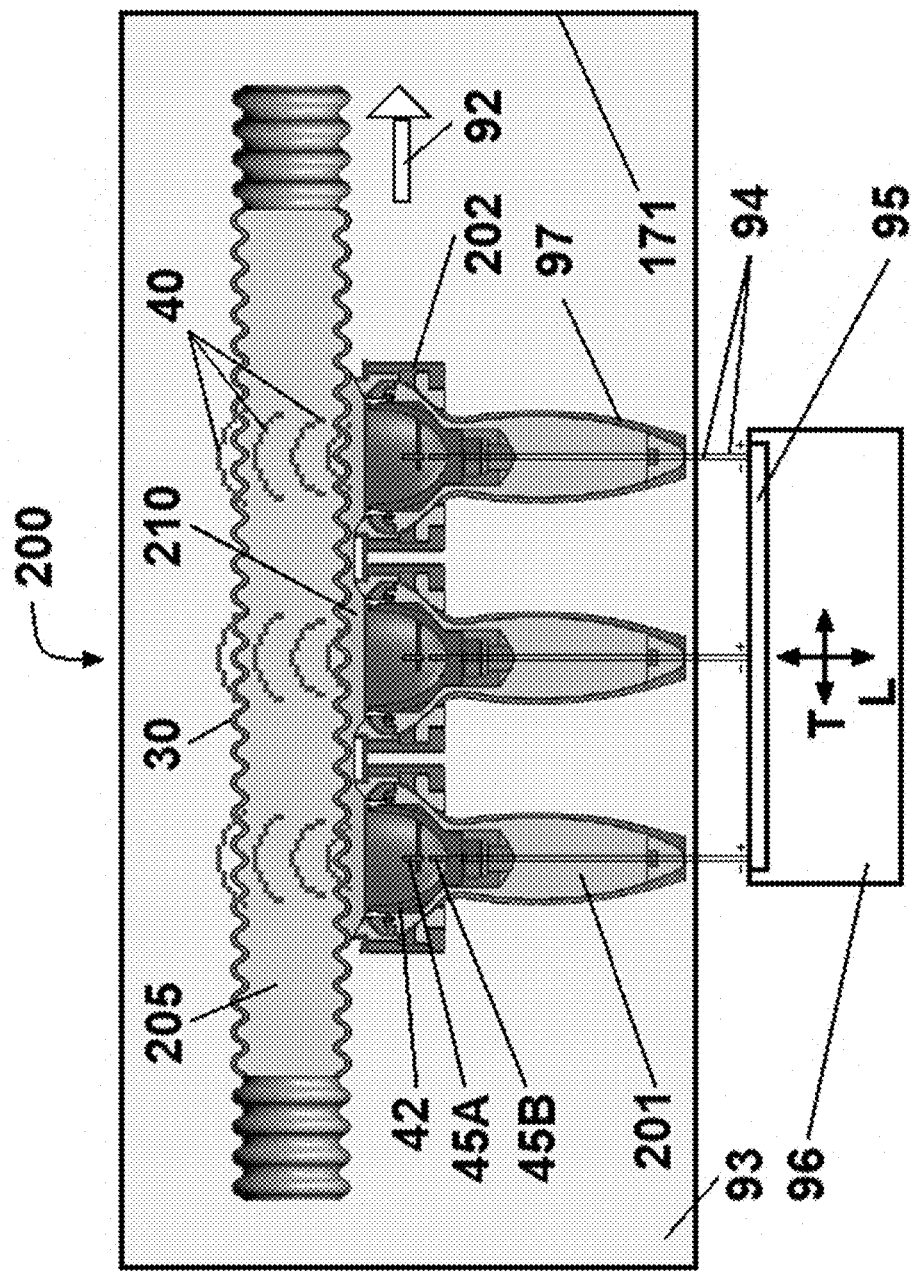
FIG. 21B is cross-sectional view of FIG. 21A for a manual or semi-automatic system for cleaning and high-level disinfection of reusable tubing from ventilators and dialysis machines and other medical devices using three focused shockwave applicators in direct contact with the tubing, according to one embodiment of the present invention.

The embodiment presented in FIGS. 21A and 21B shows multi-applicator decontamination system 200 that uses applicators 201 for cleaning and decontamination on the full length of reusable contaminated tubing 30 from respirators or hemodialysis units or from any other medical devices. The increased number of applicators 201 is done to produce higher efficiency of cleaning and decontamination, since the reusable contaminated tubing 30 passes in front of three consecutive applicators 201, which expedites the whole process. The three applicators 201 are installed into the applicators' fixture 202, which allows the simultaneous movement and positioning of the applicators 201 using the transversal (T) and longitudinal (L) motions. By using highly unidirectional downward focused acoustic pressure shockwaves 40, the dislodging and elimination of the contamination layer/biofilm 204 from the inside of the reusable contaminated tubing 30 is produced. To have maximum effects for cleaning and decontamination with focused acoustic pressure shockwaves 40 of the reusable contaminated tubing 30, a decontamination fluid 205 is present or continuously circulated through its internal lumen/lumens. The applicators 201 use a special multi-applicator coupling membrane 210 that is a common membrane for all three applicators 201 and it is in close contact and deforms ("hugs") around the corrugated surface of the reusable contaminated tubing 30, which assures an efficient action of the focused acoustic pressure shockwaves 40 inside the lumen or lumens of the reusable contaminated tubing 30. In this embodiment, the multi-applicator decontamination system 200 is focused on the cleaning and decontamination of the internal lumen or lumens of the reusable contaminated tubing 30 and less on its external surface, which in general can be much easier cleaned and high-level disinfected with classic/legacy known methods.

The multi-applicator decontamination system 200 is using the focused acoustic pressure shockwaves 40 that are generated via high voltage discharge produced in between first electrode 45A and the second electrode 45B (electrohydraulic principle using spark gap high voltage discharges) in a fluid present inside each reflector cavity 43. For each applicator 201, the high voltage for the first electrode 45A and the second electrode 45B is provided by the power supply 95 (included in control console/unit 96) via high voltage cable 94. The two electrodes 45A and 45B are positioned in the first focal point $F_1$ (forming the spark-gap 41, as presented in FIG. 4) of the semi-ellipsoidal reflectors 42. During high voltage discharge a plasma bubble is generated that expands and collapses transforming the heat into kinetic energy in the form of acoustic pressure shockwaves that reflect on the semi-ellipsoidal reflector 42, producing the focused acoustic pressure shockwaves 40, which are directed through the special multi-applicator coupling membrane 210 towards the focal point $F_2$ of the ellipsoidal geometry and overall to the focal volumes 48 that overlap with the targeted cleaning and high-level disinfection region where the endoscope 30 is present. To be able to properly overlap the focal volume 48 with the reusable contaminated tubing 30, the transversal (T) and longitudinal (L) motions of the applicators 201 and applicators' fixture 202 are performed manually by the operator or by using semi-automatic or automatic means. Since the focused acoustic pressure shockwaves 40 are produced in a liquid medium, in order to not lose energy through reflections at the change of acoustic impedance from one medium to another and fully take advantage of the micro-jets produced by the collapse of cavitation bubbles, the reusable contaminated tubing 30 is placed into liquid bath 93 and its lumen or lumens are filled with a decontamination fluid 205. The liquid bath enclosure 171 of the liquid bath 93 has the proper dimensions to accommodate the applicators 201 and the reusable contaminated tubing 30 that must stay submerged at all time in the field of action of the applicators 201 and their focal volumes 48 (not shown in FIGS. 21A and 21B) during the cleaning and the high-level disinfection process. Considering the significant length of a reusable contaminated tubing 30, to not increase considerable the dimensions of the bath enclosure 171, the reusable contaminated tubing 30 after passing in front of the focused acoustic pressure shockwaves 40 and through the focal volumes 48, can exit the liquid bath 93. Similarly, the reusable contaminated tubing 30 should enter the liquid bath 93 just before passing in front of the focused acoustic pressure shockwaves 40 and through the focal volumes 48. To accomplish that the reusable contaminated tubing 30 is moving in the tubing/endoscope moving direction 92 and in front of the focused acoustic pressure shockwaves 40.

Although the embodiment presented in FIGS. 21A and 21B shows specifically an electrohydraulic system that uses the spark-gaps 41, the applicators 201 can also produce focused acoustic pressure shockwaves 40, or pressure waves (pseudo-planar pressure wave 40 or acoustic radial pressure wave 40), and low-frequency ultrasound waves 380 and 381 using electrohydraulic generators with lasers, piezoelectric generators (with piezo crystals/piezo ceramics or piezo fibers) or electromagnetic generators (with flat coils or cylindrical coils).

Figure 22:
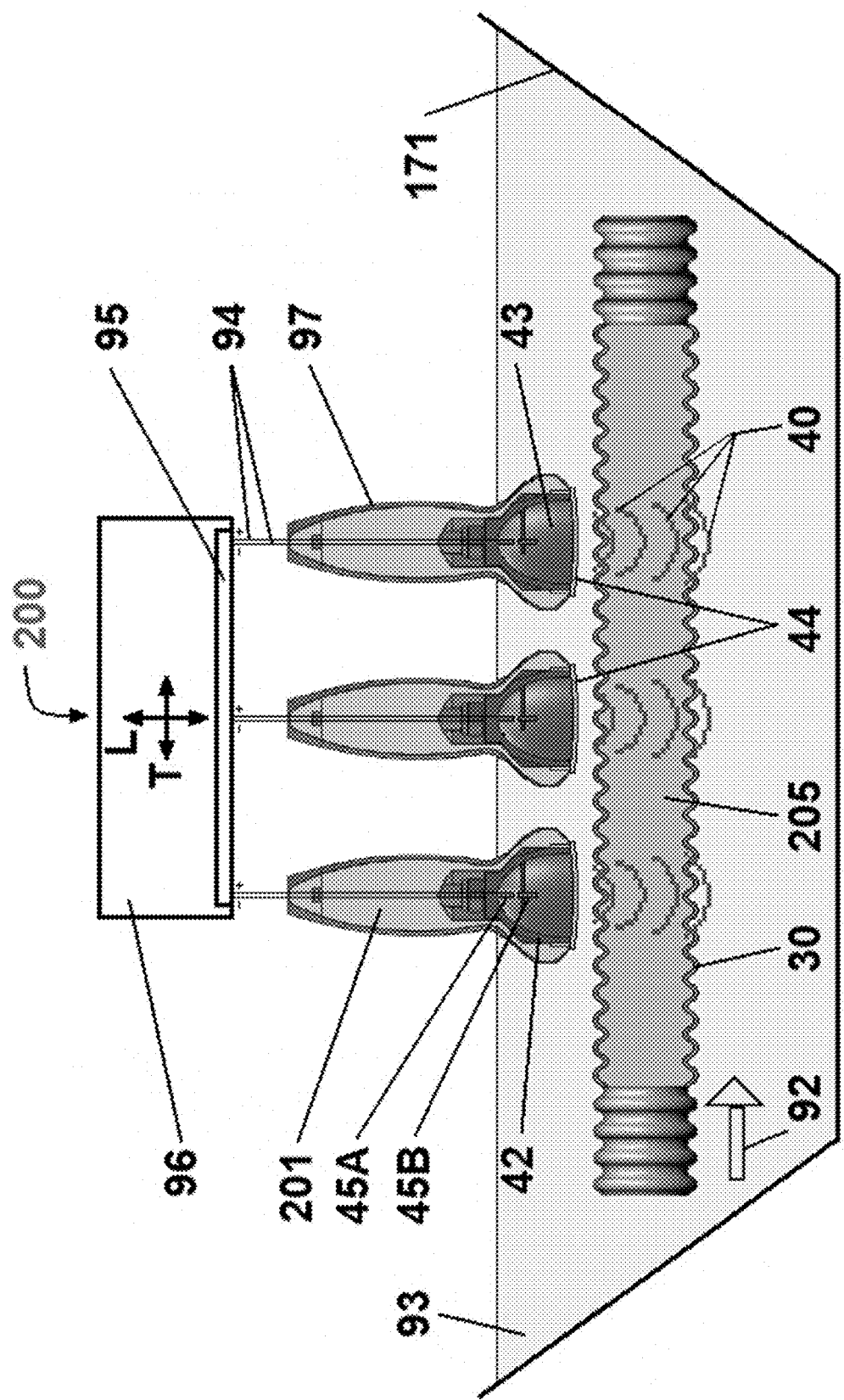
FIG. 22 is a schematic representation of a manual or semi-automatic system for cleaning and high-level disinfection of reusable tubing from ventilators and dialysis machines and other medical devices using three focused shockwave applicators with no direct contact with the tubing, according to one embodiment of the present invention.

If the cleaning and decontamination of both the external surface and the internal lumen or lumens of a reusable contaminated tubing 30 must be accomplished at the same time, then the embodiment from FIG. 22 is used. This approach comes in handy when the external surface of the reusable contaminated tubing 30 is intricate or have texture, as it is the cases with the corrugated reusable contaminated tubing 30 from FIG. 22. Note that the multi-applicator decontamination system 200 has the applicators 201 not in contact with the external surface of the reusable contaminated tubing 30, which allows the action of the compressive forces and the formation of cavitation bubbles both inside and outside the reusable contaminated tubing 30. In this way the cleaning and decontamination can be accomplished successful on both external and internal surfaces of the reusable contaminated tubing 30. As seen in FIG. 22, the applicators 201 can be independent (allows individual flexibility in positioning them around and/or along the reusable contaminated tubing 30) or can be part of an applicators' fixture 202, as presented before in FIGS. 20A-21B. The comments presented before for FIGS. 19A and 19B, related to the positioning around the reusable contaminated tubing 30, and comments from FIGS. 20A-21B, related to construction, positioning along the reusable contaminated tubing 30 and functionality of the multi-applicator decontamination system 200, apply also to the embodiment from FIG. 22.

Although the embodiments from FIGS. 20A-22 shown only three applicators 201, depending on type of device that needs cleaning and decontamination, more than three applicators 201 can be used, which can be deployed around or along the length of an endoscope 30 or a reusable contaminated tubing 30. In this situation, the multi-applicator decontamination system 200 will have applicators 201 capable of being positioned or moved around and along the endoscopes 30 or a reusable contaminated tubing 30 using a manual approach or an automatic fixture that uses multiple step-motors. The positioning of the applicators 201 around and along the endoscopes 30 or a reusable contaminated tubing 30 can follow a certain algorithm dictated by a dedicated software program.

Although the embodiment presented in FIG. 22 shows specifically an electrohydraulic system that uses the spark-gaps 41, the applicators 201 can also produce focused acoustic pressure shockwaves 40, or pressure waves (pseudo-planar pressure wave 40 or acoustic radial pressure wave 40), and low-frequency ultrasound waves 380 and 381 using electrohydraulic generators with lasers, piezoelectric generators (with piezo crystals/piezo ceramics or piezo fibers) or electromagnetic generators (with flat coils or cylindrical coils).

Figure 23:
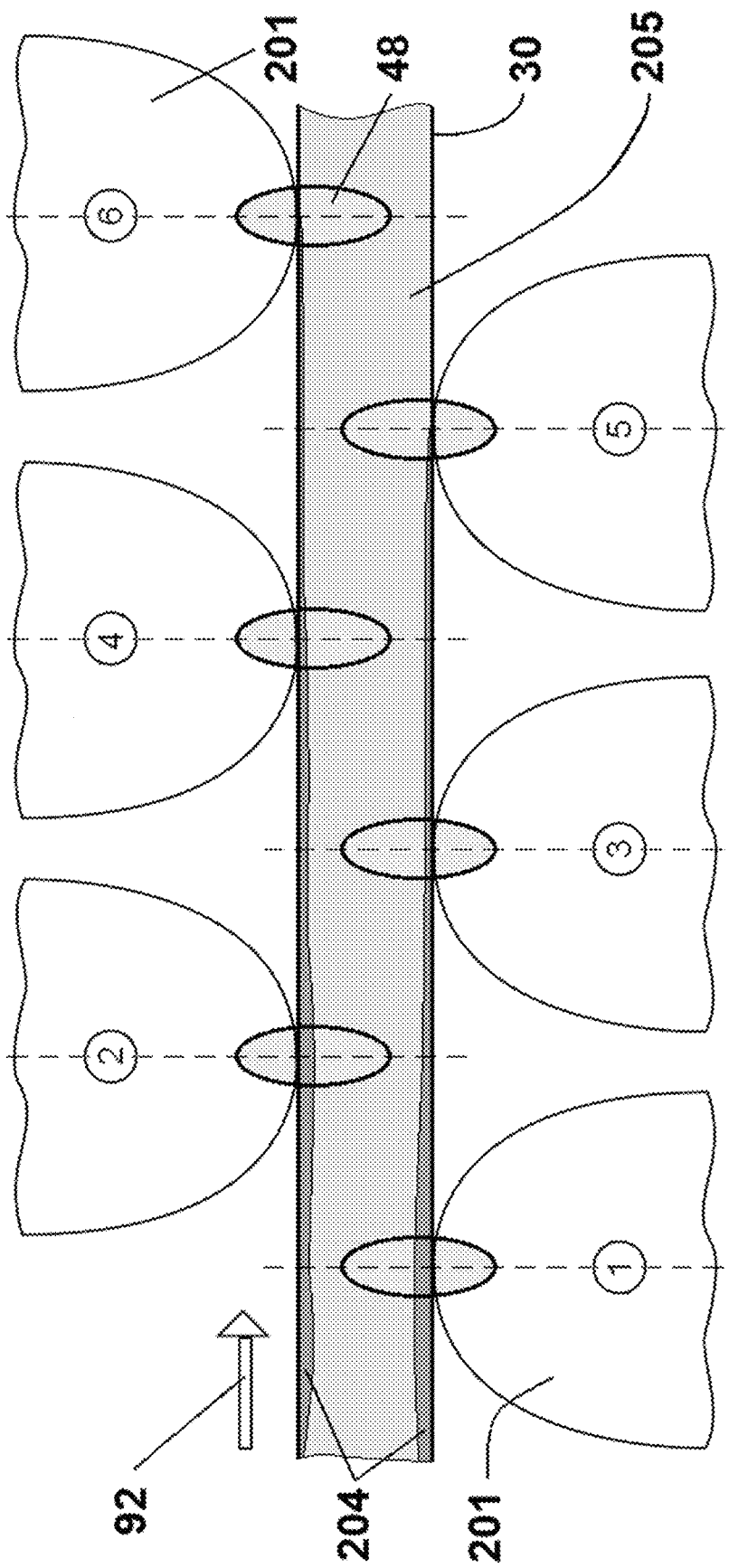
FIG. 23 is a schematic representation of a cleaning and high-level disinfection system for endoscopes or reusable tubing from ventilators and dialysis machines and other medical devices using multiple focused shockwave applicators in direct contact with the endoscope or tubing, according to one embodiment of the present invention.

As seen in the embodiment from FIG. 23, the endoscopes 30 or the reusable contaminated tubing/tubes 30 have a large diameter that does not allow the full diametric coverage by the focal volumes 48 produced by applicators 201 and this is why an alternating placement is needed. For the proper dislodging and elimination of the contamination layer/biofilm 204 from the inside of the endoscope channels 170 (not specifically shown in FIG. 23) or inner lumen or lumens of a reusable contaminated tubing 30, the endoscope 30 or the reusable contaminated tubing 30 is moving in the tubing/endoscope moving direction 92 and in front of the focused acoustic pressure shockwaves 40 (not shown in FIG. 23 for simplicity) and through the focal volumes 48. Since the focused acoustic pressure shockwaves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 is placed into liquid bath 93 and its lumen or lumens are filled with a decontamination fluid 205.

The total number of applicators 201 used in this embodiment is six and they are positioned alternatively on the length of the endoscope 30 or of the reusable contaminated tubing 30 from respirators, hemodialysis units and any other medical devices. Of course, the number of applicators 201 can be lower or higher than six, depending on the specifics of each cleaning and decontamination cycle. In FIG. 23, the applicators 201 are placed alternately on the length of the endoscope 30 or the reusable contaminated tubing 30 and subsequent applicators 201 are at 180 degrees around the endoscope 30 or the reusable contaminated tubing 30. Alternatively, the subsequent applicators 201 can be positioned at 45, 60, 90 or 120 degrees around the endoscope 30 or the reusable contaminated tubing 30. The ultimate solution is where a motorized system can move automatically the applicators 201 in any position desired by the operator or by an automatic system. Regardless of configuration, the most important thing is to cover entirely the whole circumference of the endoscope 30 or the reusable contaminated tubing 30 and along its full length. Any above-mentioned configurations that use the multiple applicators 201 approach can be also applied for valves or other intricate parts or devices that require decontamination, and the applicators 201 need to cover all the "nooks and crannies" of such special parts or components or medical devices.

For FIG. 23 all types of generation principles apply for creating focused acoustic pressure shockwaves 40 such as electrohydraulic with spark-gaps or lasers, piezoelectric with piezo-crystals/piezo-ceramics or piezo fibers, or electromagnetic with cylindrical coils or flat coils. The same generation principles can also be applied to produce pressure waves (pseudo-planar pressure wave 40 or acoustic radial pressure wave 40) and low-frequency ultrasound waves 380 and 381, which are also working to produce the cleaning and decontamination of endoscopes 30 or of the reusable contaminated tubing/tubes 30 with the embodiment from FIG. 23.

Due to increased number of applicators 201 for the embodiments presented in FIGS. 19-23, the foot imprint and height of the liquid bath 93 and associated bath enclosure 171 is increased when compared to the embodiments that use only one applicator 97, as presented in FIGS. 9-18. However, the dimensional increase for the liquid bath 93 and associated bath enclosure 171 and operational complexity, can be justified by the increase in efficiency of cleaning and decontamination that is one of the paramount factors that is pursued by a large operation, which can process a large number of endoscopes 30 or of the reusable contaminated tubing/tubes 30 from respirators, hemodialysis units and any other medical devices. Computer control provides flexibility for the whole cleaning and decontamination system.

Figure 24:
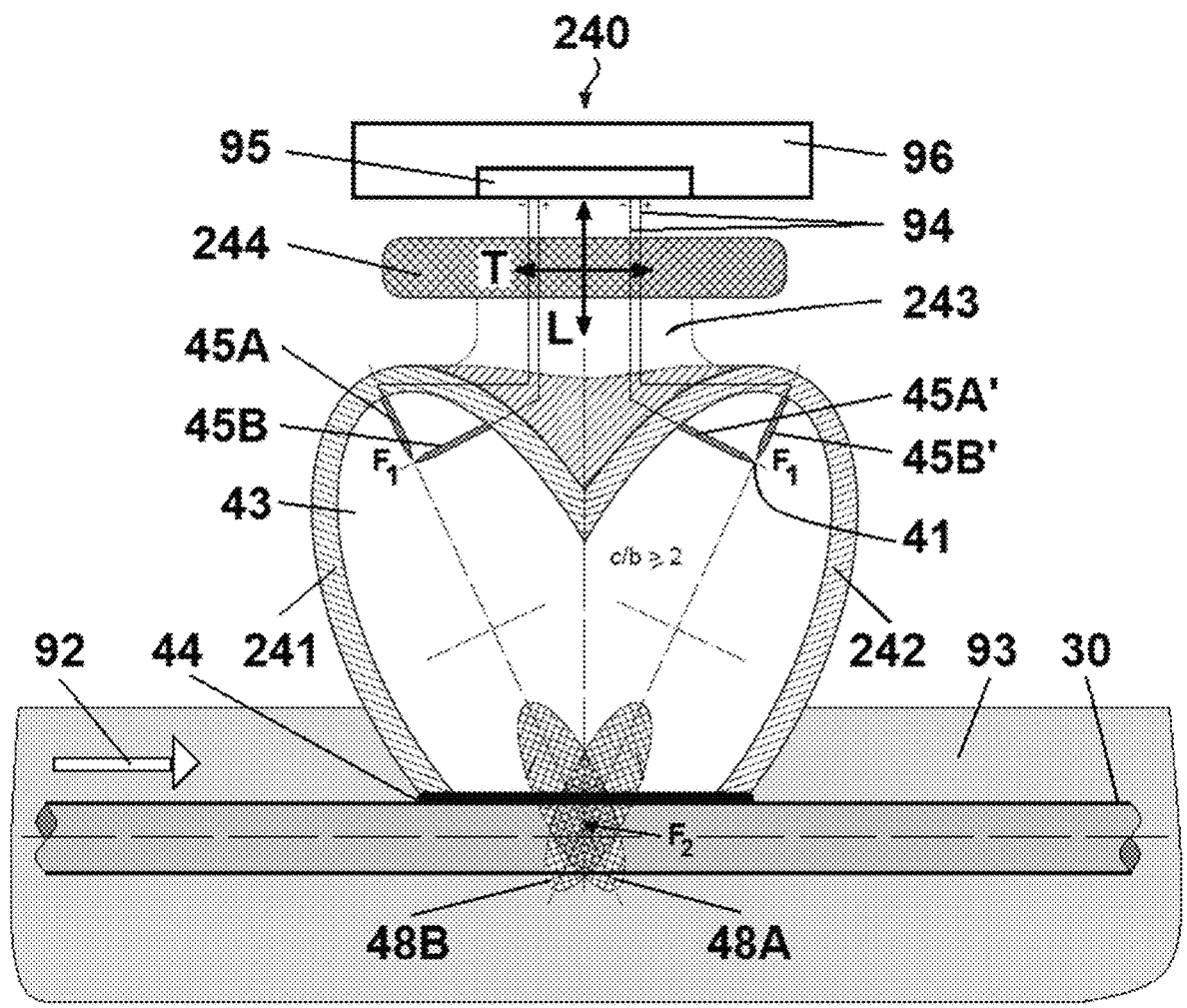
FIG. 24 is a schematic representation of a cleaning and high-level disinfection system for endoscopes or reusable tubing from ventilators and dialysis machines and other medical devices using focused shockwaves applicators having multiple confocal reflectors, according to one embodiment of the present invention.

If reflectors with angled geometries are used for cleaning and decontamination of endoscopes 30 or of the reusable contaminated tubing/tubes 30 from respirators, hemodialysis units and any other medical devices, then the embodiment presented in FIG. 24 can be created. To create the con-focal applicators decontamination system 240, four pieces (first confocal reflector portion 241, second confocal reflector portion 242, con-focal applicator body 243, and con-focal applicators handle 244) are assembled together to achieve the presented reflector cavity 43 used to harbor a fluid in which focused acoustic pressure shockwaves 40 (not shown in FIG. 24 for clarity) are creating two different focal volumes 48A and 48B. The focal volumes (first reflector focal volume 48A and second reflector focal volume 48B) can be confocal and partially overlap to produce more energy for cleaning and decontamination of the endoscopes 30 or of the reusable contaminated tubing/tubes 30 from respirators, hemodialysis units, and any other medical devices, as seen in FIG. 24. Alternatively, the two focal volumes 48A and 48B can be totally separated (without any overlap), but rather adjacent.

To be able to create the embodiment from FIG. 24, only partial ellipsoidal reflectors can be used. To maintain sufficient efficiency and minimal interference in between them, the first confocal reflector portion 241 and the second confocal reflector portion 242 need to be rather deep than shallow. This is why the ratio of the major elliptical semi axis "c" and minor elliptical semi axis "b" (as seen in FIG. 7) for these reflectors should be higher or equal with 2, which is the characteristic of deep ellipsoidal reflectors.

The con-focal applicators decontamination system 240 is using the focused acoustic pressure shockwaves 40 that are generated via high voltage discharge produced in between first electrode 45A and the second electrode 45B of the first confocal reflector portion 241 and the third electrode 45A' and the fourth electrode 45B' of the second confocal reflector portion 242 (electrohydraulic principle using spark gap high voltage discharges) in a fluid present inside each reflector cavity 43. For applicators 241 and 242, the high voltage for the electrodes 45A, 45B, 45A', and 45B' is provided by the power supply 95 (included in control console/unit 96) via high voltage cable 94. The two electrodes 45A and 45B are positioned in the first focal point $F_1$ of the first confocal reflector portion 241 and the third and fourth electrodes 45A' and 45B' are positioned in the first focal point $F_1$ of the second confocal reflector portion 242 (forming the spark-gaps 41, as presented in FIG. 4). During high voltage discharge a plasma bubble is generated that expands and collapses transforming the heat into kinetic energy in the form of acoustic pressure shockwaves that reflect on the first confocal reflector portion 241 and the second confocal reflector portion 242, producing the focused acoustic pressure shockwaves 40, which are directed through the applicator/coupling membrane 44 towards the focal point $F_2$, that is common for the two reflectors. The two focal volumes 48A and 48B overlap with the targeted cleaning and high-level disinfection region where the endoscope 30 and the reusable contaminated tubing 30 is present. To be able to properly overlap the focal volumes 48A and 48B with endoscope 30 and the reusable contaminated tubing 30, the transversal (T) and longitudinal (L) motions of the con-focal applicators decontamination system 240 are performed manually by the operator or by using semi-automatic or automatic means. Since the focused acoustic pressure shockwaves 40 are produced in a liquid medium, in order to not lose energy through reflections at the change of acoustic impedance from one medium to another and fully take advantage of the micro-jets produced by the collapse of cavitation bubbles, the endoscope 30 and the reusable contaminated tubing 30 is placed into liquid bath 93 and its lumen or lumens are filled with a decontamination fluid 205 (see FIGS. 20B, 21B, 22 and 23). The liquid bath 93 has the proper dimensions to accommodate the con-focal applicators decontamination system 240 and the endoscope 30 and the reusable contaminated tubing 30 that must stay submerged at all time in the field of action of the con-focal applicators decontamination system 240 and its focal volumes 48A and 48B during the cleaning and the high-level disinfection process. Considering the significant length of an endoscope 30 and of a reusable contaminated tubing 30, to not increase considerable the dimensions of the bath enclosure 171, the endoscope 30 and the reusable contaminated tubing 30 after passing in front of the focused acoustic pressure shockwaves 40 and through the focal volumes 48A and 48B, can exit the liquid bath 93. Similarly, the endoscope 30 and the reusable contaminated tubing 30 should enter the liquid bath 93 just before passing in front of the focused acoustic pressure shockwaves 40 and through the focal volumes 48A and 48B. To accomplish that the endoscope 30 and the reusable contaminated tubing 30 is moving in the tubing/endoscope moving direction 92 and in front of the focused acoustic pressure shockwaves 40.

In certain situations, two or more con-focal applicators decontamination systems 240 can be used for cleaning and decontamination of the endoscopes 30 or of the reusable contaminated tubing 30 from respirators, hemodialysis units and any other medical devices. The positioning of the multiple con-focal applicators decontamination systems 240 can be sequential along the length or angular around the endoscope 30 and the reusable contaminated tubing 30, with the same variations as mentioned for FIGS. 19A, 19B, and 23.

Although the embodiment presented in FIG. 24 shows specifically an electrohydraulic system that uses the spark-gaps 41, the applicators 241 and 242 can also produce focused acoustic pressure shockwaves 40 or pressure waves (pseudo-planar pressure waves 40 or acoustic radial pressure waves 40) and low-frequency ultrasound waves 380 and 381 using electrohydraulic generators with lasers, piezoelectric generators (with piezo crystals/piezo ceramics or piezo fibers) or electromagnetic generators (with flat coils or cylindrical coils).

Figure 25A:
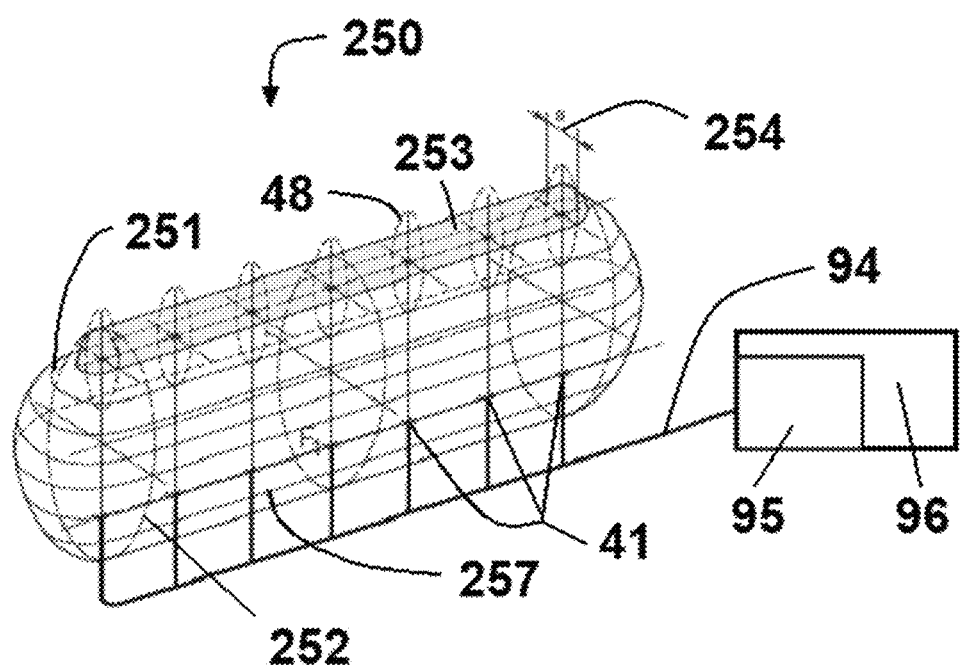
FIG. 25A is a schematic representation of a cleaning and high-level disinfection system for endoscopes or reusable tubing from ventilators and dialysis machines and other medical devices using shockwave elongated applicators having elongated reflectors with multiple spark gaps, according to one embodiment of the present invention.
Figure 25B:
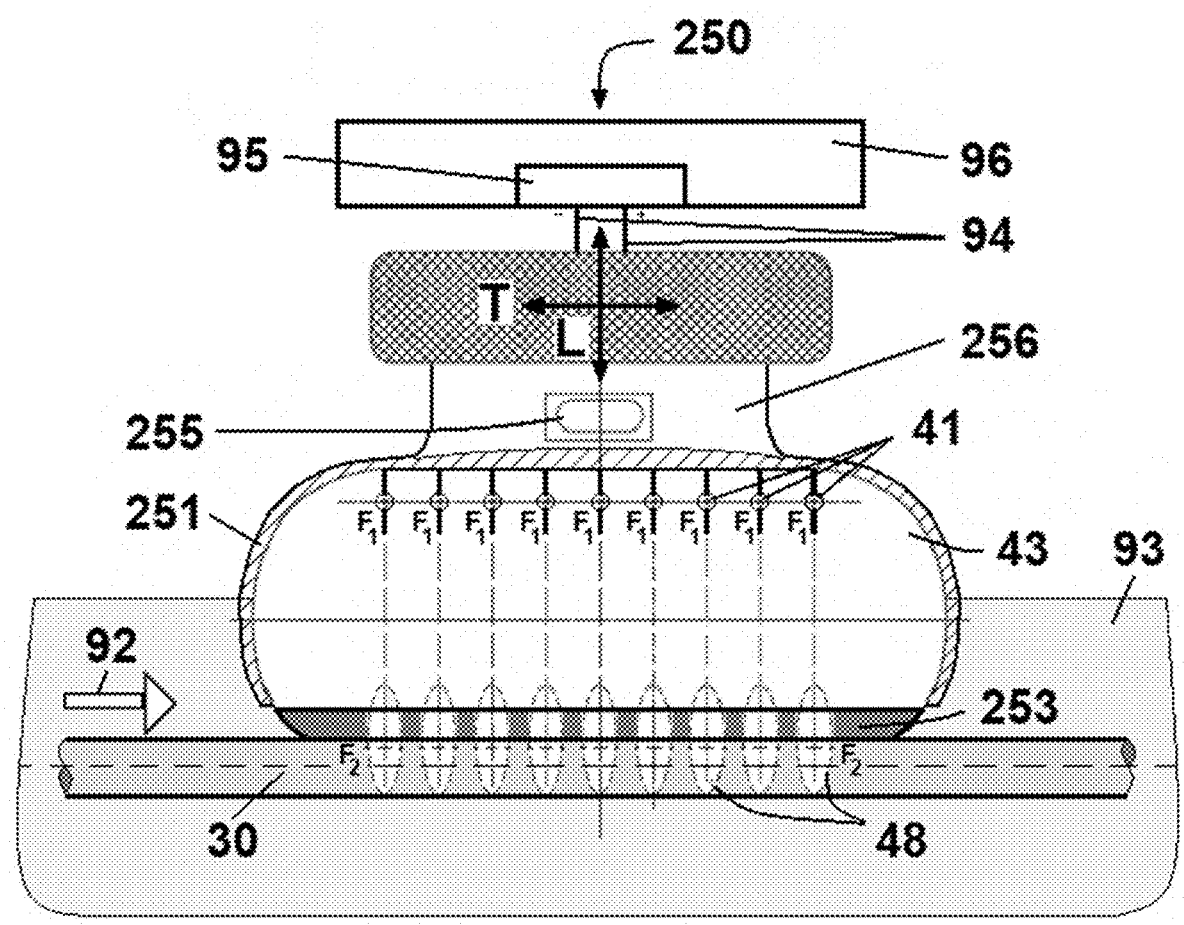
FIG. 25B is cross-sectional view of FIG. 25A showing the cleaning and high-level disinfection system for endoscopes or reusable tubing from ventilators and dialysis machines and other medical devices using shockwave elongated applicators having elongated reflectors with multiple spark gaps, according to one embodiment of the present invention.

The embodiment presented in FIGS. 25A and 25B, is using a decontamination system with elongated applicator 250 that incorporates the special elongated reflector 251. The decontamination system with elongated applicator 250 can increase efficiency of cleaning and decontamination of the endoscopes 30 and of the reusable contaminated tubing 30 from respirators, hemodialysis units, and any other medical devices, by triggering/producing focused acoustic pressure shockwaves 40 in multiple $F_1$ (spark-gaps 41) of the special elongated reflector 251. Based on the needs of the treatment, the high-voltage discharge at the spark-gaps 41 level can be done in the same time or sequential using a shockwave generator or control console/unit 96. Due to the sophistication necessary for the selective activation of the spark-gaps 41, the electric power is provided by the power supply 95 via the high voltage cable 94 and the activation commands are provided by the control console 96. The cross section of the reflecting surface 257 of the special elongated applicator 251 can be an elliptic cross-section 252 (as presented in FIG. 25A) or can be a parabola, a circle or any combination of these geometries, when besides focused acoustic pressure shockwaves 40 also pressure waves as pseudo-planar pressure wave 40 or acoustic radial pressure wave 40, or unfocused pressure waves are generated. The actuation/control of the decontamination system with elongated applicator 250 can be done using the actuation button 255 (as presented in FIG. 25B). The reflecting surface 257 can be also created using piezoelectric elements as piezo crystal s/piezo ceramics, thin films or piezo fibers. The reflector aperture 254 of the elongated applicator 251 is narrow and accommodates the narrow coupling membrane 253, creating the reflector cavity 43. The dimensions of the reflector aperture 254 and of the narrow coupling membrane 253 that sits on top of the reflector aperture 254, it is comparable or larger than the diametric dimension of the endoscopes 30 or of the reusable contaminated tubing 30, to assure a complete and efficient cleaning and decontamination.

The decontamination system with elongated applicator 250 is using the focused acoustic pressure shockwaves 40 (not shown in FIG. 25A or 25B for simplicity) that are generated via high voltage discharge produced in between electrodes that form the spark-gaps 41 (electrohydraulic principle using spark gap high voltage discharges) in a fluid present inside the cavity 43 of the special elongated reflector 251. For the special elongated reflector 251, the high voltage for the electrodes is provided by the power supply 95

(included in control console/unit 96) via high voltage cable 94. During high voltage discharge a plasma bubble is generated that expands and collapses transforming the heat into kinetic energy in the form of acoustic pressure shockwaves that reflect on the special elongated reflector 251, producing the focused acoustic pressure shockwaves 40, which are directed through the narrow coupling membrane 253 towards the focal points $F_2$. The multiple focal volumes 48 overlap with the targeted cleaning and high-level disinfection region where the endoscope 30 and the reusable contaminated medical tubing 30 is present. To be able to properly overlap the focal volumes 48 with endoscope 30 and the reusable contaminated tubing 30, the transversal (T) and longitudinal (L) motions of the decontamination system with elongated applicator 250 are performed manually by the operator or by using semi-automatic or automatic means. Since the focused acoustic pressure shockwaves 40 are produced in a liquid medium, in order to not lose energy through reflections at the change of acoustic impedance from one medium to another and fully take advantage of the micro-jets produced by the collapse of cavitation bubbles, the endoscope 30 and the reusable contaminated tubing 30 is placed into liquid bath 93 and its lumen or lumens are filled with a decontamination fluid 205 (see FIGS. 20B, 21B, 22 and 23). The liquid bath 93 has the proper dimensions to accommodate the decontamination system with elongated applicator 250 and the endoscope 30 and the reusable contaminated tubing 30 that must stay submerged at all time in the field of action of the decontamination system with elongated applicator 250 and its focal volumes 48 during the cleaning and the high-level disinfection process. Considering the significant length of an endoscope 30 and of a reusable contaminated tubing 30, to not increase considerable the dimensions of the liquid bath 93, the endoscope 30 and the reusable contaminated tubing 30 after passing in front of the focused acoustic pressure shockwaves 40 and through the focal volumes 48, can exit the liquid bath 93. Similarly, the endoscope 30 and the reusable contaminated tubing 30 should enter the liquid bath 93 just before passing in front of the focused acoustic pressure shockwaves 40 and through the focal volumes 48. To accomplish that the endoscope 30 and the reusable contaminated tubing 30 is moving in the tubing/endoscope moving direction 92 and in front of the focused acoustic pressure shockwaves 40.

In certain situations, two or more decontamination systems with elongated applicator 250 can be used for cleaning and decontamination of the endoscopes 30 or of the reusable contaminated tubing 30 from respirators, hemodialysis units and any other medical devices. The positioning of the multiple decontamination systems with elongated applicator 250 can be sequential along the length or angular around the endoscope 30 and the reusable contaminated tubing 30, with the same variations as mentioned for FIGS. 19A, 19B, 23, and 24.

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the decontamination system with elongated applicator 250 moves and sometimes both, using manually or motorized automatic means. In FIG. 25B the endoscope 30, or reusable contaminated tubing 30 from respirators or hemodialysis units or from any other medical devices is moving in the tubing/endoscope moving direction 92 and in front of the focused acoustic pressure shockwaves 40.

Figure 26:
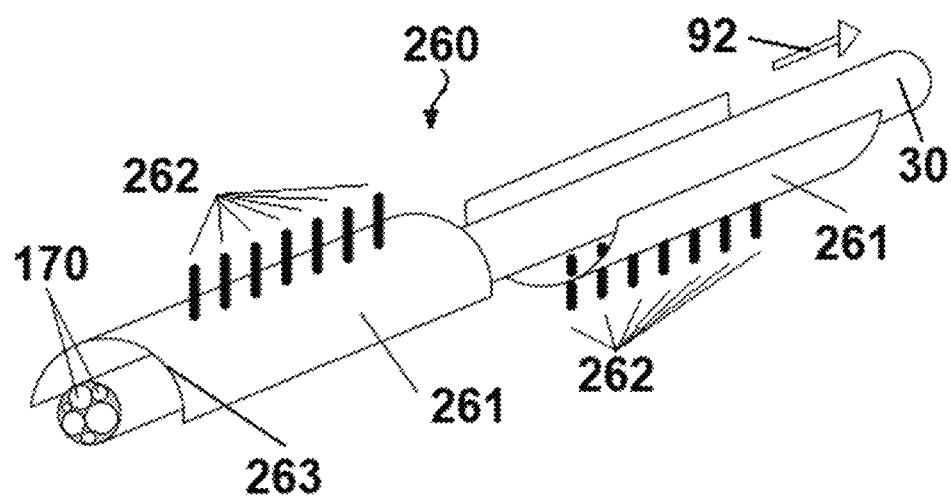
FIG. 26 is a schematic representation of a cleaning and high-level disinfection system for endoscopes or reusable tubing from ventilators and dialysis machines and other medical devices using shockwave applicators or pressure wave applicators having pipe reflectors with multiple spark gaps, according to one embodiment of the present invention.

FIG. 26 shows a decontamination system with pipe reflectors 260 that is using pipe reflectors 261. A pipe reflector 261 is made of a hypotube (thin metal tube) shaped in the form of a pipe with a cross-section 263 (such as elliptical, parabolic or combination semi-spherical and conical), which are used to focus the focused acoustic pressure shockwaves 40, or direct the pseudo-planar pressure waves 40, or acoustic radial pressure waves 40, or unfocused pressure waves 40 generated by the high voltage discharge in the discharge points 262. The elliptical cross-section 263 for the pipe reflector 261 can focus away focused acoustic pressure shockwaves 40 generated by the discharge points 262 towards the focal volumes 48 (not shown in FIG. 26) that intersect and overlap with the endoscopes 30 or of the reusable contaminated tubing 30 from respirators, hemodialysis units and any other medical devices. If the endoscopes 30 or the reusable contaminated tubing 30 are placed before the focal volumes 48, then they are subject to the unfocused pressure waves. When a parabolic cross-section 263 is used for the pipe reflector 261, the discharge points 262 represent the parabolic focal points (seen before in FIG. 5) and pseudo-planar pressure waves 40 will be generated outside the pipe reflector 261 and create the pseudo-planar waves pressure field 55 (see FIG. 5) that must overlap with the endoscopes 30 or of the reusable contaminated tubing 30 from respirators, hemodialysis units and any other medical devices. When a combination semi-spherical and conical cross section 263 is used for the pipe reflector 261, the discharge points 262 represent the sphere central point (seen before in FIG. 6) and acoustic radial pressure waves 40 will be generated outside the pipe reflector 261 and create the radial waves pressure field 63 (see FIG. 6) that must overlap with the endoscopes 30 or of the reusable contaminated tubing 30 from respirators, hemodialysis units and any other medical devices. The actual example depicted in FIG. 26 is an endoscope, and thus the endoscope channels 170 are shown that are usually filled with a decontamination fluid 205 (not specifically shown in FIG. 26) during the cleaning and decontamination process.

The discharge points 262 of the pipe reflector 261 can be all activated simultaneously or subsequently, and in other cases, only selective discharge points or individual points can be activated to match the specific requirements of the cleaning and decontamination process of the endoscopes 30 or of the reusable contaminated tubing 30 from respirators, hemodialysis units and any other medical devices. Due to the sophistication necessary for the selective activation of the discharge points 262, the electric power is provided by the power supply 95 via the high voltage cable 94 and the activation commands are provided by the control console 96 (elements not specifically shown in FIG. 26).

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the decontamination system with pipe reflectors 260 moves and sometimes both, using manually or motorized automatic means. In FIG. 26 the endoscope 30, or reusable contaminated tubing 30 from respirators or hemodialysis units or from any other medical devices is moving in the tubing/endoscope moving direction 92 and in front of the focused acoustic pressure shockwaves 40, or direct the pseudo-planar pressure waves 40, or acoustic radial pressure waves 40, or unfocused pressure waves.

Although the embodiment presented in FIG. 26 shows specifically an electrohydraulic system that uses the spark-gaps 41, the decontamination system with pipe reflectors 260 can also produce focused acoustic pressure shockwaves 40 or pressure waves (pseudo-planar pressure waves 40 or acoustic radial pressure waves 40) and low-frequency ultrasound waves 380 and 381 using electrohydraulic generators with lasers, piezoelectric generators (with piezo crystals/piezo ceramics or piezo fibers) or electromagnetic generators (with flat coils or cylindrical coils).

Figure 27:
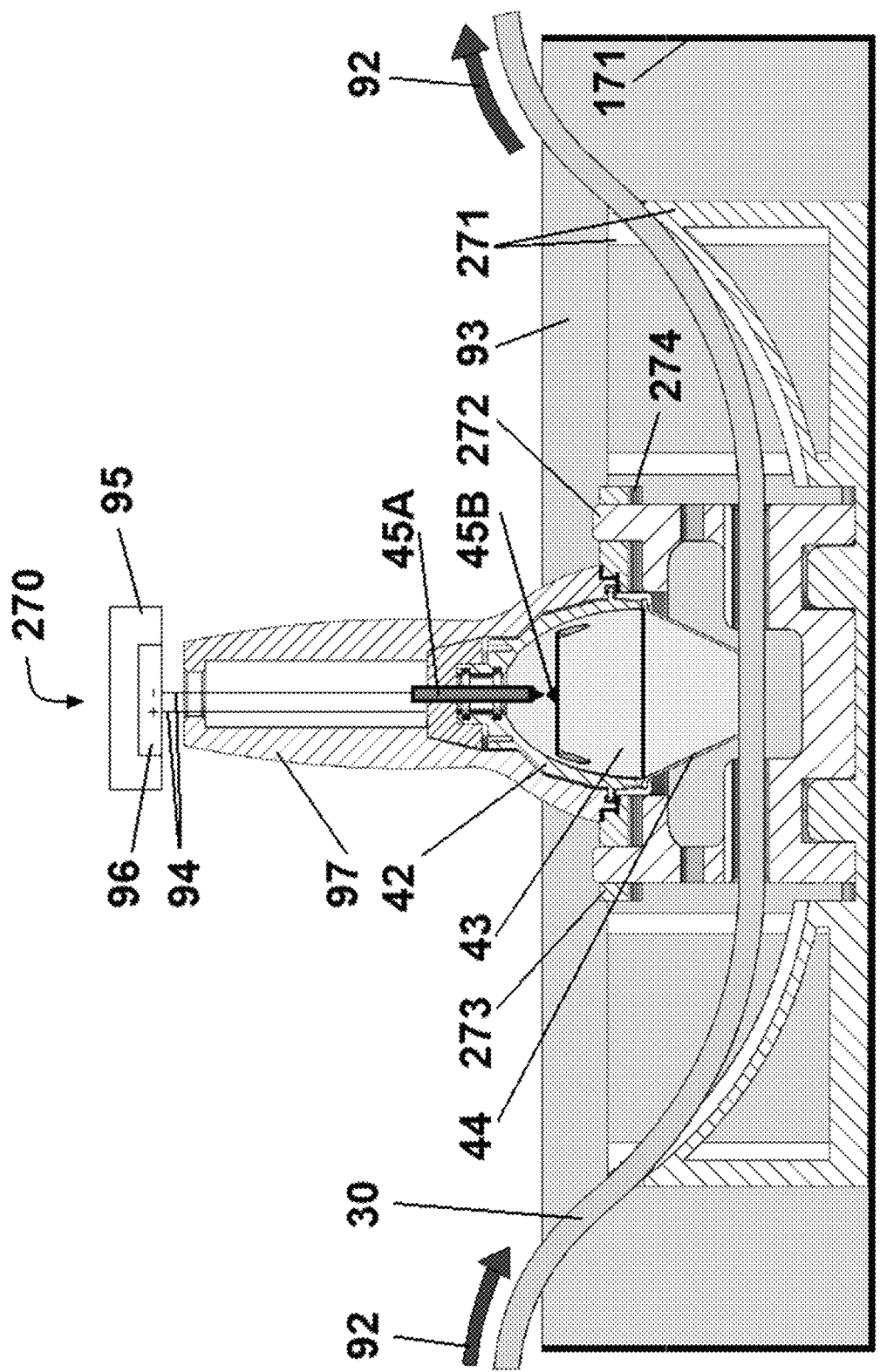
FIG. 27 is a schematic cross-sectional view of a fixture for manual or semi-automatic cleaning and high-level disinfection of endoscopes or reusable tubing from ventilators and dialysis machines and other medical devices using focused shockwave applicators or pressure wave applicators, according to one embodiment of the present invention.

The embodiment from FIG. 27 shows a cross-section of a manual/semi-automatic decontamination system 270 using a single applicator 97 for cleaning and decontamination of endoscopes 30 or of the reusable contaminated tubing 30 from respirators, hemodialysis units and any other medical devices. As mentioned before for FIGS. 20A-21B and 24-25B, to not increase considerable the dimensions of the liquid bath 93 and associated liquid bath enclosure 171, the endoscope 30 and the reusable contaminated tubing 30 can enter and exit the liquid bath 93 immediately before and after passing in front of the focused acoustic pressure shockwaves 40 or pseudo-planar pressure waves 40 or acoustic radial pressure waves 40 or unfocused pressure waves. To accomplish that the endoscope 30 and the reusable contaminated tubing 30 is moving in the tubing/endoscope moving direction 92 using the guiding semi-channel fixture 271. In the design of the manual/semi-automatic decontamination system 270, the guiding semi-channel fixture 271 is completed integrated (one part) with the bath enclosure 171. The applicator 97 is positioned in a fixed position using the applicator supporting fixture 272. To accommodate different dimensions of the endoscopes 30 or of the reusable contaminated tubing 30 from respirators, hemodialysis units and any other medical devices, the vertical positioning of the applicator 97 can be adjusted via the shims 274 that are placed beneath the applicator depth adjusting part 273, which are practically moving the whole applicator supporting fixture 272 up and down.

To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicator 97 moves and sometimes both, using manually or motorized automatic means. In FIG. 27 the endoscope 30 or reusable contaminated tubing 30 from respirators or hemodialysis units or from any other medical devices is moving in the tubing/endoscope moving direction 92 and in front of the focused acoustic pressure shockwaves 40 or pseudo-planar pressure waves 40 or acoustic radial pressure waves 40 or unfocused pressure waves. The applicator 97 is in direct contact with the endoscope 30 or reusable contaminated tubing 30 (via the applicator/coupling membranes 44), which assures an efficient action on the lumen or lumens of the endoscope 30 or reusable contaminated tubing 30. In this embodiment presented in FIG. 27, the manual/semi-automatic decontamination system 270 is focused on the cleaning and decontamination of the internal lumen or lumens of the reusable contaminated medical tubing 30 and less on its external surface, which in general can be much easier cleaned and high-level disinfected with classic/legacy known methods.

In FIG. 27, the manual/semi-automatic decontamination system 270 is using the focused acoustic pressure shockwaves 40 or pseudo-planar pressure waves 40 or acoustic radial pressure waves 40 or unfocused pressure waves that are generated via high voltage discharge produced in between first electrode 45A and the second electrode 45B (electrohydraulic principle using spark-gap high voltage discharges) in a fluid present inside the reflector cavity 43. The high voltage for the first electrode 45A and the second electrode 45B is provided by the power supply 95 (included in control console/unit 96) via high voltage cable 94. The two electrodes 45A and 45B are positioned in the first focal point $F_1$ (focal point 47 where the spark-gap 41 is positioned, as presented in FIG. 4) of the semi-ellipsoidal reflector 42 (for producing focused acoustic pressure shockwaves 40 or unfocused pressure waves) or in the parabolic focal point (see FIG. 5) of the parabolic reflector 51 (for producing pseudo-planar pressure waves 40) or the central sphere point (see FIG. 6) of the combination semi-spherical and conical reflector 61 (for producing acoustic radial pressure waves 40). During high voltage discharge a plasma bubble is generated that expands and collapses transforming the heat into kinetic energy in the form of shockwaves or pressure waves that reflect on the semi-ellipsoidal reflector 42, or on the parabolic reflector 51, or on the combination semi-spherical and conical reflector 61 producing focused acoustic pressure shockwaves 40, or unfocused pressure waves, or pseudo-planar pressure waves 40, or acoustic radial pressure waves 40, which are directed through the applicator/coupling membrane 44 towards the targeted cleaning and high-level disinfection region where the endoscope 30 or the reusable contaminated tubing 30 is present. To be able to properly overlap the focal volume 48 (see FIG. 4) or the pseudo-planar waves pressure field 55 (see FIG. 5) or the radial waves pressure field 63 (see FIG. 6) with the endoscope 30 or the reusable contaminated tubing 30, the applicator supporting fixture 272 and the shims 274 are used. Since the focused acoustic pressure shockwaves 40, or pseudo-planar pressure waves 40, or acoustic radial pressure waves 40 are produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 is placed into liquid bath 93 of the liquid bath enclosure 171 and its lumen or lumens are filled with a decontamination fluid 205 (see FIGS. 20B, 21B, 22 and 23).

Although the embodiment presented in FIG. 27 shows specifically an electrohydraulic system that uses the spark-gap 41, the applicator 97 can also produce focused acoustic pressure shockwaves 40 or pressure waves (pseudo-planar pressure wave 40 or acoustic radial pressure wave 40 or unfocused pressure waves) and low-frequency ultrasound waves 380 and 381 using electrohydraulic generators with lasers, piezoelectric generators (with piezo crystals/piezo ceramics or piezo fibers) or electromagnetic generators (with flat coils or cylindrical coils).

Figure 28B:
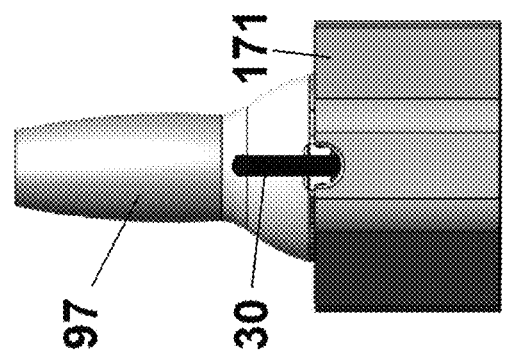
FIGS. 28A-C are 3D schematic representations of the fixture shown in FIG. 27 for manual or semi-automatic cleaning and high-level disinfection of endoscopes or reusable tubing from ventilators and dialysis machines and other medical devices using focused shockwave applicators or pressure wave applicators, according to one embodiment of the present invention.
Figure 28A:
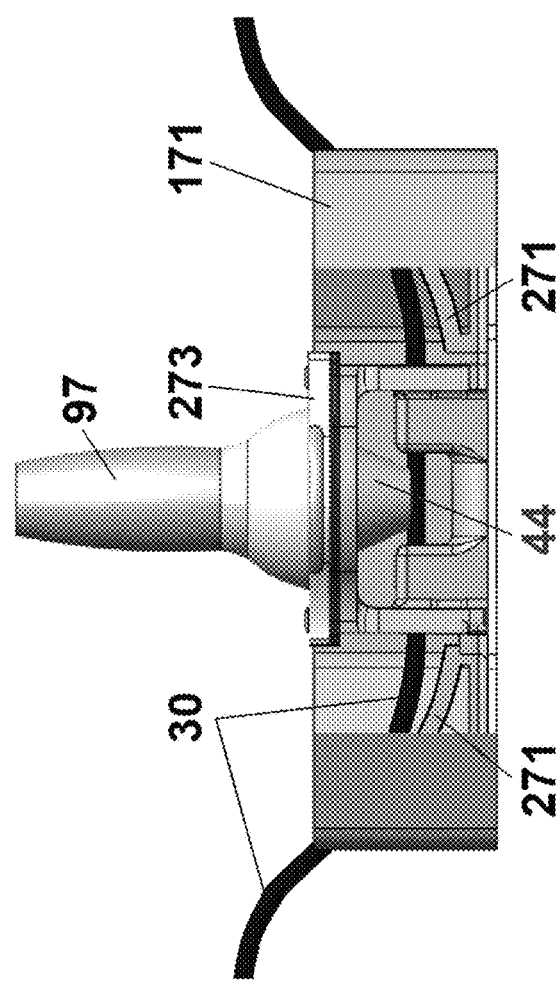
Figure 28C:
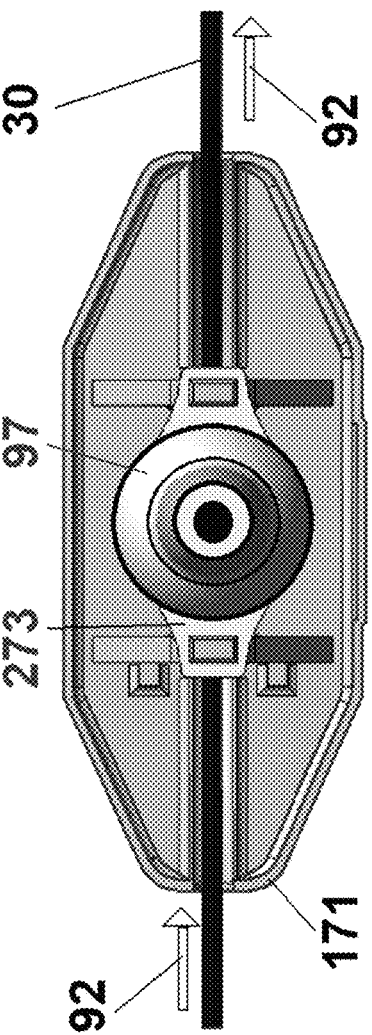

FIGS. 28A, 28B, and 28C show multiple three-dimensional views of the manual/semi-automatic decontamination system 270 that was presented in detail and its specific functioning described before in FIG. 27. In FIGS. 28A, 28B, and 28C all the elements and their numerical depiction are the same as those from FIG. 27.

Figure 29B:
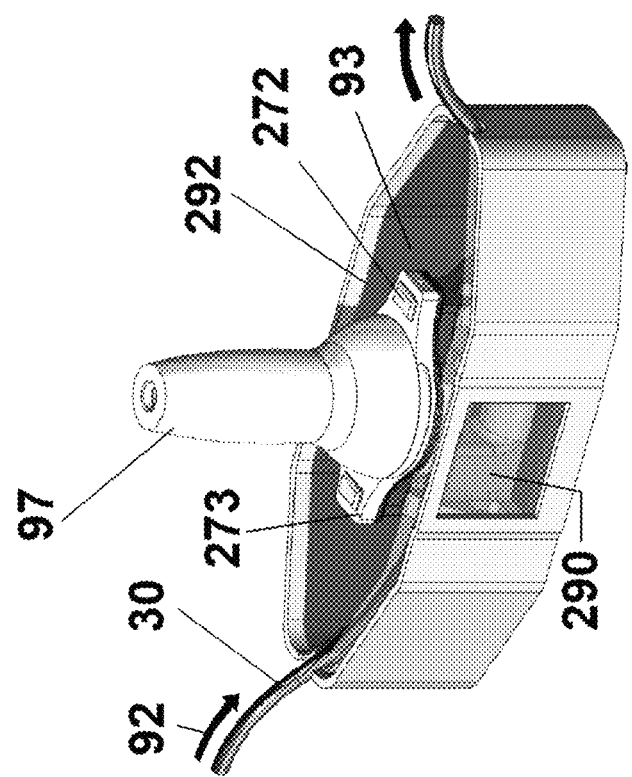
FIGS. 29A and 29B are schematic 3D blow-out representations of the fixture from FIGS. 27 and 28A-28C for manual or semi-automatic cleaning and high-level disinfection of endoscopes or reusable tubing from ventilators and dialysis machines or and medical devices using focused shockwave applicators and pressure wave applicators, according to one embodiment of the present invention.
Figure 29A:
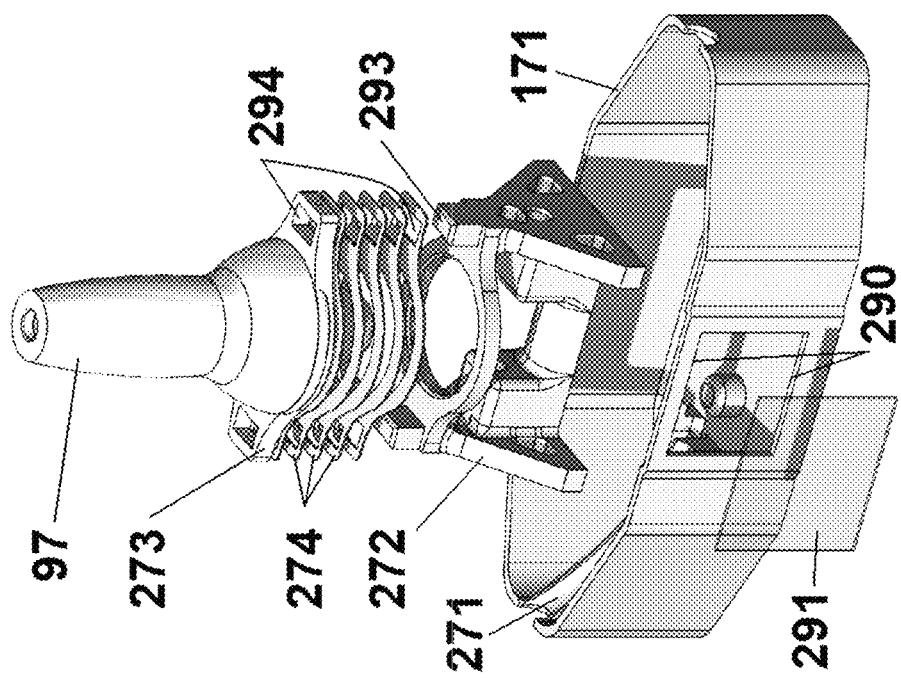

To see better in three-dimensional fashion some of details and components of the manual/semi-automatic decontamination system 270, in FIGS. 29A and 29B a blow-out representation of the embodiment from FIGS. 27, 28A, 28B, and 28C is presented. Besides the applicator 97, guiding semi-channel fixture 271 that is completely integrated (one part) with the bath enclosure 171, applicator supporting fixture 272, applicator depth adjusting part 273, and the shims 274, there are new elements visible as the visualization window 290, the visualization window plexiglass 291, and the liquid level 292 in the liquid bath 93 of the liquid bath enclosure 171, the tabs 293 of the applicator supporting fixture 272, and the corresponding tab windows 294 for the applicator depth adjusting part 273 and the shims 274. The role of the visualization window 290 and its visualization window plexiglass 230 is to create for the user a window to allow the observation of the proper functioning of the manual/semi-automatic decontamination system 270, especially in the cleaning and decontamination area where a constant contact must be accomplished at all times in between the applicator/coupling membrane 44 of the applicator 97 and the endoscope 30 or the reusable contaminated tubing 30. The continuous observation of the cleaning and decontamination process can be done by a visualization system (not shown in FIGS. 27-29B) that has an appropriate camera and data analysis software. As the matter fact, FIG. 18 represents a snapshot captured by such visualization system during the cleaning and decontamination using the manual/semi-automatic decontamination system 270.

Another advantage of a blow-out view (as presented in FIGS. 29A and 29B) is that it can also show the way the manual/semi-automatic decontamination system 270 can be assembled. Thus, the applicator supporting fixture 272 is first dropped and assembled into the bath enclosure 171 that has integrated in it the guiding semi-channel fixture 271. Then the endoscope 30 or the reusable contaminated tubing 30 is set into the guiding semi-channel fixture 271. Afterwards, the applicator 97 is dropped inside the applicator supporting fixture 272 and correctly positioned relatively to the guiding semi-channel fixture 271 and endoscope 30 or the reusable contaminated tubing 30 using the tabs 293 of the applicator supporting fixture 272 that must enter into the tab windows 294 for the applicator depth adjusting part 273. If the applicator 97 needs vertical adjustment, then the necessary number of shims 274 are assembled on the tabs 293 using their tab windows 294. Then, the applicator depth adjusting part 273 is secured in place to keep the applicator 97 in contact with the endoscope 30 or the reusable contaminated tubing 30, and the manual/semi-automatic decontamination system 270 is filled with appropriate fluid to the liquid level 292 and also a fluid is circulated through the endoscope 30 and the reusable contaminated tubing 30. Finally, the endoscope 30 or the reusable contaminated tubing 30 is connected to the motorized fixture (not shown in FIGS. 27-29B) that produces the constant moving in the tubing/endoscope moving direction 92, the applicator 97 is energized, and the visualization system activated. At this point in time the cleaning and decontamination of the endoscope 30 or the reusable contaminated tubing 30 is in progress. At the end of the cleaning and decontamination process, the manual/semi-automatic decontamination system 270 is disassembled following the same steps but in the reversed order.

Figure 30:
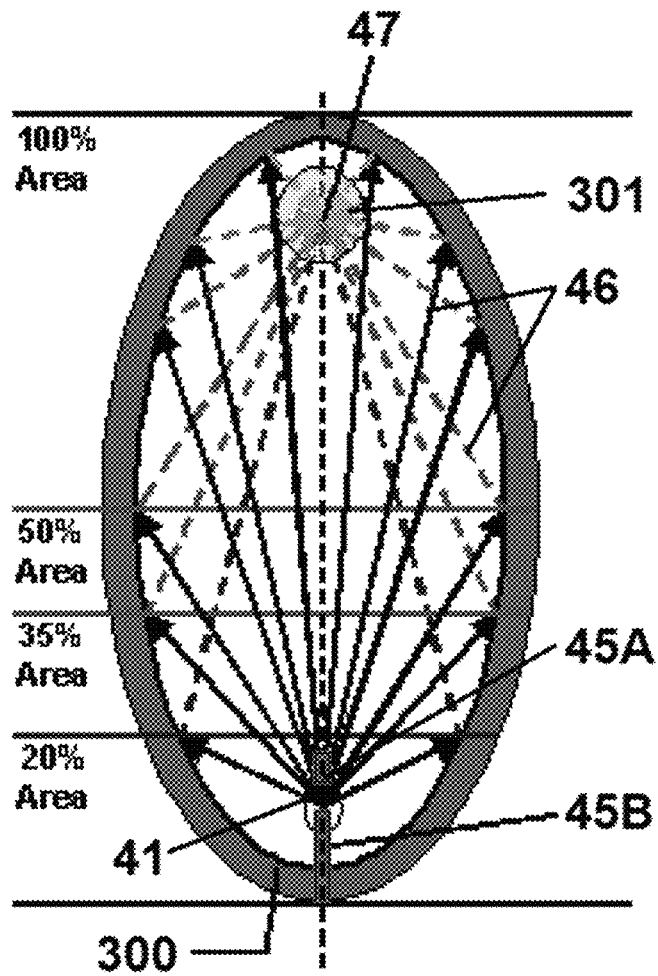
FIG. 30 is a schematic representation of a full ellipsoidal reflector and shockwave focusing relationship known in the prior art.

FIG. 30 presents a full ellipsoidal reflector 300 and the way the shockwave focusing 46 is produced towards the focal point 47. Thus, if a three-dimensional reflector is created in the form of an ellipsoid, the pressure shockwaves generated in the first focal point $F_1$ (where the spark-gap 41 is found) will be reflected with minimal losses by the full ellipsoidal reflector 300 in the second focal point $F_2$, also known as focal point 47. In this situation, the shockwave focusing 46 is done with the whole ellipsoidal surface, which is different from the semi-ellipsoidal reflector 42, when only half of the ellipsoid is used and some portions of the shockwaves are not reflected towards the focal point 47 and they rather continue to propagate divergently away from the focal point 47. This is why a full ellipsoidal reflector 300 had a high efficiency in focusing all shockwave fronts from all directions and collect their energy right around the focal point 47. During shockwave focusing 46, a focal volume 301 is created around $F_2$ (the focal point 47), which has a spherical shape. In the focal volume 301 the maximum shockwave positive pressure 49B are found from the shockwave compressive phase 49D that produces macro effects, together with micro-jets (micro-effect) produced by the collapsing of the cavitation bubbles generated in the shockwave tensile phase 49F, as seen in FIG. 4. In FIG. 30 the shockwaves are produced in a fluid by the high voltage discharge in the spark-gap 41 that is formed by the first electrode 45A and second electrode 45B, which represents the spark-gap electrohydraulic way to produce shockwaves. Other ways to produce shockwaves are using the electromagnetic and piezoelectric principles.

In general, the amount of energy delivered to a targeted region by the shockwaves is directly proportional with the surface area of the reflector. As presented in FIG. 30, in medical pressure shockwave applications the reflectors represent only a percentage of a full ellipsoid (in between 20 to 50% of the area). The more area is used for focusing, the larger the focal volume 301 will be and thus the energy deposited inside the targeted area for shockwave action. This is why a full ellipsoidal reflector 300 that is using all its surface for reflection has the advantage of being more efficient in cleaning and decontamination of endoscopes 30 or the reusable contaminated tubing 30 from respirators, hemodialysis units and any other medical devices.

Figure 31:
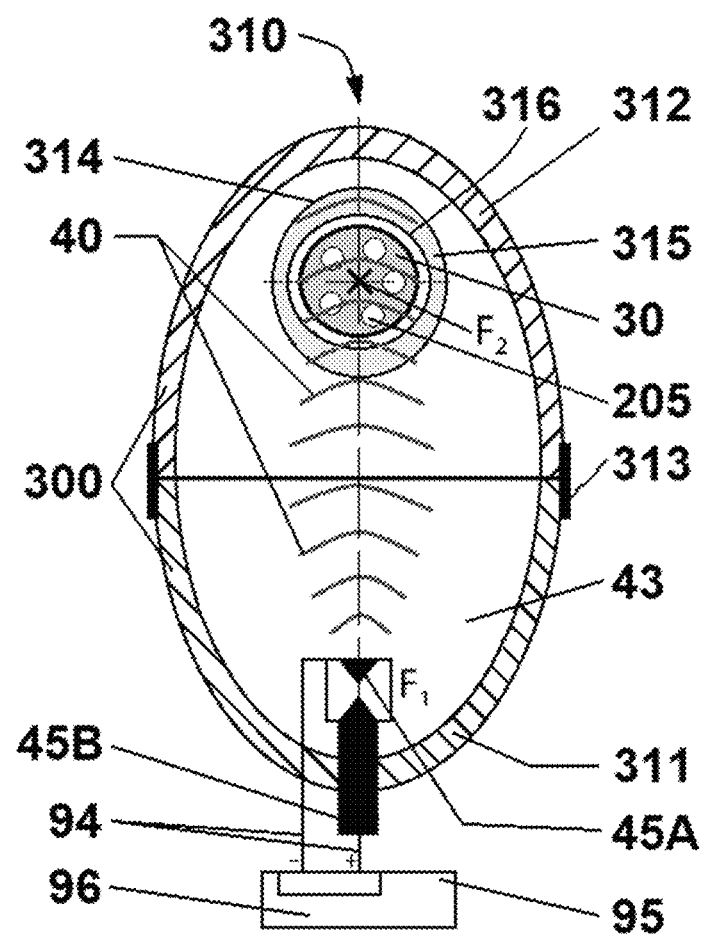
FIG. 31 is a schematic representation of the geometry of a full-ellipsoidal reflector with a channel/opening to move the endoscope or reusable tubing from ventilators and dialysis machines and other medical devices through the focal volume of focused shockwaves during cleaning and high-level disinfection, according to one embodiment of the present invention.

The embodiment from FIG. 31 shows a cross-section of a special full-ellipsoidal applicator 310 that can be used for the cleaning and decontamination of endoscopes 30 or of the reusable contaminated tubing 30 from respirators, hemodialysis units and any other medical devices. Thus, the effective cleaning and decontamination of endoscopes 30 or of the reusable contaminated tubing 30 can be accomplished by designing a special full-ellipsoidal applicator 310 that is made of the lower shell 311 and upper shell 312, which are connected together via the shells connecting ring 313. The special full-ellipsoidal applicator 310 is using deep ellipsoidal reflectors (have a large major elliptical semi axis "c", as defined in FIG. 7) to allow proper shockwave generation and be able to overlap and completely cover with the focal volume 301 (presented in FIG. 30 and not specifically shown in FIG. 31 for simplicity) the entire cross-sectional dimension of the endoscope 30 or of the reusable contaminated tubing 30 that needs cleaning and decontamination. To define a deeper ellipsoidal geometry the ratio in between the major elliptical semi axis "c" and the minor elliptical semi axis "b" (see FIG. 7) should be larger than 1.9 (c/b≥1.9). The dimension of the reflector's largest diameter can be 50-150 mm, preferable 70-140 mm. The input high voltage discharge in $F_1$ (spark-gap 41 formed by the first electrode 45A and second electrode 45B) can be in between 14-30 kV. The high voltage for the first electrode 45A and the second electrode 45B is provided by the power supply 95 (included in control console/unit 96) via high voltage cable 94. The proposed construction of the special full-ellipsoidal applicator 310 is using 90-95% of the ellipsoid (increased reflective area surface), compared with classic approach (semi-ellipsoidal reflector 42 presented for other embodiments) where only 50% of the ellipsoid surface is used to focus the focused acoustic pressure shockwaves 40. The use of 90-95% of the ellipsoidal surface is done by combining a lower shell 311 with a distinctive upper shell 312, that are connected together via the shells connecting ring 313. This design provides a much higher efficiency in shockwave transmission, focusing, and a larger reflector cavity 43, which is filled with a fluid that plays a role in producing, focusing, and transmitting the focused acoustic pressure shockwaves 40 towards the endoscope 30 or the reusable contaminated tubing 30. The upper shell 312 of the special full-ellipsoidal applicator 310 has two upper shell circular openings 314 that are connected with a cylindrical coupling membrane 315 that allows the passing of the endoscope 30 or of the reusable contaminated tubing 30 through the focal volume 301 without interference. The cylindrical coupling membrane 315 fits the diameter of the upper shell circular openings 314 and has the cylindrical coupling membrane internal diameter 316 that allows the easy passing through it of the endoscope 30 or of the reusable contaminated tubing 30 that is passing through the upper shell circular openings 314 and cylindrical coupling membrane 315. The cylindrical coupling membrane internal diameter 316 is designed in such way that the cylindrical coupling membrane 315 does not have any contact with the endoscope 30 or the reusable contaminated tubing 30, as seen in FIG. 31. Conversely, the cylindrical coupling membrane internal diameter 316 can be decreased to allow the cylindrical coupling membrane 315 to have close contact with the endoscope 30 or the reusable contaminated tubing 30. The reflector cavity 43 formed in between the lower shell 311 and upper shell 312 is filled completely with a fluid to allow the proper propagation and focusing of the focused acoustic pressure shockwaves 40. The lumen or lumens of the endoscope 30 or of the reusable contaminated tubing 30 are also filled with the decontamination fluid 205 to facilitate the proper action of the focused acoustic pressure shockwaves 40 that are used for accomplishing the complete dislodging and destruction of the contamination layer/biofilm 204 (shown in FIGS. 20B and 23 and not specifically in FIG. 31).

Figure 32B:
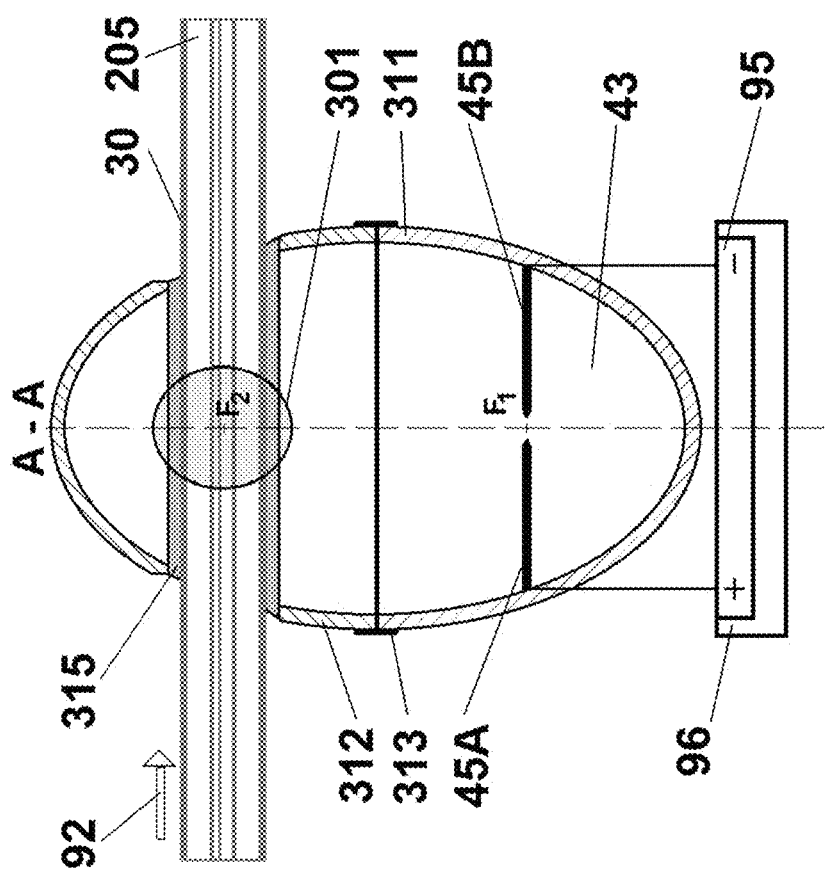
FIG. 32B is cross-section view along line A-A of FIG. 32A, according to one embodiment of the present invention.
Figure 32A:
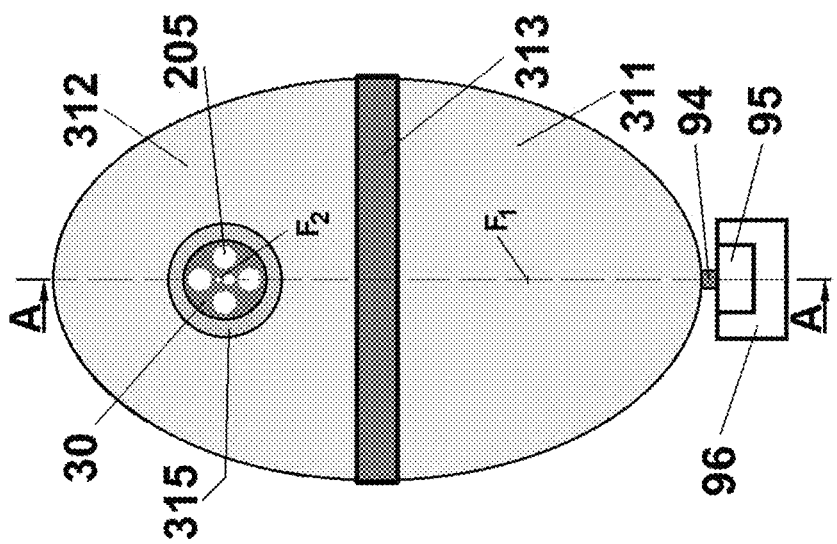
FIG. 32A is a schematic representation of a system using focused shockwaves applicators having full-ellipsoidal reflectors with a channel/opening to move the endoscope or reusable tubing from ventilators and dialysis machines and other medical devices through the focal volume during cleaning and high-level disinfection, according to one embodiment of the present invention.

FIGS. 32A and 32B present a view and a different cross-section of the embodiment from FIG. 31, to provide an even better understanding of this embodiment. The cross-section A-A depicts the focal volume 301 that is spherical in nature and it is centered in the second focal point $F_2$ of the special full-ellipsoidal applicator 310 (see FIG. 31). The size of the focal volume 301 is large enough to completely cover the full diametric dimension of the endoscope 30 or the reusable contaminated tubing 30, to assure a proper cleaning and decontamination. Also, to be able to cover the full length of the endoscope 30 or of the reusable contaminated tubing 30, requires the endoscope/tubing to constantly move in the tubing/endoscope moving direction 92 through the upper shell circular openings 314 and cylindrical coupling membrane 315. Finally, if the cylindrical coupling membrane 315 is in close contact with the external surface of the endoscope 30 or the reusable contaminated tubing 30, then there is no need to have any liquid bath 93, which will decrease the overall dimension of the cleaning and disinfection system. When there is no contact in between the cylindrical coupling membrane 315 and the external surface of the endoscope 30 or the reusable contaminated tubing 30, then there is a need to have the liquid bath 93 (not shown in FIG. 32) to allow the proper action of the focused acoustic pressure shockwaves 40 on both the external surface and internal lumen/lumens of the endoscope 30 or the reusable contaminated tubing 30.

Figure 33B:
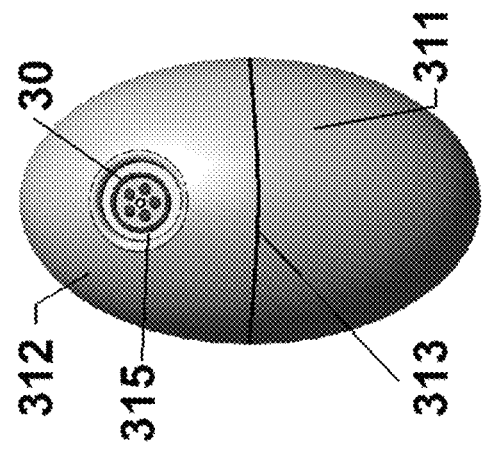
FIGS. 33A-33C are schematic 3D representations of the system illustrated in FIGS. 32A and 32B using focused shockwaves applicators having full-ellipsoidal reflectors with a channel/opening to move the endoscope or reusable tubing from ventilators and dialysis machines and other medical devices through the focal volume during cleaning and high-level disinfection, according to one embodiment of the present invention.
Figure 33A:
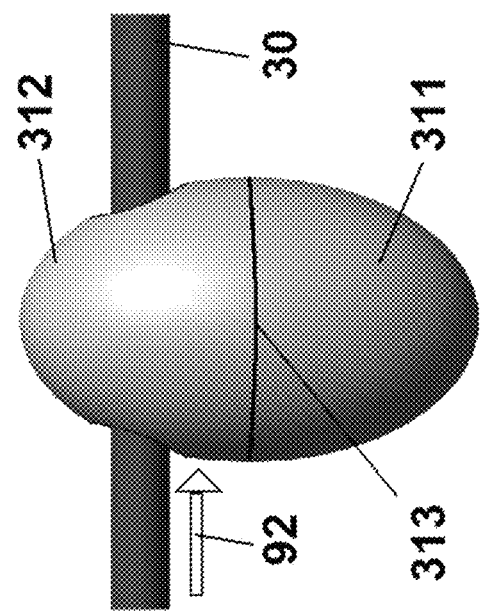
Figure 33C:
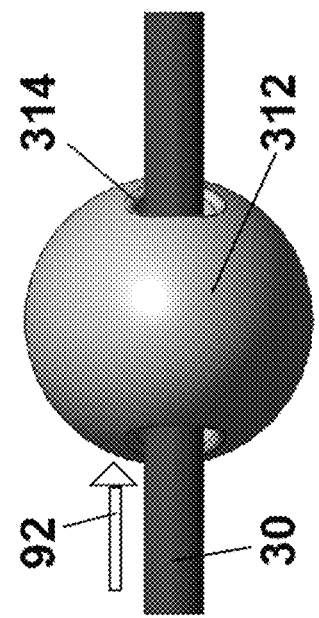

FIGS. 33A, 33B, and 33C show multiple three-dimensional views of the system that was presented in detail and its specific functioning described before in FIGS. 31, 32A, and 32B. In FIGS. 33A, 33B, and 33C all the elements and their numerical depiction are the same as those from FIGS. 31, 32A, and 32B.

Although the embodiment presented in FIGS. 31, 32A, 32B, 33A, 33B, and 33C shows specifically an electrohydraulic system that uses the spark-gap 41, the special full-ellipsoidal applicator 310 can also produce focused acoustic pressure shockwaves 40 using electrohydraulic generators with lasers. To assure the complete cleaning and decontamination on the full length of medical devices such as endoscopes 30, or of the reusable contaminated tubing 30 from respirators, hemodialysis units and any other medical devices, either the contaminated device/part needs to move or alternatively the special full-ellipsoidal applicator 310 moves and sometimes both, using manually or motorized automatic means.

The embodiment from FIGS. 34A, 34B, and 34C shows multiple views and a cross-section of a special full-ellipsoidal applicator 310 that has the upper shell U-shape lateral opening 340, which can be used for the cleaning and decontamination of endoscopes 30 or of the reusable contaminated tubing 30 from respirators, hemodialysis units and any other medical devices. The upper shell U-shape lateral opening 340 allows the accommodation a much larger range of dimensions for the endoscopes 30 or of the reusable contaminated tubing 30, when compared with the embodiment from FIGS. 31, 32A, 32B, 33A, 33B, and 33C. Also, the upper shell U-shape lateral opening 340 permits a much easier loading of the endoscope 30 or the reusable contaminated tubing 30, when compared with the embodiment from FIGS. 31, 32A, 32B, 33A, 33B, and 33C. However, the embodiment from FIGS. 34A, 34B, and 34C will require the operator to more closely monitor the movement of the endoscope 30 or the reusable contaminated tubing 30 in the tubing/endoscope moving direction 92, to be sure that it remains in the proper position in the lateral slot throughout the whole cleaning and decontamination process. The monitoring can be done visually by the operator or by using an automatic system and special guiding fixtures to have the endoscope 30 or the reusable contaminated tubing 30 constantly going through the focal volume 301 centered in $F_2$ (focal volume 301 is not shown in FIGS. 34A. 34B, and 34C for clarity).

The input high voltage discharge in $F_1$ (spark-gap 41 formed by the first electrode 45A and second electrode 45B) can be in between 14-30 kV. The high voltage for the first electrode 45A and the second electrode 45B is provided by the power supply 95 (included in control console/unit 96) via high voltage cable 94. The proposed construction of the special full-ellipsoidal applicator 310 is using a lower shell 311 with a distinctive upper shell 312, that are connected together via the shells connecting ring 313. This design provides a much higher efficiency in shockwave transmission, focusing, and a larger reflector cavity 43, which is filled with a fluid that plays a role in producing, focusing, and transmitting the focused acoustic pressure shockwaves 40 towards the endoscope 30 or the reusable contaminated tubing 30. The upper shell 312 of the special full-ellipsoidal applicator 310 has the upper shell U-shape lateral opening 340 that is sealed by the lateral U-shape coupling membrane 341 that allows the passing of the endoscope 30 or of the reusable contaminated tubing 30 through the focal volume 301 without interference. The lateral U-shape coupling membrane 341 fits the diameter of the endoscope 30 or of the reusable contaminated tubing 30 that is passing through the upper shell U-shape lateral opening 340 and lateral U-shape coupling membrane 341. There can be a direct contact or no contact of the lateral U-shape coupling membrane 341 with the endoscope 30 or the reusable contaminated tubing 30, as needed for each situation. The reflector cavity 43 formed in between the lower shell 311 and upper shell 312 is filled completely with a fluid to allow the proper propagation and focusing of the focused acoustic pressure shockwaves 40. The lumen or lumens of the endoscope 30 or of the reusable contaminated tubing 30 are also filled with the decontamination fluid 205 to facilitate the proper action of the focused acoustic pressure shockwaves 40 for accomplishing the complete dislodging and destruction of the contamination layer/biofilm 204 (shown in FIGS. 20B and 23 and not specifically in FIGS. 34A-34C).

The focal volume 301 produced by the special full-ellipsoidal applicator 310 is spherical in nature and it is centered in the second focal point $F_2$ of the special full-ellipsoidal applicator 310 (as seen in FIGS. 30 and 32B and not shown in FIGS. 34A-34C for simplicity). The size of the focal volume 301 is large enough to completely cover the full diametric dimension of the endoscope 30 or the reusable contaminated tubing 30, to assure a proper cleaning and decontamination. Also, to be able to cover the full length of the endoscope 30 or of the reusable contaminated tubing 30, requires the endoscope/tubing to constantly move in the tubing/endoscope moving direction 92 through the upper shell U-shape lateral opening 340 and lateral U-shape coupling membrane 341. Finally, there is a need to have the liquid bath 93 (not shown in FIGS. 34A-34C) to allow the proper action of the focused acoustic pressure shockwaves 40 on both the external surface and internal lumen/lumens of the endoscope 30 or the reusable contaminated tubing 30.

Although the embodiment presented in FIGS. 34A-34C shows specifically an electrohydraulic system that uses the spark-gap 41, the special full-ellipsoidal applicator 310 can also produce focused acoustic pressure shockwaves 40 using electrohydraulic generators with lasers. To assure the complete cleaning and decontamination on the full length of medical devices such as endoscopes 30, or of the reusable contaminated tubing 30 from respirators, hemodialysis units and any other medical devices, either the contaminated device/part needs to move or alternatively the special full-ellipsoidal applicator 310 moves and sometimes both, using manually or motorized automatic means.

Figure 35A:
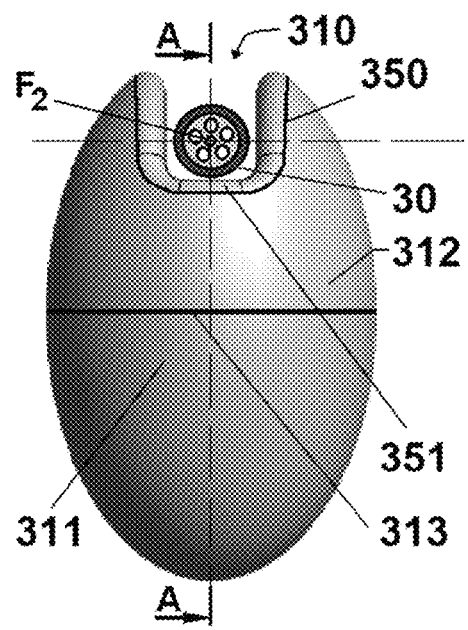
FIGS. 35A-35C are schematic representations of a system using focused shockwaves applicators having full-ellipsoidal reflectors with a top slot to move the endoscope or reusable tubing from ventilators and dialysis machines or from any other medical devices through the focal volume during cleaning and high-level disinfection, according to one embodiment of the present invention.
Figure 35B:
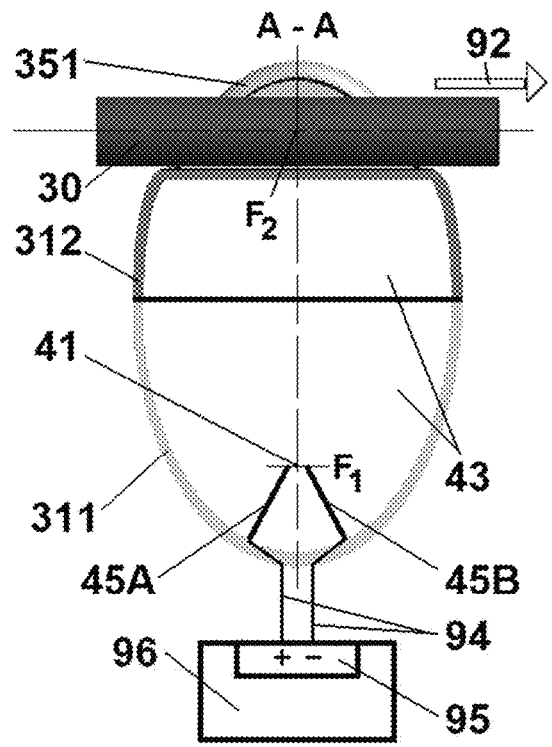
Figure 35C:
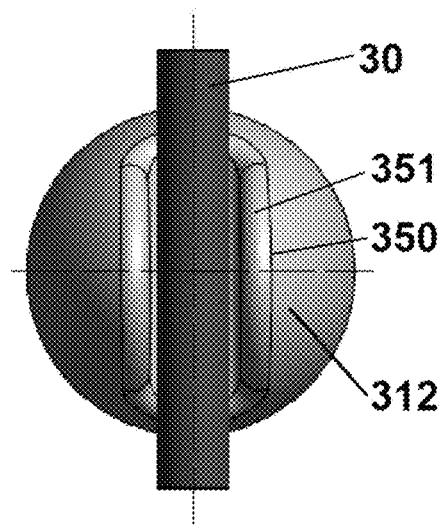

The embodiment from FIGS. 35A, 35B, and 35C shows multiple views and a cross-section of a special full-ellipsoidal applicator 310 that has the upper shell U-shape upward opening 350, which can be used for the cleaning and decontamination of endoscopes 30 or of the reusable contaminated tubing 30 from respirators, hemodialysis units and any other medical devices. The upper shell U-shape upward opening 350 allows the accommodation a much larger range of dimensions for the endoscopes 30 or of the reusable contaminated tubing 30, when compared with the embodiment from FIGS. 31, 32A-32B, and 33A-33C. Also, the upper shell U-shape upward opening 350 permits a much easier loading of the endoscope 30 or the reusable contaminated tubing 30, when compared with the embodiment from FIGS. 31, 32A-32B, and 33A-33C. However, the embodiment from FIGS. 35A, 35B, and 35C will require the operator to more closely monitor the movement of the endoscope 30 or the reusable contaminated tubing 30 in the tubing/endoscope moving direction 92, to be sure that it remains in the proper position in the top slot throughout the whole cleaning and decontamination process. The monitoring can be done visually by the operator or by using an automatic system and special guiding fixtures to have the endoscope 30 or the reusable contaminated tubing 30 constantly going through the focal volume 301 centered in $F_2$ (focal volume 301 is not shown in FIGS. 35A-35C for clarity).

The input high voltage discharge in F (spark-gap 41 formed by the first electrode 45A and second electrode 45B) can be in between 14-30 kV. The high voltage for the first electrode 45A and the second electrode 45B is provided by the power supply 95 (included in control console/unit 96) via high voltage cable 94. The proposed construction of the special full-ellipsoidal applicator 310 is using a lower shell 311 with a distinctive upper shell 312, that are connected together via the shells connecting ring 313. This design provides a much higher efficiency in shockwave transmission, focusing, and a larger reflector cavity 43, which is filled with a fluid that plays a role in producing, focusing, and transmitting the focused acoustic pressure shockwaves 40 towards the endoscope 30 or the reusable contaminated tubing 30. The upper shell 312 of the special full-ellipsoidal applicator 310 has the upper shell U-shape upward opening 350 that is sealed by the upward U-shape coupling membrane 351 that allows the passing of the endoscope 30 or of the reusable contaminated tubing 30 through the focal volume 301 without interference. The upward U-shape coupling membrane 351 fits the diameter of the endoscope 30 or of the reusable contaminated tubing 30 that is passing through the upper shell U-shape upward opening 350 and upward U-shape coupling membrane 351. There can be a direct contact or no contact of the upward U-shape coupling membrane 351 with the endoscope 30 or the reusable contaminated tubing 30, as needed for each situation. The reflector cavity 43 formed in between the lower shell 311 and upper shell 312 is filled completely with a fluid to allow the proper propagation and focusing of the focused acoustic pressure shockwaves 40. The lumen or lumens of the endoscope 30 or of the reusable contaminated tubing 30 are also filled with the decontamination fluid 205 to facilitate the proper action of the focused acoustic pressure shockwaves 40 for accomplishing the complete dislodging and destruction of the contamination layer/biofilm 204 (shown in FIGS. 20B and 23 and not specifically in FIGS. 35A-35C).

The focal volume 301 produced by the special full-ellipsoidal applicator 310 is spherical in nature and it is centered in the second focal point $F_2$ of the special full-ellipsoidal applicator 310 (as seen in FIGS. 30 and 32B and not shown in FIGS. 35A-35C for simplicity). The size of the focal volume 301 is large enough to completely cover the full diametric dimension of the endoscope 30 or the reusable contaminated tubing 30, to assure a proper cleaning and decontamination. Also, to be able to cover the full length of the endoscope 30 or of the reusable contaminated tubing 30, requires the endoscope/tubing to constantly move in the tubing/endoscope moving direction 92 through the upper shell U-shape upward opening 350 and upward U-shape coupling membrane 351. Finally, there is a need to have the liquid bath 93 (not shown in FIG. 35) to allow the proper action of the focused acoustic pressure shockwaves 40 on both the external surface and internal lumen/lumens of the endoscope 30 or the reusable contaminated tubing 30.

Although the embodiment presented in FIGS. 35A-35C shows specifically an electrohydraulic system that uses the spark-gap 41, the special full-ellipsoidal applicator 310 can also produce focused acoustic pressure shockwaves 40 using electrohydraulic generators with lasers. To assure the complete cleaning and decontamination on the full length of medical devices such as endoscopes 30, or of the reusable contaminated tubing 30 from respirators, hemodialysis units and any other medical devices, either the contaminated device/part needs to move or alternatively the special full-ellipsoidal applicator 310 moves and sometimes both, using manually or motorized automatic means.

In the embodiments from FIGS. 31-35C only one special full-ellipsoidal applicator 310 was used for the cleaning and decontamination of the endoscopes 30, or of the reusable contaminated tubing 30 from respirators, hemodialysis units, and any other medical devices. To increase efficiency and reduce duration of the cleaning and decontamination, multiple special full-ellipsoidal applicators 310 can be used, by arranging them in a sequential manner, as it is presented in the embodiment from FIG. 36. The full-ellipsoidal applicators 310 with the upper shell U-shape lateral opening 340 and lateral U-shape coupling membrane 341 are exemplified in FIG. 36. However, full-ellipsoidal applicators 310 with the upper shell U-shape upward opening 350 and upward U-shape coupling membrane 351 can also be used. The cleaning and decontamination system from FIG. 36 has a total of four applicators that include the first laterally-slotted full ellipsoidal applicator 360, the second laterally-slotted full ellipsoidal applicator 361, the third laterally-slotted full ellipsoidal applicator 362, and the fourth laterally-slotted full ellipsoidal applicator 363. The four applicators 360, 361, 362, and 363 are all constructed by using a lower shell 311 and a distinctive upper shell 312, that are connected together via the shells connecting ring 313. To provide a more efficient spatial distribution, all four applicators 360, 361, 362, and 363 are rotated with 90 degrees back and forth along the endoscope 30 or the reusable contaminated tubing 30. There might be other embodiments that can have more than four applicators, depending on the type of endoscope 30 or the reusable contaminated tubing 30 and the efficiency or duration of the cleaning and high-level disinfection process.

Figure 36:
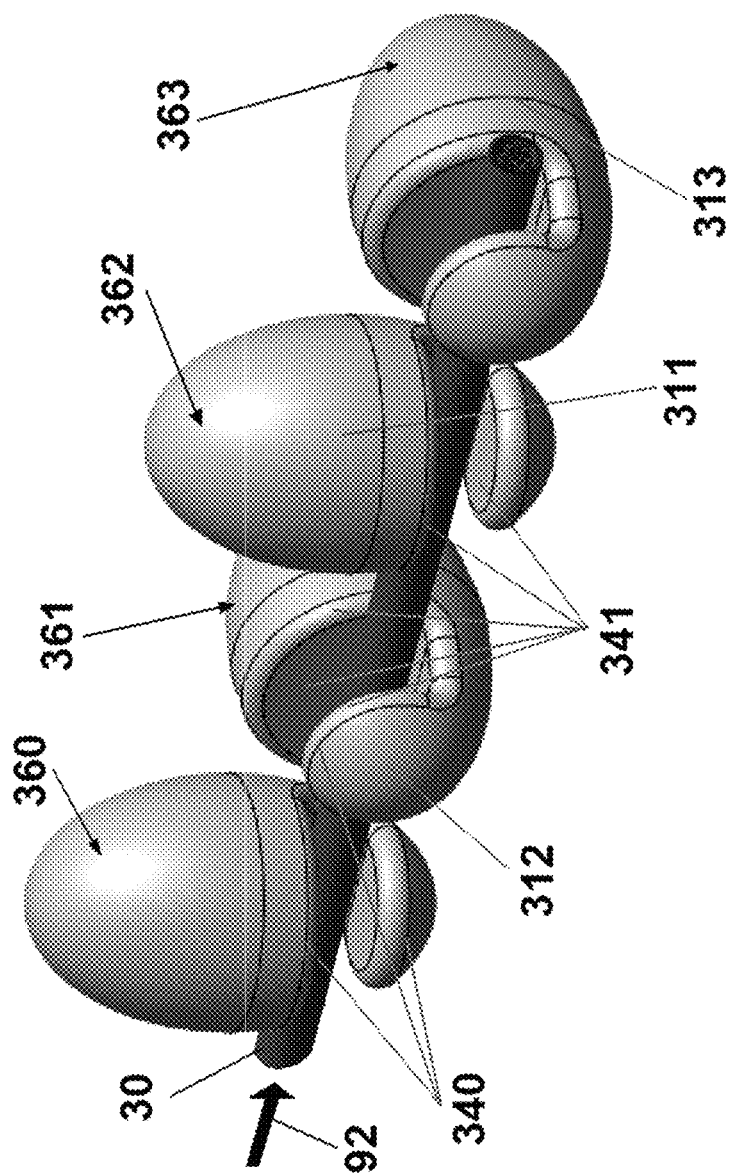
FIG. 36 is a schematic representation of a system with an array of applicators having full-ellipsoidal reflectors with a lateral slot to move the endoscope or reusable tubing from ventilators and dialysis machines or from any other medical devices through the focal volume during cleaning and high-level disinfection, according to one embodiment of the present invention.

For the embodiment from FIG. 36, a liquid bath 93 is needed to allow the proper action of the waves 40 (including in respective embodiments focused acoustic pressure shockwaves, pseudo-planar pressure waves or acoustic radial pressure waves) on both the external surface and internal lumen/lumens of the endoscope 30 or the reusable contaminated tubing 30. The liquid bath 93 and the focused acoustic pressure shockwaves 40 are not shown in FIG. 36 for simplicity. Also, for a good cleaning and high-level disinfection on the full length of the endoscopes 30, or of the reusable contaminated tubing 30 from respirators, hemodialysis units, and any other medical devices, the endoscopes/tubes need to move in the tubing/endoscope moving direction 92. The operator needs to closely monitor the movement of the endoscope 30 or the reusable contaminated tubing 30 to be sure that it remains in the proper position in the dedicated slot of the applicators 360, 361, 362, and 363 throughout the whole cleaning and decontamination process. The monitoring can be done visually by the operator or by using an automatic system and special guiding fixtures to have the endoscope 30 or the reusable contaminated tubing 30 constantly going through the focal volumes 301 centered in $F_2$ (not shown in FIG. 36 for clarity).

The embodiment presented in FIG. 36 shows specifically, the special full-ellipsoidal applicator 310 can produce focused acoustic pressure shockwaves 40 using an electrohydraulic system that uses the spark-gap 41 or electrohydraulic generators with lasers. To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicators 360, 361, 362, and 363 can move in synchronicity and sometimes both (applicators and endoscope/tubing), using manually or motorized automatic means.

The embodiment from FIG. 37 is a decontamination piezoelectric system 370 that is capable to easily generate acoustic planar pressure waves 374 by using piezoelectric elements 375, such as flat piezo crystals/piezo ceramics or a piezo fiber layer. These decontamination piezoelectric systems 370 can be used to generate acoustic planar pressure waves 374 and direct them towards endoscopes 30 or the reusable contaminated tubing 30. In order to get the applicator 97 in contact with the surface of an endoscope 30 or reusable contaminated tubing 30, the applicator 97 is moved via transversal (T) and longitudinal (L) motions. By applying an electrical field to piezoelectric elements 375 (such as flat piezo crystals/piezo ceramics or a piezo fiber layer) uniformly placed on the central core 371 (can be cylindrical, square, hexagonal, octagonal or decagonal, etc.), a mechanical strain is resulting that produces acoustic planar pressure waves 374 inside the fluid-filled lateral semi-cylindrical coupling membrane 373. The electrical field for the piezoelectric element 375—crystals/piezo ceramics or for the piezo fiber layer—is provided via high voltage cable 94 by the power supply 95, which is included in control console/unit 96. On its upper part the applicator 97 has an upper cover 372 that is the support for the lateral semi-cylindrical coupling membrane 373 and also it helps with the correct orientation of the applicator 97 to properly direct the acoustic planar pressure waves 374 to pass through the endoscope 30 or reusable contaminated tubing 30. For the construction that uses the piezo crystals/piezo ceramics, individual or multiple piezo crystals/piezo ceramics can be activated concomitantly or sequentially, which can tailor the delivery of the acoustic planar pressure waves 374 based on explicit needs of the cleaning and decontamination process.

For the embodiment from FIG. 37, a liquid bath 93 and associated liquid bath enclosure 171 are needed to allow the proper action of the acoustic planar pressure waves 374 on both the external surface and internal lumen/lumens of the endoscope 30 or the reusable contaminated tubing 30. Also, for a good cleaning and high-level disinfection on the full length of the endoscopes 30, or of the reusable contaminated tubing 30 from respirators, hemodialysis units, and any other medical devices, they need to move in the tubing/endoscope moving direction 92. To not increase considerable the dimensions of the liquid bath 93 and associated liquid bath enclosure 171, the endoscope 30 and the reusable contaminated tubing 30 can enter and exit the liquid bath 93 immediately before and after passing in front of the acoustic planar pressure waves 374. To assure the complete cleaning and decontamination on the full length of medical devices such as endoscopes 30, or of the reusable contaminated tubing 30 from respirators, hemodialysis units and any other medical devices, either the contaminated device/part needs to move or alternatively the applicator 97 moves and sometimes both, using manually or motorized automatic means.

FIG. 38A shows the features characteristic of the ultrasound pressure waves, which were discussed in detail previously when all type of shockwaves or pressure waves were compared at the beginning at this invention. FIG. 38B presents an embodiment that uses low frequency ultrasound waves (main ultrasound waves 380 and secondary ultrasound waves 381) for cleaning and high-level disinfection of endoscopes 30 or reusable contaminated tubing 30 from ventilators and dialysis machines or from any other medical devices.

Inside the ultrasound applicator 382 and also inside the applicator/coupling membrane 44, there is a central metal acoustic horn 384 that amplifies the vibration of the piezo crystal/piezo ceramic (placed inside the ultrasound applicator 382 body and not specifically shown in FIG. 38B) towards the ultrasound-generating main plate 383, which is used to produce the main ultrasound waves 380. The ultrasound-generating piezo crystal/piezo ceramic (placed inside the ultrasound applicator 382 body and not specifically shown in FIG. 38B) converts and transfers the input electrical power received via power cable 94 from the power supply 95 (included in the control console/unit 96) into vibrational mechanical (ultrasonic) energy that will be delivered via the ultrasound transmission fluid 385 and the applicator/coupling membrane 44 for the cleaning and high-level disinfection of endoscopes 30 or reusable contaminated tubing 30 from ventilators and dialysis machines or from any other medical devices. The acoustic horn 384 is used to amplify the excitation of the ultrasound-generating piezo crystal/piezo ceramic into the proper ultrasound amplitude 388A (see FIG. 38A) and thus produce more robust and energetic main ultrasound waves 380 that exit the applicator/coupling membrane 44 along the central longitudinal axis of the ultrasound applicator 382. The ultrasound waves 380 are mainly used for the cleaning and decontamination of the interior channels 170 of the endoscopes 30 or lumen or lumens of reusable contaminated tubing 30.

The same ultrasound applicator 382 has two circumferential, external, and opposite (positioned 180-degrees apart) ultrasound-generating secondary piezo crystal/piezo ceramic 386 that are producing the secondary ultrasound waves 381, which are used to clean the interior channels 170 of the endoscopes 30 or lumen or lumens of reusable contaminated tubing 30 and also the exterior surface of the endoscope/tubing. The ultrasound-generating secondary piezo crystal/piezo ceramic 386 are mounted on the ultrasound applicator 382 in such way that they are capable of having a swiveling motion S around a pivoting point, which helps to adapt to the possible texture or variations in the external surface of the endoscope 30 or reusable contaminated tubing 30, as seen for example in FIG. 38B that shows a corrugated tubing.

The ultrasound-generating main plate 383 and also the ultrasound-generating secondary piezo crystal/piezo ceramic 386 have radial surfaces to be able to radiate the main ultrasound waves 380 and secondary ultrasound waves 381 in a radial/spherical manner. In order to get the ultrasound applicator 382 in contact with the surface of an endoscope 30 or reusable contaminated tubing 30, the ultrasound applicator 382 is moved via transversal (T) and longitudinal (L) motions. To assure the complete cleaning and decontamination on the full length of medical devices such as endoscopes 30, or of the reusable contaminated tubing 30 from respirators, hemodialysis units and any other medical devices, either the contaminated device/part needs to move or alternatively the ultrasound applicator 382 moves and sometimes both, using manually or motorized automatic means. In FIG. 38B the endoscope 30, or reusable contaminated tubing 30 from respirators or hemodialysis units or from any other medical devices) is moving in the tubing/endoscope moving direction 92 and in front of the main ultrasound waves 380 and secondary ultrasound waves 381.

For FIG. 38B, since the main ultrasound waves 380 and secondary ultrasound waves 381 need to be produced in a liquid medium, in order to not lose energy through reflections at the change of acoustic impedance from one medium to another and fully take advantage of the micro-jets produced by the collapse of cavitation bubbles, the endoscope 30 or the reusable contaminated tubing 30 are placed into liquid bath 93 and their lumen/lumens filled with a decontamination fluid 205 (see FIGS. 20B and 21B). For a good cleaning and high-level disinfection on the full length of the endoscopes 30, or of the reusable contaminated tubing 30 from respirators, hemodialysis units, and any other medical devices, they need to move in the tubing/endoscope moving direction 92. To not increase considerable the dimensions of the liquid bath 93, the endoscope 30 and the reusable contaminated tubing 30 can enter and exit the liquid bath 93 immediately before and after passing in front of the main ultrasound waves 380 and secondary ultrasound waves 381. To assure the complete cleaning and decontamination on the full length of medical devices such as endoscopes 30, or of the reusable contaminated tubing 30 from respirators, hemodialysis units and any other medical devices, either the contaminated device/part needs to move or alternatively the ultrasound applicator 382 moves and sometimes both, using manually or motorized automatic means.

Figure 39:
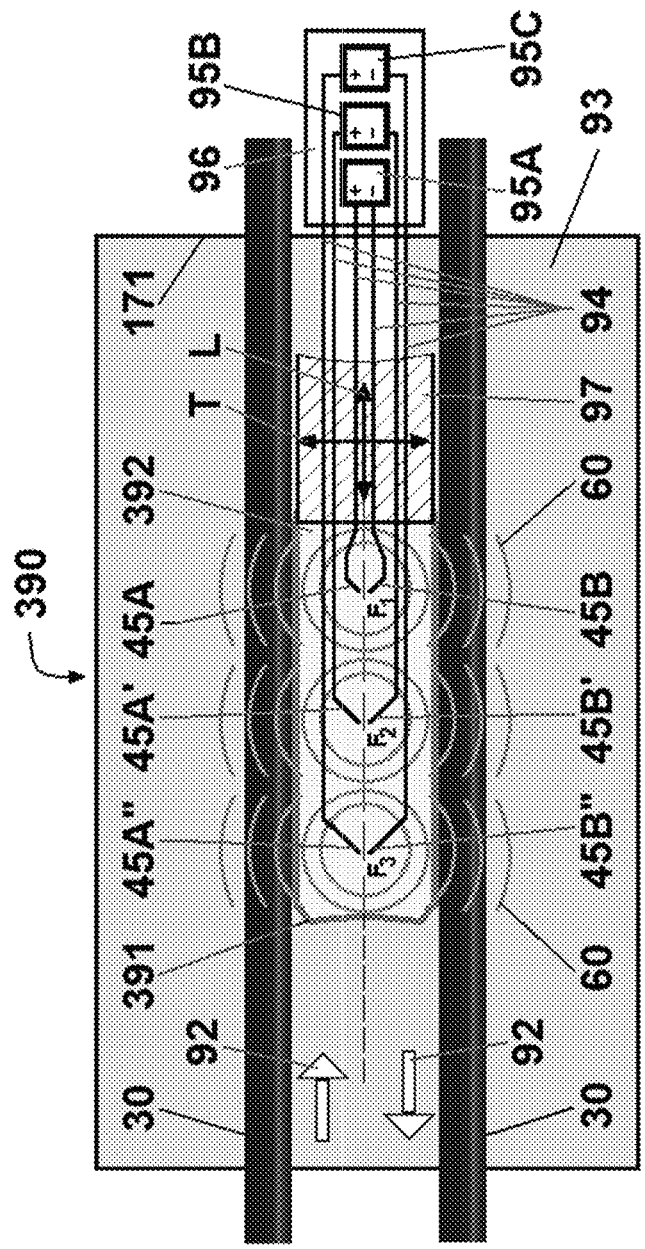
FIG. 39 is a schematic representation of a multiple electrohydraulic radial pressure waves system used for cleaning and high-level disinfection simultaneously of two endoscopes or two reusable tubes from ventilators and dialysis machines and other medical devices, according to one embodiment of the present invention.

In the embodiment from FIG. 39 the decontamination system with multiple radial pressure waves 390 is using the acoustic radial pressure wave 40 that are generated via multiple high voltage discharges, which is the electrohydraulic principle using high voltage discharges across the spark-gaps 41 seen in FIG. 4 that are overlapping with $F_1$, $F_2$, and $F_3$ points, which are spread equally along the longitudinal axis of the applicator 97. As shown in this figure, there are three high voltage discharges produced in a fluid-filled volume 392 created in between the cylindrical coupling membrane 391 and the body of the applicator 97. The first spark-gap discharge in $F_1$ is produced in between first electrode 45A and the second electrode 45B, the second spark-gap discharge in $F_2$ is produced in between third electrode 45A' and the fourth electrode 45B', and the third spark-gap in $F_3$ is produced in between fifth electrode 45A" and the sixth electrode 45B". The high voltage for each pair of electrodes is provided from independent power supplies to allow a proper discharge without interference from the other pairs of electrodes. Thus, the discharge in $F_1$ produced in between first electrode 45A and the second electrode 45B is powered by the first power supply 95A, the discharge in $F_2$ produced in between third electrode 45A' and the fourth electrode 45B' is powered by the second power supply 95B, and the discharge in $F_3$ produced in between fifth electrode 45A" and the sixth electrode 45B" is powered by the third power supply 95C. The power supplies 95A, 95B, and 95C are all included in the control console/unit 96 and are connected with the applicator 97 via high voltage cable 94. In an alternative embodiment, a single power supply 95 (as seen in FIGS. 9-17B, 19A-22, 24-25B, 27, 31-32B, 34B, 35B, 37, and 38B) that can be used to power all three pairs of electrodes. For this embodiment, the first pair of electrodes 45A and 45B, the second pair of electrodes 45A' and 45B', and the third pair of electrodes 45A" and 45B" can be activated concomitantly or sequentially, based on specific needs of the cleaning and decontamination. Furthermore, only two pairs of electrodes can be used or even only one of the pairs of electrodes can be activated, which can tailor the delivery of the acoustic radial pressure waves 40 on specific locations of the endoscope 30 and the reusable contaminated tubing 30.

Due to its construction the decontamination system with multiple radial pressure waves 390 is cleaning and decontaminating simultaneously two endoscopes 30 or two reusable contaminated tubing/tubes 30 that are moving in opposite tubing/endoscope moving directions 92 through the of the acoustic radial pressure waves 40. There is no reflector present in this embodiment presented in FIG. 39 and this is why when the spark-gap discharges are produced, the associated plasma bubbles expand and collapse transforming the heat into kinetic energy in the form of spherical waves known as acoustic radial pressure waves 40. Due to the spherical nature of the acoustic pressure waves produced by the applicator 97 of this embodiment, the acoustic radial pressure waves 40 will propagate in all directions. The applicator 97 has only a portion of the cylindrical coupling membrane 391 in contact with the endoscopes 30 and the reusable contaminated tubing/tubes 30, and this is why only a portion of the spherical pressure waves/acoustic radial pressure waves 40 are transmitted through the endoscopes 30 and the reusable contaminated tubing/tubes 30. The rest of the spherical pressure waves/acoustic radial pressure waves 40 are transmitted away and in between the endoscopes 30 and the reusable contaminated tubing/tubes 30. However, the symmetrical and rotational nature of the applicator 97, offer ease-of-use for the personnel, who does not have to choose a preferred/specific position for the applicator 97 during cleaning and decontaminating process. In order to get the applicator 97 in contact with the surface of an endoscope 30 or reusable contaminated tubing 30, the applicator 97 is moved via transversal (T) and longitudinal (L) motions.

For FIG. 39, since the acoustic radial pressure waves 40 need to be produced in a liquid medium, in order to not lose energy through reflections at the change of acoustic impedance from one medium to another and fully take advantage of the micro-jets produced by the collapse of cavitation bubbles, the two endoscopes 30 or the reusable contaminated tubing/tubes 30 are placed into liquid bath 93 from inside the liquid bath enclosure 171 and their lumen/lumens filled with a decontamination fluid 205 (see FIGS. 20B and 21B). For a good cleaning and high-level disinfection on the full length of the endoscopes 30, or of the reusable contaminated tubing/tubes 30 from respirators, hemodialysis units, and any other medical devices, they need to move in the tubing/endoscope moving directions 92. To not increase considerable the dimensions of the liquid bath 93 and the liquid bath enclosure 171, the endoscope 30 and the reusable contaminated tubing/tubes 30 can enter and exit the liquid bath 93 immediately before and after passing in front of the acoustic radial pressure waves 40. To assure the complete cleaning and decontamination on the full length of medical devices such as endoscopes 30, or of the reusable contaminated tubing/tubes 30 from respirators, hemodialysis units and any other medical devices, either the contaminated devices/parts need to move or alternatively the applicator 97 moves and sometimes both, using manually or motorized automatic means.

Figure 40:
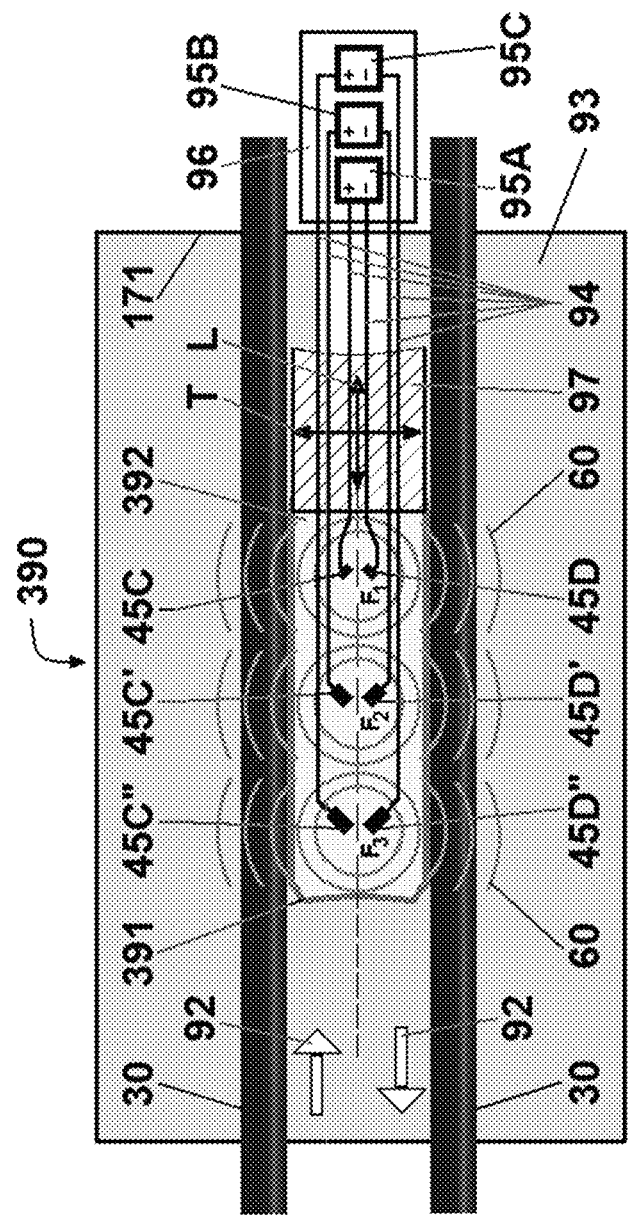
FIG. 40 is a schematic representation of a multiple laser-produced electrohydraulic radial pressure waves system used for cleaning and high-level disinfection simultaneously of two endoscopes or two reusable tubes from ventilators and dialysis machines and other medical devices, according to one embodiment of the present invention.

In the embodiment from FIG. 40 the decontamination system with multiple radial pressure waves 390 is using the acoustic radial pressure waves 40 that are generated via multiple laser sources (electrohydraulic principle using multiple lasers sources) that are equally spread along the longitudinal axis of the applicator 97. There are three pairs of incased lasers that are producing laser beams and plasma bubbles in a fluid-filled volume 392 created in between the cylindrical coupling membrane 391 and the body of the applicator 97. The first incased laser 45C and the second incased laser 45D represent the first pair of encased lasers that produces laser beams in $F_1$, the third incased laser 45C' and the fourth incased laser 45D' represent the second pair of encased lasers that produces laser beams in $F_2$, and the fifth incased laser 45C'' and sixth incased laser 45D'' represent the third pair of encased lasers that produces laser beams in $F_3$. In one embodiment, the high voltage for each pair of encased lasers is provided from independent power supplies. Thus, the first incased laser 45C and the second incased laser 45D are powered by the first power supply 95A, the third incased laser 45C' and the fourth incased laser 45D' are powered by the second power supply 95B, and the fifth incased laser 45C'' and sixth incased laser 45D'' are powered by the third power supply 95C. In another embodiment all the lasers are powered by only one power source/supply 95, as seen in FIGS. 9-17B, 19A-22, 24-25B, 27, 31-32B, 34B, 35B, 37, and 38B, that uses laser splitters (not shown) to split energy in between different encased lasers. Regardless of design, the power source/supply 95 or sources (95A, 95B, and 95C) are included in the control console/unit 96 and are connected with the applicator 97 via high voltage cable 94. For this embodiment, the first pair of encased lasers 45C and 45D, the second pair of encased lasers 45C' and 45D', and the third pair of encased lasers 45C'' and 45D'' can be activated concomitantly or sequentially. Furthermore, only two pairs of encased lasers can be used or even only one of the pairs of encased lasers can be activated, which can tailor the treatment on delivering the acoustic radial pressure waves 40 on specific locations of the endoscopes 30 and the reusable contaminated tubing/tubes 30.

To control the good functionality of the lasers there are means of monitoring the system performance by measuring the reaction temperature of the plasma bubble collapse using a method of optical fiber thermometry, which are not specifically shown in FIG. 40, but were shown in detail in FIG. 12. Also, in this embodiment there is no reflector present and this is why when the lasers discharges are produced, the associated plasma bubbles expand and collapse transforming the heat into kinetic energy in the form of spherical waves known as acoustic radial pressure waves 40. Due to the spherical nature of the acoustic pressure waves produced by the applicator 97 of this embodiment, the acoustic radial pressure waves 40 will propagate in all directions. The applicator 97 has only a portion of the cylindrical coupling membrane 391 in contact with the endoscopes 30 and the reusable contaminated tubing/tubes 30, and this is why only a portion of the spherical pressure waves/acoustic radial pressure waves 40 are transmitted through the endoscopes 30 and the reusable contaminated tubing/tubes 30. The rest of the spherical pressure waves/acoustic radial pressure waves 40 are transmitted away and it between the endoscopes 30 and the reusable contaminated tubing/tubes 30. However, the symmetrical and rotational nature of the applicator 97, offer ease-of-use for the personnel, who does not have to choose a preferred/specific position for the applicator 97 during cleaning and decontaminating process. In order to get the applicator 97 in contact with the surface of an endoscope 30 or reusable contaminated tubing 30, the applicator 97 is moved via transversal (T) and longitudinal (L) motions.

For FIG. 40, since the acoustic radial pressure waves 40 need to be produced in a liquid medium, in order to not lose energy through reflections at the change of acoustic impedance from one medium to another and fully take advantage of the micro-jets produced by the collapse of cavitation bubbles, the two endoscopes 30 or the reusable contaminated tubing/tubes 30 are placed into liquid bath 93 from inside the liquid bath enclosure 171 and their lumen/lumens filled with a decontamination fluid 205 (see FIGS. 20B and 21B). For a good cleaning and high-level disinfection on the full length of the endoscopes 30, or of the reusable contaminated tubing/tubes 30 from respirators, hemodialysis units, and any other medical devices, they need to move in the tubing/endoscope moving directions 92. To not increase considerable the dimensions of the liquid bath 93 and the liquid bath enclosure 171, the endoscope 30 and the reusable contaminated tubing/tubes 30 can enter and exit the liquid bath 93 immediately before and after passing in front of the acoustic radial pressure waves 40. To assure the complete cleaning and decontamination on the full length of medical devices such as endoscopes 30, or of the reusable contaminated tubing/tubes 30 from respirators, hemodialysis units and any other medical devices, either the contaminated devices/parts need to move or alternatively the applicator 97 moves and sometimes both, using manually or motorized automatic means.

Figure 41:
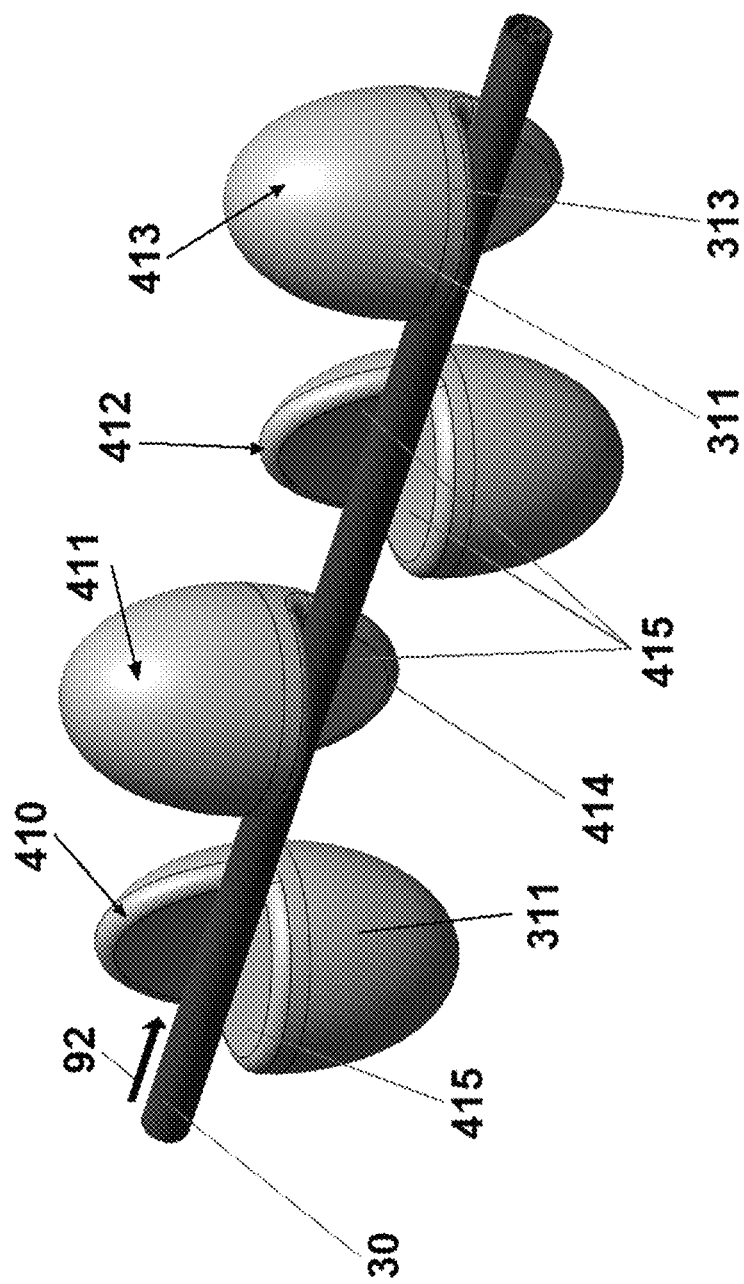
FIG. 41 is a schematic representation of a system with an array of platform applicators producing radial or pseudo-planar pressure waves for cleaning and high-level disinfection of endoscopes or tubing from ventilators and dialysis machines and other medical devices, according to one embodiment of the present invention.

To increase efficiency and reduce duration of the cleaning and decontamination, an array of multiple platform applicators 410-413 can be used, by arranging them in a sequential manner, as it is presented in the embodiment from FIG. 41. The cleaning and decontamination array from FIG. 41 has a total of four applicators that include the first platform applicator 410, the second platform applicator 411, the third platform applicator 412, and the fourth platform applicator 413. The four platform applicators 410, 411, 412, and 413 are all constructed by using a lower shell 311 and a distinctive L-shape upper shell 414, which are connected together via the shells connecting ring 313. On the top of the aperture of the L-shape upper shells 414 sits a corresponding L-shape coupling membranes 415. In this way, an enclosed space filled with fluid is created in which the pressure waves, such as pseudo-planar pressure waves 40 or acoustic radial pressure waves 40 or unfocused pressure waves, are created. To provide a more efficient spatial distribution, all four platform applicators 410, 411, 412, and 413 are rotated with 180 degrees and positioned on the same side and along the endoscope 30 or the reusable contaminated tubing 30. There might be other embodiments that can have more than four applicators, depending on the type of endoscope 30 or the reusable contaminated tubing 30 and the efficiency or duration of the cleaning and high-level disinfection process.

For the embodiment from FIG. 41, a liquid bath 93 is needed to allow the proper action of the pseudo-planar pressure waves 40 or of the acoustic radial pressure waves 40 or of the unfocused pressure waves on both the external surface and internal lumen/lumens of the endoscope 30 or the reusable contaminated tubing 30. The liquid bath 93 and the pseudo-planar pressure waves 40 or the acoustic radial pressure waves 40 or unfocused pressure waves are not shown in FIG. 41 for simplicity. Also, for a good cleaning and high-level disinfection on the full length of the endoscopes 30, or of the reusable contaminated tubing 30 from respirators, hemodialysis units, and any other medical devices, the endoscopes/tubes need to move in the tubing/endoscope moving direction 92. The operator needs to closely monitor the movement of the endoscope 30 or the reusable contaminated tubing 30 to be sure that it remains in the proper position on the platform of the platform applicators 410, 411, 412, and 413 and in close contact with the L-shape coupling membranes 415 throughout the whole cleaning and decontamination process. The monitoring can be done visually by the operator or by using an automatic system and special guiding fixtures to have the endoscope 30 or the reusable contaminated tubing 30 constantly in the proper position relatively to the platform applicators 410, 411, 412, and 413.

For the embodiment presented in FIG. 41 the platform applicators 410, 411, 412, and 413 can use all types of generation principles for creating pseudo-planar pressure waves 40 or the acoustic radial pressure waves 40 or unfocused pressure waves using electrohydraulic generators (with spark-gaps or lasers), piezoelectric generators (with piezo crystals/piezo ceramics or piezo fibers) or electromagnetic generators (with flat coils or cylindrical coils). To assure the complete cleaning and decontamination on the full length of medical devices such as endoscopes 30, or of the reusable contaminated tubing 30 from respirators, hemodialysis units and any other medical devices, either the contaminated device/part needs to move or alternatively the platform applicators 410, 411, 412, and 413 can move in synchronicity and sometimes both (applicators and endoscope/tubing), using manually or motorized automatic means. In FIG. 41 the endoscope 30, or reusable contaminated tubing 30 from respirators or hemodialysis units or from any other medical devices is moving in the tubing/endoscope moving direction 92 and in front of the pseudo-planar pressure waves 40 or the acoustic radial pressure waves 40 or unfocused pressure waves.

Figure 42A:
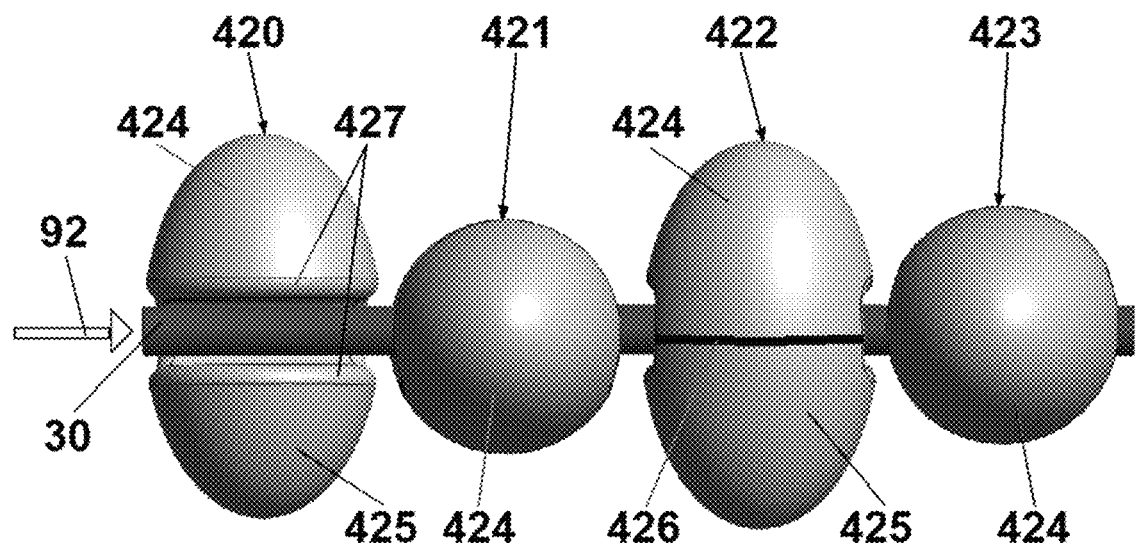
FIGS. 42A and 42B are schematic representations of a system with an array of four double-applicators rotated with 90 degrees for each subsequent applicator that are producing radial or pseudo-planar pressure waves for cleaning and high-level disinfection of endoscopes or tubing from ventilators and dialysis machines and other medical devices, according to one embodiment of the present invention.
Figure 42B:
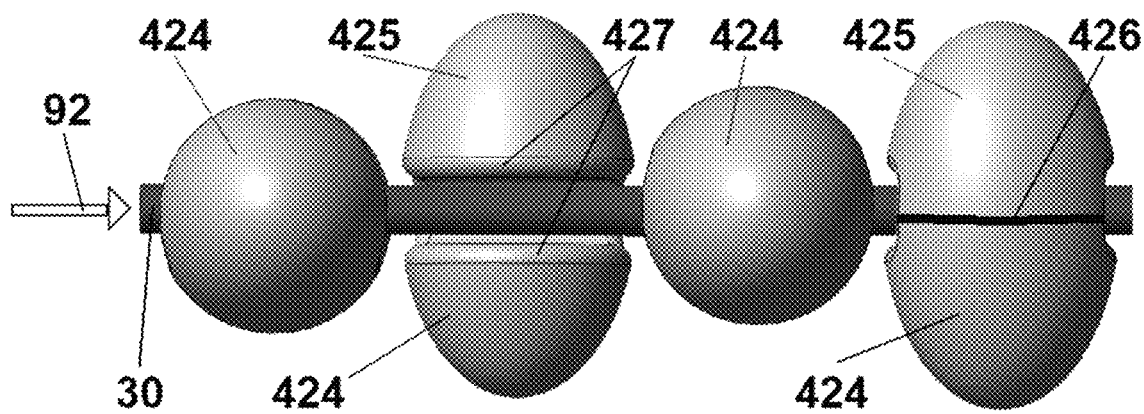

Another way to increase efficiency and reduce duration of the cleaning and decontamination, an array of multiple double-applicators 420-423 can be used, by arranging them in a sequential manner, as it is presented in the embodiment from FIGS. 42A and 42B. The cleaning and decontamination array from FIGS. 42A and 42B has a total of four applicators that include the first double-applicator 420, the second double-applicator 421, the third double-applicator 422, and the fourth double-applicator 423. The four double-applicators 420, 421, 422, and 423 are all constructed by using an upper applicator 424 and the lower applicator 425, which are connected together via the assembly ring 426. In the middle section of the double applicators 420-423 and on the top of their apertures sits a U-shape symmetric membrane 427. In this way an enclosed space filled with fluid is created in which the pseudo-planar pressure waves 40 or the acoustic radial pressure waves 40 or unfocused pressure waves are created. To provide a more efficient spatial distribution, all four double-applicators 420, 421, 422, and 423 are rotated with 90 degrees in the same direction (clockwise or counterclockwise) and positioned along the endoscope 30 or the reusable contaminated tubing 30. There might be other embodiments that can have more than four applicators, depending on the type of endoscope 30 or the reusable contaminated tubing 30 and the efficiency or duration of the cleaning and high-level disinfection process.

For the embodiment from FIGS. 42A and 42B, a liquid bath 93 is needed to allow the proper action of the pseudo-planar pressure waves 40 or of the acoustic radial pressure waves 40 or of the unfocused pressure waves on both the external surface and internal lumen/lumens of the endoscope 30 or the reusable contaminated tubing 30. The liquid bath 93 and the pseudo-planar pressure waves 40 or the acoustic radial pressure waves 40 or unfocused pressure waves are not shown in FIGS. 42A and 42B for simplicity. Also, for a good cleaning and high-level disinfection on the full length of the endoscopes 30, or of the reusable contaminated tubing 30 from respirators, hemodialysis units, and any other medical devices, the endoscopes/tubes need to move in the tubing/endoscope moving direction 92. The operator needs to closely monitor the movement of the endoscope 30 or the reusable contaminated tubing 30 to be sure that it remains in the proper position in the U-shape space of the double-applicators 420, 421, 422, and 423 and in close contact with the U-shape symmetric membrane 427 throughout the whole cleaning and decontamination process. The monitoring can be done visually by the operator or by using an automatic system and special guiding fixtures to have the endoscope 30 or the reusable contaminated tubing 30 constantly in the proper position relatively to the double-applicators 420, 421, 422, and 423.

For the embodiment presented in FIGS. 42A and 42B the double-applicators 420, 421, 422, and 423 can use all types of generation principles for creating pseudo-planar pressure waves 40 or the acoustic radial pressure waves 40 or unfocused pressure waves using electrohydraulic generators (with spark-gaps or lasers), piezoelectric generators (with piezo crystals/piezo ceramics or piezo fibers) or electromagnetic generators (with flat coils or cylindrical coils). To assure the complete cleaning and decontamination on the full length of medical devices such as endoscopes 30, or of the reusable contaminated tubing 30 from respirators, hemodialysis units and any other medical devices, either the contaminated device/part needs to move or alternatively the double-applicators 420, 421, 422, and 423 can move in synchronicity and sometimes both (applicators and endoscope/tubing), using manually or motorized automatic means. In FIGS. 42A and 42B the endoscope 30, or reusable contaminated tubing 30 from respirators or hemodialysis units or from any other medical devices is moving in the tubing/endoscope moving direction 92 and in front of the pseudo-planar pressure waves 40 or the acoustic radial pressure waves 40 or the unfocused pressure waves.

Figure 43:
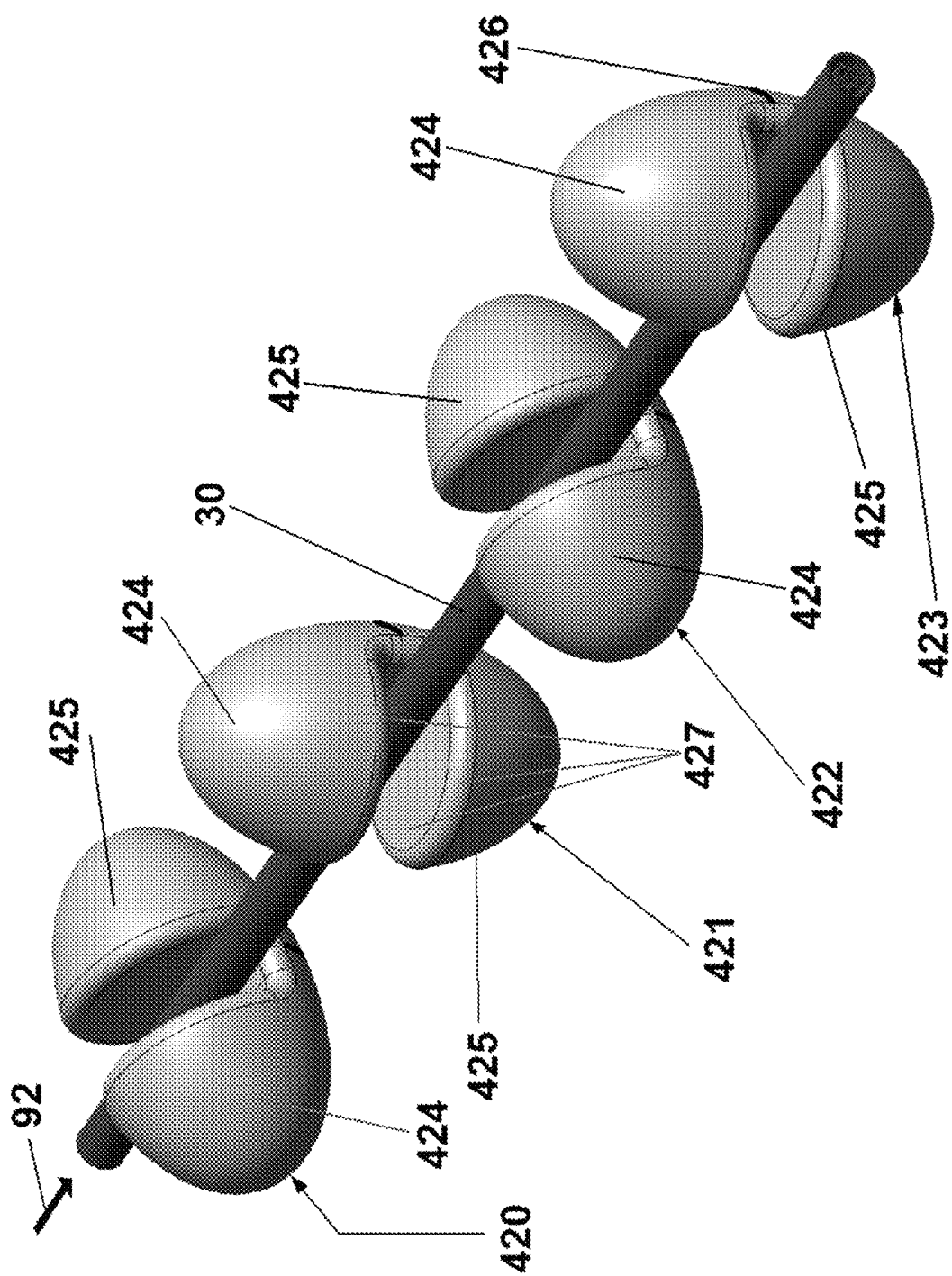
FIG. 43 is a schematic representation of a system with an array of four double-applicators rotating with 90 degrees back and forth that are producing radial or pseudo-planar pressure waves for cleaning and high-level disinfection of endoscopes or tubing from ventilators and dialysis machines and other medical devices, according to one embodiment of the present invention.

In FIG. 43 is presented another embodiment where the multiple double-applicators 420-423 are arranged in a sequential manner, but this time by rotating them with 90 degrees back and forth and positioned along the endoscope 30 or the reusable contaminated tubing 30. For the cleaning and decontamination array from FIG. 43 all the elements, their numerical depiction, and the array specific functioning are the same as those described before in FIGS. 42A and 42B.

The automated endoscope reprocessors (AER) offer several advantages over manual reprocessing since they automate and standardize several important reprocessing steps, reduce the likelihood that an essential reprocessing step will be skipped, and reduce personnel exposure to high-level disinfectants or chemical sterilants. Failure of AERs has been linked to outbreaks of infections or colonization, and the AER water filtration system might not be able to reliably provide "sterile" or bacteria-free rinse water. AERs need further development and redesign, as do endoscopes, to subsequently not representing a potential source of infectious agents.

The embodiment from FIGS. 44A, 44B, and 44C shows a cleaning and disinfection automatic reprocessor 440 that is using the focused acoustic pressure shockwaves 40 or pressure waves (pseudo-planar pressure waves 40 or acoustic radial pressure waves 40 or unfocused pressure waves) to process endoscopes 30, or reusable contaminated tubing/tubes 30 from respirators or hemodialysis units or from any other medical devices. The cleaning and disinfection automatic reprocessors 440 are formed by a reprocessor upper lid 441 and by the reprocessor bottom liquid bath 442 that are connected via the hinge 443. The reprocessor upper lid 441 is in the shape of a semi-ellipsoidal reflector 42 to produce focused acoustic pressure shockwaves 40 or unfocused pressure waves (if the focal point 47 is beyond and outside the reprocessor bottom liquid bath 442) or parabolic reflector 51 to produce focused acoustic pressure shockwaves 40 (if the parabolic focal point is in the reprocessor bottom liquid bath 442) or pseudo-planar pressure waves 40 (if the parabolic focal point is in the reprocessor upper lid 441) or combination semi-spherical and conical reflector 61 (to produce acoustic radial pressure waves 40). The hinge 443 is allowing the reprocessor upper lid 441 to pivot relatively to the reprocessor bottom liquid bath 442 and thus to open or close shut the cleaning and disinfection automatic reprocessors 440. The reprocessor bottom liquid bath 442 has attached to it the reprocessor control console 445 from where the functionality of the cleaning and disinfection automatic reprocessors 440 is controlled. The reprocessor control console 445 is designed to have processors and microprocessors, displays, input/output elements, timers, memory units, remote control devices, independent power unit, etc. Each of these components may include hardware, software, or a combination of hardware and software configured to perform one or more functions associated with providing good functioning of the whole cleaning and disinfection automatic reprocessors 440. The reprocessor upper lid 441 has attached to its top the reprocessor power supply 444 that provides power to the first electrode 45A and the second electrode 45B that are forming the spark-gap 41 that sits in $F_1$ that can be the first ellipsoidal focal point or the parabolic focal point or the sphere central point. To be easily accessible the cleaning and disinfection automatic reprocessors 440 has four legs 446. The whole volume of the cleaning and disinfection automatic reprocessors 440 is filled with the washing and cleaning fluid 447, when the endoscopes 30 or reusable contaminated tubing/tubes 30 from respirators or hemodialysis units or from any other medical devices are cleaned and decontaminated. At their turn the endoscopes 30 or reusable contaminated tubing/tubes 30 are/is also filled with decontamination fluid 205 (see FIGS. 20B and 21B) that can be stagnant or continuously circulated during cleaning and high-level disinfection process. For this embodiment mostly the internal endoscope channels 170 or the lumen/lumens of the reusable contaminated medical tubing 30 are cleaned and decontaminated. If the external surface of the endoscopes 30 or reusable contaminated tubing/tubes 30 needs to be also cleaned and decontaminated, that can be done prior to the introduction inside the cleaning and disinfection automatic reprocessors 440 or if the endoscopes 30 or reusable contaminated tubing/tubes 30 are/is suspended in special bags positioned in the targeted zone of the reprocessor bottom liquid bath 442. The cleaning and disinfection automatic reprocessors 440 can reprocess for cleaning and decontamination one or multiple endoscopes 30 or reusable contaminated tubing/tubes 30.

As seen from FIGS. 44A, 44B, 44C, 45A and 45B, the endoscopes 30 or reusable contaminated tubing/tubes 30 are placed in the reprocessor bottom liquid bath 442 where the focused acoustic pressure shockwaves 40 produce their focal volume 48 (see FIG. 4) or the pseudo-planar pressure waves 40 produce their pseudo-planar waves pressure field 55 (see FIG. 5) or acoustic radial pressure waves 40 produce their radial waves pressure field 63 (see FIG. 6) or unfocused pressure waves can be found.

Although the embodiment presented in FIGS. 44A-44C shows specifically an electrohydraulic system that uses the spark-gap 41, the cleaning and disinfection automatic reprocessor 440 can also produce focused acoustic pressure shockwaves 40 or pressure waves (pseudo-planar pressure waves 40 or acoustic radial pressure waves 40 or unfocused pressure waves) using electrohydraulic generators with lasers, piezoelectric generators (with piezo crystals/piezo ceramics or piezo fibers) or electromagnetic generators (with flat coils or cylindrical coils).

Figure 45B:
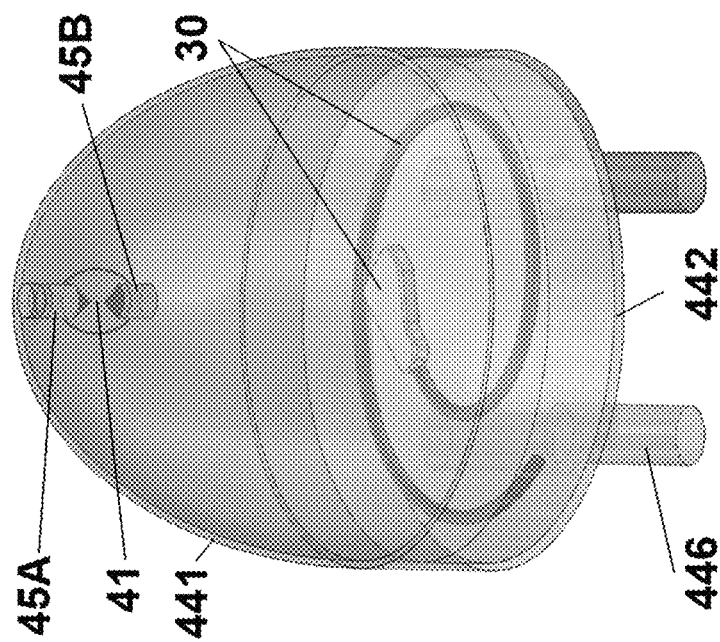
FIGS. 45A and 45B are schematic 3D representations of an automatic shockwaves or pseudo-planar waves or radial waves reprocessor, as show in FIGS. 44A-44C, with one reflector for cleaning and high-level disinfection of endoscopes or tubing from ventilators and dialysis machines and other medical devices, according to one embodiment of the present invention.
Figure 45A:
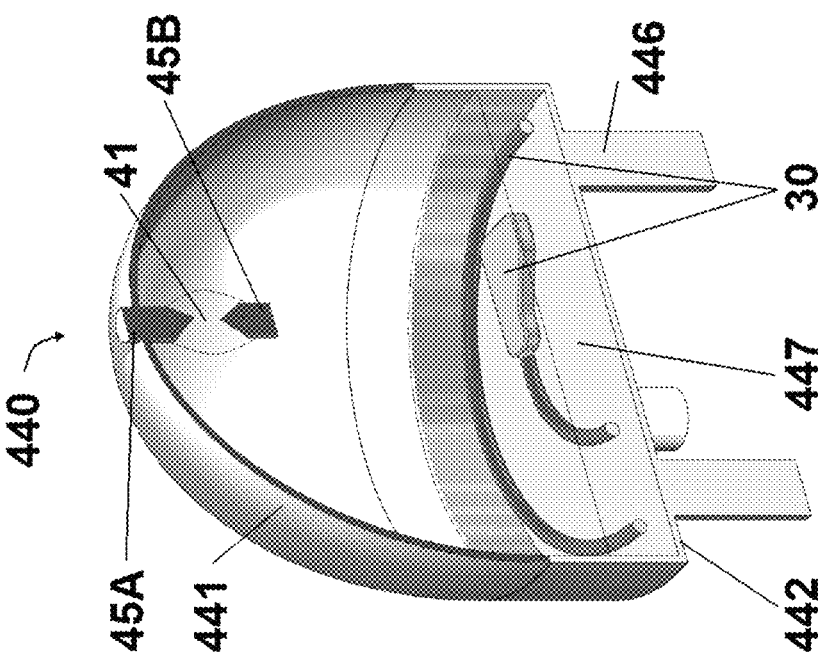

FIGS. 45A and 45B represents a three-dimensional depiction of the cleaning and disinfection automatic reprocessor 440 that had its components and functionality described in detail in FIGS. 44A-44C. In FIGS. 45A and 45B the hinge 443 is in the back of the three-dimensional representation and for simplicity the reprocessor power supply 444 and reprocessor control console 445 were removed.

Figure 46B:
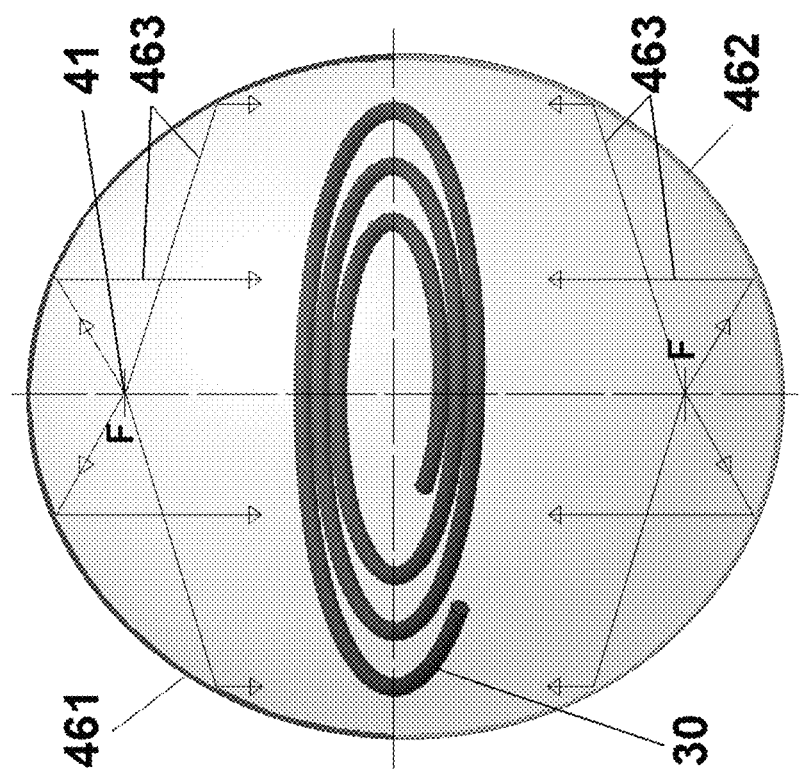
FIGS. 46A and 46B are schematic representations of an automatic shockwave or pseudo-planar waves or radial waves reprocessor with two opposite reflectors for cleaning and high-level disinfection of endoscopes or tubing from ventilators and dialysis machines and other medical devices, according to one embodiment of the present invention.
Figure 46A:
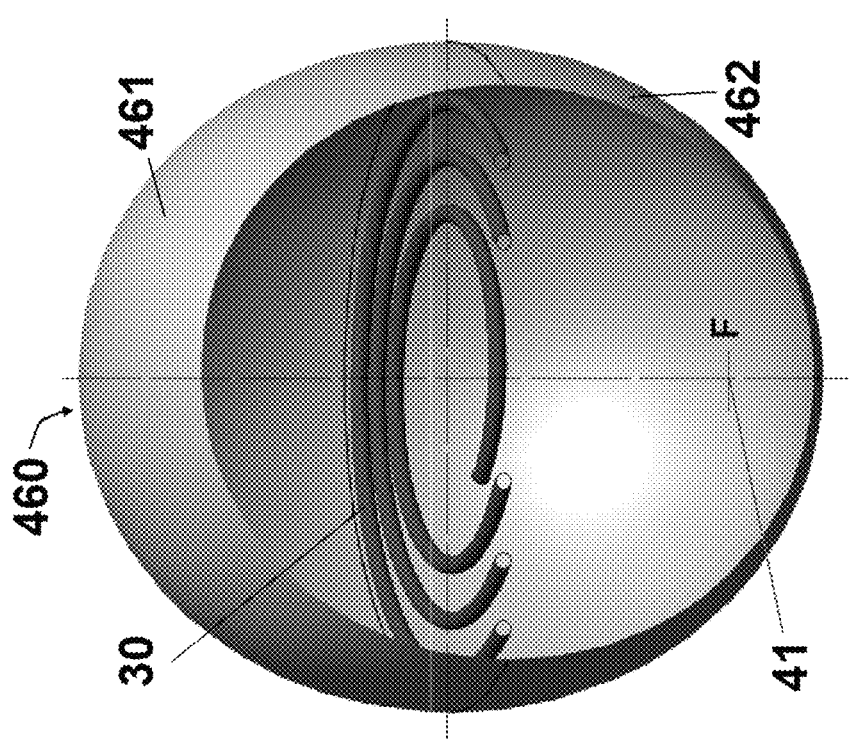

For increased efficiency, in FIGS. 46A and 46B is presented a reprocessor with two opposite reflectors 460. Practically, the reprocessor bottom liquid bath 442 of the cleaning and disinfection automatic reprocessor 440 (from FIGS. 44A-45B) is replaced with another reflector-like structure, similar to the reprocessor upper lid 441, as seen in FIGS. 44A-45B. Thus the reprocessor with two opposite reflectors 460 is formed by the top reflector 461 and the lower reflector 462. Both these reflectors have their own focal point F from where the focused acoustic pressure shockwaves 40 or pressure waves (pseudo-planar pressure waves 40 or acoustic radial pressure waves 40 or unfocused pressure waves) are originating and then focused or directed towards the endoscopes 30 or reusable contaminated tubing/tubes 30 from respirators or hemodialysis units or from any other medical devices. One or multiple endoscopes 30 or reusable contaminated tubing/tubes 30 for this embodiment are sitting on a platform (not shown in FIGS. 46A and 46B) that allows the shockwaves or pressure waves to go through and in the targeted zone for the two reflectors 461 and 462, where the shockwave/pressure waves have maximum action for cleaning and decontamination. The platform can be made of a thin plastic sheath or can be a specially designed bag suspended in the targeted zone of the reflectors 461 and 462 of the reprocessor with two opposite reflectors 460. The platform or the bag can be raised or lowered in a continuous motion during the reprocessing to increase efficiency of the cleaning and the high-level disinfection. For this embodiment both the external surface and the internal endoscope channels 170 or the lumen/lumens of the reusable contaminated medical tubing 30 are cleaned and decontaminated. The reprocessor with two opposite reflectors 460 can reprocess for cleaning and decontamination one or multiple endoscopes 30 or reusable contaminated tubing/tubes 30. The two reflectors 461 and 462 of the reprocessor with two opposite reflectors 460 can be activated simultaneously or sequential. If more energy is needed for cleaning and high-level disinfection then the two reflectors 461 and 462 are activated simultaneously, with the risk of some interference in between upper and lower shockwaves or pressure waves. If no interference is desired then the two reflectors 461 and 462 are activated sequential at very short time intervals.

Utilizing the shockwaves or pressure waves for the cleaning and the decontamination of the endoscopes 30 or of the reusable contaminated tubing 30 from respirators, hemodialysis units and any other medical devices, is accomplished with a 5 kV-30 kV high voltage per discharge, with frequencies of 1 to 12 Hz (preferable 2 to 10 Hz) and generating energies in the targeted area higher than 0.01 mJ/mm$^2$ and less than 1.5 mJ/mm$^2$). The ultrasound used in the embodiments presented in this invention have a frequency in between 10 to 900 kHz, and more preferable 30 to 300 kHz. Also, the low-frequency ultrasound utilized in these inventions operate at 500-1200 Volts (V) peak-to-peak (preferable 600-800 V) and power of 5 to 15 Watts (W) (preferable 6 to 12 W). The dosage of shockwaves/pressure waves and low-frequency ultrasound is chosen in such way to not destroy integrity of delicate materials or components (e.g., fiber optics from the endoscopes, or special valves, etc.). Also, for all embodiments from these inventions an equilibrium must be found in between the input energy, output energy and the possibility to clean and high-level disinfect the medical instrument or reusable component/part for many cycles using focused acoustic pressure shockwaves 40 or pressure waves (acoustic planar pressure wave 374 or pseudo-planar pressure wave 40 or acoustic radial pressure wave 40) and low-frequency ultrasound waves 380 and 381, without any damage that can affect the proper functionality of the medical instrument or reusable component/part.

In all the embodiments presented in these inventions, the focused acoustic pressure shockwaves 40, or pressure waves (acoustic planar pressure wave 374 or pseudo-planar pressure wave 40 or acoustic radial pressure wave 40), or low-frequency ultrasound waves 380 and 381 can be used in conjunction with biocides that are mixed with the simple fluids used for cleaning and decontamination, which can enhance even more their effects on bacteria, viruses, funguses, micro-organisms, or biofilms.

In all embodiments presented in these inventions the decontamination fluid 205 (see FIGS. 20B and 21B) that fills the endoscope channels 170 or the lumen/lumens of the reusable contaminated tubing 30 can be stagnant or continuously circulated during cleaning and high-level disinfection process. Either way a pumping system is employed to fill different channels and lumens of the endoscopes 30 or reusable contaminated tubing/tubes 30. This pumping system is not depicted in any of the figures of these inventions, since such a system is well known element and also to achieve a necessary simplicity of the figures, where more important elements need to be present and described in detail.

Although, throughout these inventions it was mentioned that the focused acoustic pressure shockwaves 40 or pressure waves (acoustic planar pressure wave 374 or pseudo-planar pressure wave 40 or acoustic radial pressure wave 40) and low-frequency ultrasound waves 380 and 381 are used to clean and disinfect endoscopes 30 or reusable contaminated tubing/tubes 30 from ventilators and dialysis machines or from any other medical devices, it is understood that the same cleaning and high-level disinfection methods presented into the embodiments of these inventions can be applied to any medical one-lumen tubing or multi-lumen tubing or multi-tubing bundled inside an external sheath that constitute a medical system or a part of a medical device or system that needs reusing and cannot be subject to sterilization process or chemical cleaning and disinfection that can affect its integrity.

All the membranes from the embodiments of these inventions are made of a soft plastic material that does not scratch the exterior surface of the endoscopes 30 or of the reusable contaminated tubing 30 when in contact with them. Also, the soft plastic material of the membranes is chosen from materials that have acoustic properties very close to the fluid used inside the applicators 97, 201, 256, 261, 310, 360-363, 382, 410-413, 420-425, and 462-463 or in the fluid baths 93 to not impede with the propagation of focused acoustic pressure shockwaves 40 or pressure waves (acoustic planar pressure wave 374 or pseudo-planar pressure wave 40 or acoustic radial pressure wave 40) and low-frequency ultrasound waves 380 and 381.

Various embodiments of the invention have been described. It will, however, be evident that various modifications and changes may be made thereto, and additional embodiments may be implemented, without departing from the broader scope of the invention as set forth by the claims. This specification is to be regarded in an illustrative rather than a restrictive sense.

What is claimed is:

1. A method for decontaminating a reusable medical apparatus comprising:

providing a reusable medical apparatus with a contaminated condition into an open liquid bath;

inserting a pressure wave applicator into the bath, and directly contacting a membrane of the pressure wave applicator to the reusable medical apparatus in the open liquid bath; and decontaminating the reusable medical apparatus by applying pressure waves, each of said pressure waves having a dominant and steep compressive phase of up to 100 MPa and a tensile phase having a negative pressure of 5 to −15 MPa during one cycle of each pressure wave, during direct contact of the pressure wave applicator to the reusable medical apparatus in the open liquid bath to remove the contaminated condition of the reusable medical apparatus.

2. The method of claim 1, wherein the reusable medical apparatus contains tubing.

3. The method of claim 1, wherein the contaminated condition includes at least one of bacterial, fungal, and viral contamination.

4. The method of claim 1, wherein the contaminated condition includes particulates.

5. The method of claim 1, further comprising applying focused shockwaves generated by the applicator to the reusable medical apparatus.

6. The method of claim 1, further comprising applying at least one of planar, pseudo-planar, radial, and unfocused pressure waves generated by the applicator to the reusable medical apparatus.

7. The method of claim 1, further comprising applying ultrasound waves having a frequency from 10 to 900 kHz generated by the applicator to the reusable medical apparatus.

8. The method of claim 1, further comprising using a reflector of the applicator to direct the pressure waves from the applicator to the reusable medical apparatus.

9. The method of claim 1, further comprising using one of a spark gap, electromagnetic generator, and piezoelectric generator in the applicator to generate the pressure waves.

10. The method of claim 1, wherein the membrane is U-shaped and seals a U-shaped opening of the applicator that is shaped to receive the reusable medical apparatus.

11. The method of claim 1, wherein the membrane is shaped to receive the reusable medical apparatus.

12. The method of claim 1, wherein the membrane has a conical, cylindrical or L-shape.

13. The method of claim 2, wherein the reusable medical apparatus is an endoscope.

14. The method of claim 2, wherein the reusable medical apparatus is tubing of a dialysis machine or ventilator.

15. The method of claim 2, further comprising applying at least one of planar, pseudo-planar, radial and unfocused pressure waves generated by the applicator to the reusable medical apparatus.

16. The method of claim 2, further comprising applying focused shockwaves generated by the applicator to the reusable medical apparatus.

17. The method of claim 5, further comprising using a reflector of the applicator to direct the shockwaves from the applicator to the reusable medical apparatus.

18. The method of claim 10, wherein the reusable medical apparatus contains tubing.

19. The method of claim 11, wherein the reusable medical apparatus contains tubing.

* * * * *